(12) United States Patent
Prat et al.

(10) Patent No.: US 8,703,711 B2
(45) Date of Patent: Apr. 22, 2014

(54) NINJURIN-1 MODULATION AND USES THEREOF

(75) Inventors: Alexandre Prat, Outremont (CA); Simone Terouz, Ville Saint-Laurent (CA); Igal Ifergan, Ville Saint-Laurent (CA); Hania Kebir, Montreal (CA)

(73) Assignee: Val-Chum, Limited Partnership, Montrel (CA)

( * ) Notice: Subject to any disclaimer, the term of this patent is extended or adjusted under 35 U.S.C. 154(b) by 102 days.

(21) Appl. No.: 12/796,221

(22) Filed: Jun. 8, 2010

(65) Prior Publication Data

US 2010/0310568 A1  Dec. 9, 2010

Related U.S. Application Data

(60) Provisional application No. 61/185,420, filed on Jun. 9, 2009.

(30) Foreign Application Priority Data

Aug. 25, 2009 (AU) ................................ 2009212789
Aug. 25, 2009 (CA) ..................................... 2676962

(51) Int. Cl.
*A01N 37/18* (2006.01)
*A01N 61/00* (2006.01)
*A61K 38/00* (2006.01)

(52) U.S. Cl.
USPC ......... 514/17.9; 514/5.2; 514/17.7; 514/18.2; 514/21.5

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 6,025,155 A | 2/2000 | Hadlaczky et al. | |
| 6,077,677 A | 6/2000 | Hodgson et al. | |
| 6,140,117 A * | 10/2000 | Milbrandt et al. | 435/325 |
| 6,204,023 B1 | 3/2001 | Robinson et al. | |
| 6,559,288 B1 | 5/2003 | Milbrandt et al. | |
| 6,893,828 B2 * | 5/2005 | Hakonarson et al. | 435/7.21 |
| 2002/0160970 A1 | 10/2002 | Hadlaczky et al. | |
| 2003/0083293 A1 | 5/2003 | Hadlaczky et al. | |
| 2010/0015117 A1 | 1/2010 | Verma et al. | |

FOREIGN PATENT DOCUMENTS

| | | | |
|---|---|---|---|
| KR | 10-2008-0124555 | * | 1/2009 |
| WO | WO-2010/067915 A1 | | 6/2010 |

OTHER PUBLICATIONS

Jerregard, 2001, J. Neurocytology, 30, pp. 327-336.*
Zhang et al., 2006, Genes and development, 20, pp. 1899-1910.*
Noseworthy et al.,"Linomide in relapsing and secondary progressive MS: Part I: Trial and design and clinical results", (2000) Neurology 54(9): 1726-33.
Andersson and Goodkin, "Glucocorticosteroid therapy for multiple sclerosis: A critical review", (1998) J Neurol Sci. 160 (1): 16-25.
Bansil et al., "Multiple sclerosis: immune mechanism and update on current therapies", (1995) Ann Neurol. 37 Suppl 1: S87-101.
C. F. Lacy et al., Drug information handbook 8th Edition, 2001, pp. 549-551.
Karin N. et al., "Reversal of experimental autoimmune encephalomyelitis by a soluble peptide variant of a myelin basic protein epitope: T cell receptor antagonism and reduction of interferon y and tumor necrosis factor a production", (1994) J Exp Med. 180(6): 2227-37.
Rolak L.A., "Mutliple sclerosis treatment 2001", (2001) Neurol Clin. 19(1): 107-18.
Bracken et al., "Administration of methylprednisolone for 24 or 48 hours or tirilazad mesylate for 48 hours in the treatment of acute spinal cord injury", JAMA, 277(20): 1597-1604 (1997).
Schröter et al., "High-dose corticosteroids after spinal cord injury reduce neural progenitor cell proliferation", Neuroscience 2009 161(3): 753-63. Epub Apr. 11, 2009.
Basso D.M. et al., "Basso mouse scale for locomotion detects differences in recovery after spinal cord injury in five common mouse strains", (2006). J Neurotrauma. 23(5): 635-59.
Araki et al., "Mechanism of homophilic binding mediated by ninjurin, a novel widely expressed adhesion molecule", J. Biol Chem. 1997 272(34) 21373-21380.
Binz and Plückthun, "Engineered proteins as specific binding reagents", 2005, Curr. Opin. Biotech. 16: 1-11.
Ken A. Witt et al., "CNS drug delivery: opioid peptides and the blood-brain barrier", AAPS Journal. 2006; 8(1): E76-E88.
Misra et al., "Drug delivery to the central nervous system: a review", J Pharm Pharmaceut Sci 6(2):252-273, 2003.
Pathan et al., "CNS drug delivery systems: novel approaches", Recent Patents on Drug Delivery & Formulation 2009, 3: 71-89.
Prat et al., "Kirin B1 receptor expression and function on human brain endothelial cells", J Neuropathol Exp Neurol. 2000 59(10):896-906.
Biernacki et al., "Regulation of Th1 and Th2 lymphocyte migration by human adult brain endothelial cells", J Neuropathol Exp Neurol. 2001 60(12): 1127-36.
Prat et al., "Migration of multiple sclerosis lymphocytes through brain endothelium", Arch Neurol. 2002 59(3): 391-7.
Livak and Schmittgen, "Analysis of relative gene expression data using real-time quantitative PCR and the 2-**ct method", Methods 2001 25(4): 402-408.

* cited by examiner

*Primary Examiner* — Olga N Chernyshev
(74) *Attorney, Agent, or Firm* — Goudreau Gage Dubuc; S. Serge Shahinian; Alain Dumont

(57) ABSTRACT

Methods, uses, agents and compositions useful for the prevention, treatment and/or diagnosis of neuroinflammatory conditions such as multiple sclerosis and spinal cord injury based on the modulation of nerve injury-induced protein-1 (Ninjurin-1) are disclosed.

11 Claims, 25 Drawing Sheets

FIG. 7A
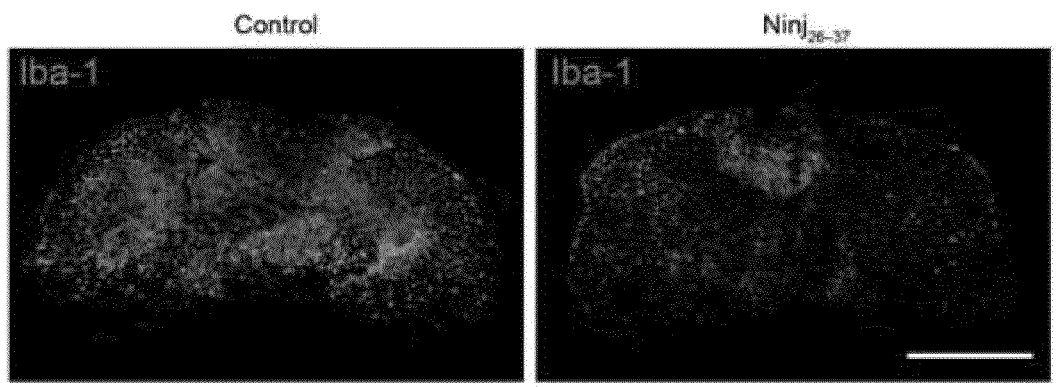
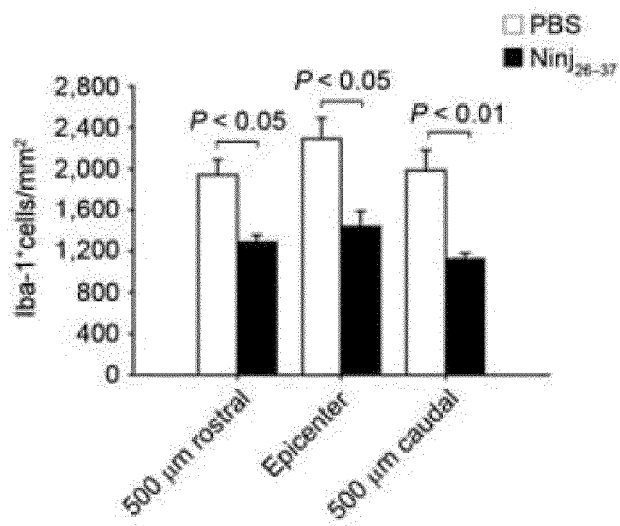
FIG. 7B

```
   1 cgcagctgga gcctgcggct gaggctcggg cgcgctcagg cccggatcct ggcggcctgg
  61 gcggccgcac catggactcg ggaaccgagg agtacgagct caacggcggc ctgcctccgg
 121 gcacacccgg ctccccggac gcctcgccgg cccgctgggg ctggaggcac gggcccatca
 181 acgtgaacca ttacgccagc aagaagagcg cagccgagag catgctggac atcgcgctgc
 241 tgatggccaa cgcgtcccag ctgaaggccg tcgtggaaca gggccccagc ttcgccttct
 301 atgtgcccct ggtggtcctc atctccatct cccttgtgct gcagatcggc gtggggtgc
 361 tgctcatctt ccttgtcaag tacgacctta acaacccggc caagcacgcc aagctggact
 421 tcctcaacaa cctggccacg ggcctggtgt tcatcatcgt ggtagtcaac atcttcatca
 481 cggccttcgg ggtccagaag cccttgatgg acatggcacc ccagcagtag gacacccagg
 541 accctggatg ctgcctgccc tgcaactcag ctgccccgacc ccaggagtcg ccatacctgt
 601 gaggtgtcca cctccctgca catggcacta cccagactgc cagagcccag gctggcctca
 661 tctgcaccat gtccccggac cagcccttgc tctgactgcg gccaagcacc acgcaggagg
 721 ccactcttgt ctctcagcag ctgttcccag gaggcagctc cctcctggca catgggggct
 781 ggccacaata cccagagggg tcagaactgg acagctgcag agacctgtgc cagagaagg
 841 gtctcgaccc actcaaggac acacagcagg tccgtggatg ggctggatga gtgaccaggg
 901 ccagcctctg tctcaggaca ttccagaagg acaaggagat gtctctccct ctcccaaagc
 961 accagcgtcc ctgcctcccg tgggccctgt ccgggttgcc ctgctgaccc cagcctctgt
1021 ccacttccta acccagggac cctgcacagc cagaactgcc tttggcccta cggatggcca
1081 ctggctctgg tcttaagtgc ctgggcttgg tggccatcaa gagggagcca gtcaggcctg
1141 tgagggccgt agaccttgta tataccctgc accagcagtg accgggcaga gcccaacccc
1201 ctccacgggg gtcccagcac ccactttcct aatcatgaat gaacaataaa gcccacgctc
1261 tttgtcaggc tccacatgcc aaaaaaaaaa aaaaaaa
```

FIG. 8A

```
  1 mdsgteeyel ngglppgtpg spdasparwg wrhgpinvnh yaskksaaes mldiallman
 61 asqlkavveq gpsfafyvpl vvlisislvl qigvgvllif lvkydlnnpa khakldflnn
121 latglvfiiv vvnifitafg vqkplmdmap qq
```

FIG. 8B

```
   1 cccgggcggc cgcaccatgg agtcgggcac tgaggagtat gagctcaacg gcgacctgcg
  61 cccgggctcc cccggttccc ccgacgcctt gccacccccgc tggggtttgc ggaaccggcc
 121 catcaatgta aaccattatg ccaacaagaa gagcgctgcg gagagcatgc tggacatcgc
 181 gctgctcatg ccaacgcgt cgcagctgaa ggccgtggtg gagcagggca atgatttcgc
 241 cttcttcgtg cccccttgtgg tcctcatctc tatctccctc gtgctgcaga taggagtggg
 301 cgtgctgctc atcttcctgg tcaagtatga cctcaacaac ccggccaagc acgccaagct
 361 ggactttctt aacaacctgg ccacgggact ggttttcatc atcgtcgtgg tcaacatctt
 421 cattacggcc ttcggggtcc agaagccgt aatggacgtg gcgccccggc agtagaacgc
 481 ccagagactt taagggtacc ggacctgcag cccagctgac cagaccctg caactgctgt
 541 accccccaagg tatccctctc ctgtgtgcag agcccaaggt ggccaccgct ggaccatggt
 601 cagggacgga cttccgtcca actgtgaccg ctgtgtgggc ggccacctga cacatgtggg
 661 aaccggatgc agggccatga agatcagaac tggacagctc catagaaacc caagtccaga
 721 gaatggtcac tgcccaccca aggacatgca gcaaatccat gattggactt gacgaggggc
 781 cagcactggc ctctgtctca ggacattcca gaaggaccag gatatgcccc tccctttgct
 841 gatacaccag tgacctact tctcatggag cctgcccagg tcaccctgga gactgctgcc
 901 tttgttgttt cttgacccag ggaccttgga cagccatcag tatctgctgg ctccagcctc
 961 agtgcctggg cttggcagcc atcaagaggc agccatgccc gtggggctg caggtcatgc
1021 tggtacttcc tgccagtggt gacctgggta gagccccagc cctcaactca ggggttcagg
1081 ccccactttt ctaatcagga acgacaataa agcttatgtg cttccctgct gg
```

FIG. 8C

```
   1 mesgteeyel ngdlrpgspg spdalpprwg lrnrpinvnh yankksaaes mldiallman
  61 asqlkavveq gndfaffvpl vvlisislvl qigvgvllif lvkydlnnpa khakldflnn
 121 latglvfiiv vvnifitafg vqkpvmdvap rq
```

FIG. 8D

|                     | EAE score ≥ 3.0 |        |        |        |        |        |        |
|---------------------|--------|--------|--------|--------|--------|--------|--------|
| Treatment group     | Day 11 | Day 12 | Day 13 | Day 14 | Day 15 | Day 16 | Day 17 |
| Isotype control     | 0/8    | 0/8    | 0/8    | 0/8    | 3/8    | 6/8*   | 6/8*   |
| Anti-Ninjurin-1 Ab  | 0/8    | 0/8    | 0/8    | 0/8    | 1/8    | 2/8    | 2/8    |
|                     |        |        |        |        |        |        |        |
| Scramble            | 0/8    | 0/8    | 4/8*   | 4/8*   | 4/8*   | 4/8*   | 4/8*   |
| Ninj$_{26-37}$      | 0/8    | 0/8    | 0/8    | 0/8    | 0/8    | 0/8    | 0/8    |

FIG. 16

SEQUENCE LISTING

```
<160> NUMBER OF SEQ ID NOS: 16

<210> SEQ ID NO 1
<211> LENGTH: 1297
<212> TYPE: DNA
<213> ORGANISM: Homo sapiens
<220> FEATURE:
<221> NAME/KEY: CDS
<222> LOCATION: (72)..(530)

<400> SEQUENCE: 1
cgcagctgga gcctgcggct gaggctcggg cgcgctcagg cccggatcct ggcggcctgg      60
gcggccgcac c atg gac tcg gga acc gag gag tac gag ctc aac ggc ggc     110
            Met Asp Ser Gly Thr Glu Glu Tyr Glu Leu Asn Gly Gly
              1               5                  10 ctg cct ccg ggc aca ccc ggc tcc ccg gac gcc tcg ccg gcc cgc tgg     158
Leu Pro Pro Gly Thr Pro Gly Ser Pro Asp Ala Ser Pro Ala Arg Trp
         15                  20                  25 ggc tgg agg cac ggg ccc atc aac gtg aac cat tac gcc agc aag aag     206
Gly Trp Arg His Gly Pro Ile Asn Val Asn His Tyr Ala Ser Lys Lys
 30                  35                  40                  45 agc gca gcc gag agc atg ctg gac atc gcg ctg ctg atg gcc aac gcg     254
Ser Ala Ala Glu Ser Met Leu Asp Ile Ala Leu Leu Met Ala Asn Ala
                 50                  55                  60 tcc cag ctg aag gcc gtc gtg gaa cag ggc ccc agc ttc gcc ttc tat     302
Ser Gln Leu Lys Ala Val Val Glu Gln Gly Pro Ser Phe Ala Phe Tyr
             65                  70                  75 gtg ccc ctg gtg gtc ctc atc tcc atc tcc ctt gtg ctg cag atc ggc     350
Val Pro Leu Val Val Leu Ile Ser Ile Ser Leu Val Leu Gln Ile Gly
         80                  85                  90 gtg ggg gtg ctg ctc atc ttc ctt gtc aag tac gac ctt aac aac ccg     398
Val Gly Val Leu Leu Ile Phe Leu Val Lys Tyr Asp Leu Asn Asn Pro
 95                 100                 105
```

```
gcc aag cac gcc aag ctg gac ttc ctc aac aac ctg gcc acg ggc ctg         446
Ala Lys His Ala Lys Leu Asp Phe Leu Asn Asn Leu Ala Thr Gly Leu
110             115                 120                 125 gtg ttc atc atc gtg gta gtc aac atc ttc atc acg gcc ttc ggg gtc         494
Val Phe Ile Ile Val Val Val Asn Ile Phe Ile Thr Ala Phe Gly Val
                130                 135                 140 cag aag ccc ttg atg gac atg gca ccc cag cag tag  dacacccagg             540
Gln Lys Pro Leu Met Asp Met Ala Pro Gln Gln
            145                 150 accctggatg ctgcctgccc tgcaactcag ctgcccgacc ccaggagtcg ccatacctgt       600
gaggtgtcca cctccctgca catggcacta cccagactgc cagagcccag gctggcctca       660
tctgcaccat gtccccggac cagcccttgc tctgactgcg ccaagcacc acgcaggagg        720
ccactcttgt ctctcagcag ctgttcccag gaggcagctc cctcctggca catgggggct       780
ggccacaata gcccagaggg tcagaactgg acagctgcag agacctgtgc cagagaagg        840
gtctcgaccc actcaaggac acacagcagg tccgtggatg ggctggatga gtgaccaggg       900
ccagcctctg tctcaggaca ttccagaagg acaaggagat gtctctccct ctcccaaagc       960
accagcgtcc ctgcctcccg tgggcccgtgt ccgggttgcc ctggtgaccc cagcctctgt     1020
ccacttccta acccagggac cctgcacagc cagaactgcc tttggcccta cggatggcca     1080
ctggctctgg tcttaagtgc ctgggcttgg tggccatcaa gagggagcca gtcaggcctg     1140
tgagggccgt agaccttgta tataccctgc accagcagtg accgggcaga gcccaacccc     1200
ctccacgggg gtcccagcac ccactttcct aatcatgaat gaacaataaa gcccacgctc     1260
tttgtcaggc tccacatgcc aaaaaaaaaa aaaaaaa                              1297

<210> SEQ ID NO 2
<211> LENGTH: 152
<212> TYPE: PRT
<213> ORGANISM: Homo sapiens

<400> SEQUENCE: 2

Met Asp Ser Gly Thr Glu Glu Tyr Glu Leu Asn Gly Gly Leu Pro Pro
1               5                   10                  15

Gly Thr Pro Gly Ser Pro Asp Ala Ser Pro Ala Arg Trp Gly Trp Arg
            20                  25                  30

His Gly Pro Ile Asn Val Asn His Tyr Ala Ser Lys Lys Ser Ala Ala
        35                  40                  45

Glu Ser Met Leu Asp Ile Ala Leu Leu Met Ala Asn Ala Ser Gln Leu
    50                  55                  60

Lys Ala Val Val Glu Gln Gly Pro Ser Phe Ala Phe Tyr Val Pro Leu
65                  70                  75                  80

Val Val Leu Ile Ser Ile Ser Leu Val Leu Gln Ile Gly Val Gly Val
                85                  90                  95

Leu Leu Ile Phe Leu Val Lys Tyr Asp Leu Asn Asn Pro Ala Lys His
            100                 105                 110

Ala Lys Leu Asp Phe Leu Asn Asn Leu Ala Thr Gly Leu Val Phe Ile
        115                 120                 125

Ile Val Val Val Asn Ile Phe Ile Thr Ala Phe Gly Val Gln Lys Pro
    130                 135                 140

Leu Met Asp Met Ala Pro Gln Gln
145                 150

<210> SEQ ID NO 3
<211> LENGTH: 1132
```

```
<212> TYPE: DNA
<213> ORGANISM: Mus musculus
<220> FEATURE:
<221> NAME/KEY: CDS
<222> LOCATION: (17)..(475)

<400> SEQUENCE: 3
cccgggcggc cgcacc atg gag tcg ggc act gag gag tat gag ctc aac ggc        52
               Met Glu Ser Gly Thr Glu Glu Tyr Glu Leu Asn Gly
                 1               5                  10 gac ctg cgc ccg ggc tcc ccc ggt tcc ccc gac gcc ttg cca ccc cgc         100
Asp Leu Arg Pro Gly Ser Pro Gly Ser Pro Asp Ala Leu Pro Pro Arg
         15                  20                  25 tgg ggt ttg cgg aac cgg ccc atc aat gta aac cat tat gcc aac aag         148
Trp Gly Leu Arg Asn Arg Pro Ile Asn Val Asn His Tyr Ala Asn Lys
 30                  35                  40 aag agc gct gcg gag agc atg ctg gac atc gcg ctg ctc atg gcc aac         196
Lys Ser Ala Ala Glu Ser Met Leu Asp Ile Ala Leu Leu Met Ala Asn
45                  50                  55                  60 gcg tcg cag ctg aag gcc gtg gtg gag cag ggc aat gat ttc gcc ttc         244
Ala Ser Gln Leu Lys Ala Val Val Glu Gln Gly Asn Asp Phe Ala Phe
                 65                  70                  75 ttc gtg ccc ctt gtg gtc ctc atc tct atc tcc ctc gtg ctg cag ata         292
Phe Val Pro Leu Val Val Leu Ile Ser Ile Ser Leu Val Leu Gln Ile
             80                  85                  90 gga gtg ggc gtg ctc ctc atc ttc ctg gtc aag tat gac ctc aac aac         340
Gly Val Gly Val Leu Leu Ile Phe Leu Val Lys Tyr Asp Leu Asn Asn
         95                 100                 105 ccg gcc aag cac gcc aag ctg gac ttt ctt aac aac ctg gcc acg gga         388
Pro Ala Lys His Ala Lys Leu Asp Phe Leu Asn Asn Leu Ala Thr Gly
110                 115                 120 ctg gtt ttc atc atc gtc gtg gtc aac atc ttc att acg gcc ttc ggg         436
Leu Val Phe Ile Ile Val Val Val Asn Ile Phe Ile Thr Ala Phe Gly
125                 130                 135                 140 gtc cag aag cct gta atg gac gtg gcg ccc cgg cag tag aacgcccaga         485
Val Gln Lys Pro Val Met Asp Val Ala Pro Arg Gln
                 145                 150 gactttaagg gtaccggacc tgcagcccag ctgaccagac ccctgcaact gctgtacccc       545
caaggtatcc ctctcctgtg tgcagagccc aaggtggcca ccgctggacc atggtcaggg       605
acggacttcc gtccaactgt gaccgctgtg tgggcggcca cctgagacat gtgggaaccg       665
gatgcagggc catgaagatc agaactggac agctccatag aaacccaagt ccagagaatg       725
gtcactgccc acccaaggac atgcagcaaa tccatgattg acttgacga ggggccagca        785 ctggcctctg tctcaggaca ttccagaagg accaggatat gcccctccct ttgctgatac       845
accagtgacc ctacttctca tggagcctgc ccaggtcacc ctggagactg ctgcctttgt       905
tgtttcttga cccagggacc ttggacagcc atcagtatct gctggctcca gcctcagtgc       965
ctgggcttgg cagccatcaa gaggcagcca tgcccgtggg gctgcaggt catgctggta      1025 cttcctgcca gtggtgacct gggtagagcc ccagccctca actcagggt tcaggcccca      1085 cttttctaat caggaacgac aataaagctt atgtgcttcc ctgctgg                  1132

<210> SEQ ID NO 4
<211> LENGTH: 152
<212> TYPE: PRT
<213> ORGANISM: Mus musculus

<400> SEQUENCE: 4

Met Glu Ser Gly Thr Glu Glu Tyr Glu Leu Asn Gly Asp Leu Arg Pro
  1               5                  10                  15
```

```
Gly Ser Pro Gly Ser Pro Asp Ala Leu Pro Pro Arg Trp Gly Leu Arg
            20                  25                  30

Asn Arg Pro Ile Asn Val Asn His Tyr Ala Asn Lys Lys Ser Ala Ala
        35                  40                  45

Glu Ser Met Leu Asp Ile Ala Leu Leu Met Ala Asn Ala Ser Gln Leu
 50                  55                  60

Lys Ala Val Val Glu Gln Gly Asn Asp Phe Ala Phe Phe Val Pro Leu
 65                  70                  75                  80

Val Val Leu Ile Ser Ile Ser Leu Val Leu Gln Ile Gly Val Gly Val
                85                  90                  95

Leu Leu Ile Phe Leu Val Lys Tyr Asp Leu Asn Asn Pro Ala Lys His
            100                 105                 110

Ala Lys Leu Asp Phe Leu Asn Asn Leu Ala Thr Gly Leu Val Phe Ile
        115                 120                 125

Ile Val Val Asn Ile Phe Ile Thr Ala Phe Gly Val Gln Lys Pro
130                 135                 140

Val Met Asp Val Ala Pro Arg Gln
145                 150

<210> SEQ ID NO 5
<211> LENGTH: 12
<212> TYPE: PRT
<213> ORGANISM: Homo sapiens

<400> SEQUENCE: 5

Pro Ala Arg Trp Gly Trp Arg His Gly Pro Ile Asn
1               5                   10

<210> SEQ ID NO 6
<211> LENGTH: 12
<212> TYPE: PRT
<213> ORGANISM: Artificial Sequence
<220> FEATURE:
<223> OTHER INFORMATION: Peptide corresponding to residues 26 to 37 of
      human Ninjurin-1

<400> SEQUENCE: 6

Pro Pro Arg Trp Gly Leu Arg Asn Arg Pro Ile Asn
1               5                   10

<210> SEQ ID NO 7
<211> LENGTH: 21
<212> TYPE: PRT
<213> ORGANISM: Artificial Sequence
<220> FEATURE:
<223> OTHER INFORMATION: Residues 35-55 of myelin oligodendrocyte
      glycoprotein

<400> SEQUENCE: 7

Met Glu Val Gly Trp Tyr Arg Ser Pro Phe Ser Arg Val Val His Leu
1               5                   10                  15

Tyr Arg Asn Gly Lys
            20

<210> SEQ ID NO 8
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 8
```

```
agggccatga agatcagaac tgga                                           24
```

<210> SEQ ID NO 9
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 9

```
atggatttgc tgcatgtcct tggg                                           24
```

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10

```
caaagttgtc atggatgacc                                                20
```

<210> SEQ ID NO 11
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 11

```
ccatggagaa ggctgggg                                                  18
```

<210> SEQ ID NO 12
<211> LENGTH: 12
<212> TYPE: PRT
<213> ORGANISM: Artificial Sequence
<220> FEATURE:
<223> OTHER INFORMATION: Control peptide

<400> SEQUENCE: 12

```
Trp Arg Gly Asn Pro Gly Ile Arg Trp Ala Pro His
1               5                   10
```

<210> SEQ ID NO 13
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is any amino acid or is
      absent
<220> FEATURE:
<221> NAME/KEY: MISC_FEATURE
<222> LOCATION: (2)..(2)
<223> OTHER INFORMATION: Xaa at position 2 is any amino acid or is
      absent
<220> FEATURE:
<221> NAME/KEY: MISC_FEATURE
<222> LOCATION: (5)..(6)
<223> OTHER INFORMATION: Xaa at positions 5 and 6 is any amino acid
<220> FEATURE:
<221> NAME/KEY: MISC_FEATURE
<222> LOCATION: (8)..(8)
<223> OTHER INFORMATION: Xaa at position 8 is any amino acid
<220> FEATURE:
<221> NAME/KEY: MISC_FEATURE
<222> LOCATION: (10)..(10)
<223> OTHER INFORMATION: Xaa at position 10 is any amino acid or is

```
      absent
<220> FEATURE:
<221> NAME/KEY: MISC_FEATURE
<222> LOCATION: (11)..(11)
<223> OTHER INFORMATION: Xaa at position 11 is any amino acid or is
      absent
<220> FEATURE:
<221> NAME/KEY: MISC_FEATURE
<222> LOCATION: (12)..(12)
<223> OTHER INFORMATION: Xaa at position 12 is any amino acid or is
      absent

<400> SEQUENCE: 13

Xaa Xaa Arg Trp Xaa Xaa Arg Xaa Arg Xaa Xaa Xaa
1               5                   10

<210> SEQ ID NO 14
<211> LENGTH: 12
<212> TYPE: PRT
<213> ORGANISM: Artificial Sequence
<220> FEATURE:
<223> OTHER INFORMATION: Synthetic peptide
<220> FEATURE:
<221> NAME/KEY: MISC_FEATURE
<222> LOCATION: (1)..(1)
<223> OTHER INFORMATION: Xaa at position 1 is any amino acid or is
      absent
<220> FEATURE:
<221> NAME/KEY: MISC_FEATURE
<222> LOCATION: (2)..(2)
<223> OTHER INFORMATION: Xaa at position 2 is any amino acid or is
      absent
<220> FEATURE:
<221> NAME/KEY: MISC_FEATURE
<222> LOCATION: (5)..(5)
<223> OTHER INFORMATION: Xaa at position 5 is any amino acid
<220> FEATURE:
<221> NAME/KEY: MISC_FEATURE
<222> LOCATION: (8)..(8)
<223> OTHER INFORMATION: Xaa at position 8 is any amino acid or is
      absent
<220> FEATURE:
<221> NAME/KEY: MISC_FEATURE
<222> LOCATION: (9)..(9)
<223> OTHER INFORMATION: Xaa at position 9 is any amino acid or is
      absent
<220> FEATURE:
<221> NAME/KEY: MISC_FEATURE
<222> LOCATION: (10)..(10)
<223> OTHER INFORMATION: Xaa at position 10 is any amino acid or is
      absent
<220> FEATURE:
<221> NAME/KEY: MISC_FEATURE
<222> LOCATION: (11)..(11)
<223> OTHER INFORMATION: Xaa at position 11 is any amino acid or is
      absent
<220> FEATURE:
<221> NAME/KEY: MISC_FEATURE
<222> LOCATION: (12)..(12)
<223> OTHER INFORMATION: Xaa at position 12 is any amino acid or is
      absent

<400> SEQUENCE: 14

Xaa Xaa Arg Trp Xaa Trp Arg Xaa Xaa Xaa Xaa Xaa
1               5                   10

<210> SEQ ID NO 15
<211> LENGTH: 5
<212> TYPE: PRT
<213> ORGANISM: Homo sapiens

<400> SEQUENCE: 15

Arg Trp Gly Trp Arg
1               5
```

```
<210> SEQ ID NO 16
<211> LENGTH: 8
<212> TYPE: PRT
<213> ORGANISM: Homo sapiens

<400> SEQUENCE: 16

Arg Trp Gly Trp Arg His Gly Pro
1               5
```

NINJURIN-1 MODULATION AND USES THEREOF

CROSS REFERENCE TO RELATED APPLICATIONS

This application claims the benefit of U.S. provisional application Ser. No. 61/185,420, filed Jun. 9, 2009. This application also claims priority from Canadian patent application serial No. 2,676,962, and Australian patent application serial No. 2009212789, both filed Aug. 25, 2009. The contents of all these applications are incorporated herein by reference in their entirety.

SEQUENCE LISTING

Pursuant to 37 C.F.R. 1.821(c), a sequence listing is submitted herewith as an ASCII compliant text file named "Seq listing—12810.318_ST25", which was created on Jun. 8, 2010 and has a size of 13,500 bytes. The content of the aforementioned file named "Seq listing—12810.318_ST25" is hereby incorporated by reference in its entirety.

FIELD OF THE INVENTION

The present invention generally relates to neuroinflammation, and more particularly to the prevention, treatment and/or diagnosis of diseases and conditions associated with neuroinflammation such as multiple sclerosis (MS) and spinal cord injury (SCI).

BACKGROUND OF THE INVENTION

Neuroinflammatory conditions are a significant health concern. For example, multiple sclerosis (MS) is an immune-mediated inflammatory disorder of the central nervous system (CNS) characterized by multifocal areas of leukocyte infiltration, demyelination and axonal damage. Typically, demyelination is centered around pericapillary and periveinular accumulation of $CD4^+$ and $CD8^+$ memory T lymphocytes, macrophages and dendritic cells (DCs). These cells arise from migration of peripheral blood (PB) immune cells across the CNS microvascular endothelium.

There are few treatment regimens currently used in MS. Corticosteroids have anti-inflammatory and immunosuppressive effects, which also transiently restores the blood-brain barrier (Noseworthy et al., (2000) *Neurology* 54(9): 1726-33). They shorten the duration of the relapse and accelerate recovery. Since they are only effective as a short-term treatment, they are most commonly used to treat an acute relapse (Andersson and Goodkin, (1998) *J Neurol Sci.* 160(1): 16-25; Bansil et al., (1995) *Ann Neurol.* 37 Suppl 1: S87-101). Further, the responsiveness to corticosteroids declines over time, and extended use may lead to adrenal suppression, cardiovascular collapse and arrhythmias. (C. F. Lacy et al., *Drug information handbook* $8^{th}$ Edition, 2001, pp. 549-551).

Interferon (IFN)-β has been used as a therapy for patients with active Relapsing/Remitting Multiple Sclerosis (RRMS) since the 1980's. It is recently being used for secondary progressive patients as well. Recombinant IFN is available in 3 drugs: IFN-β-Ib (Betaseron™) and two IFNβ-Ia preparations (Avonex™ and Rebif™) (Polman and Uitedehaag, supra). These drugs reduce the rate of clinical relapse. However, neutralizing antibodies develop against these drugs rendering them ineffective with time. Also, flu-like symptoms are a prominent side effect early on in the treatment.

Glatiramer acetate (Copaxone™) is a synthetic co-polymer of tyrosine, glutamate, alanine and lysine, thought to mimic myelin basic protein (MBP) and thus, block T cell recognition of MBP (Karin N. et al., (1994) *J Exp Med.* 180(6): 2227-37). This drug is therefore beneficial in RRMS but not progressive MS. This drug also decreases the rate of relapse and appears to be better tolerated by patients than interferon therapy. Further, treatment with this drug may cause cardiovascular problems such as chest pain, flushing and tachycardia, and respiratory problems such as dyspnea (C. F. Lacy et al., supra).

Another drug that has been approved for the use in RRMS and secondary progressive MS is mitoxantrone. This drug is used to arrest the cell cycle and prevent cellular division, and it is primarily used in the treatment of leukemia (Rolak L. A., (2001) *Neurol Clin.* 19(1): 107-18). In MS, it reduces relapse rate and increases the length between exacerbations. This drug however has long-term side effects causing cardiac toxicity and chronic myeloid leukemias.

Therefore, there are a few moderately effective treatments for RRMS and secondary progressive MS that have shown to reduce both the frequency of the disease and severity of exacerbations.

Spinal cord injury (SCI) occurs due to traumatic injuries resulting from for example traffic accidents, sport accidents, or falls and drops from heights, and spinal cord compression, or the like. It also occurs due to other disorders, for example, when stroke is accompanied by pyramidal tract transection. Spinal cord injury results in permanent loss of motor, sensory and autonomic functions. Following the initial injury, presumably as part of the inflammatory/immune response to the injury, a series of degenerative processes which promote tissue damage beyond the original site of injury are initiated. After the initial mechanical disruption of nerves and nerve fibers at the time of injury, hemorrhaging is usually observed within 30 minutes at the area of damage and may expand over the next few hours. Within several hours following the injury, immune/inflammatory cells, e.g., neutrophils and macrophages, infiltrate the area and cause further damage to the nerve tissue, i.e., cell-mediated damage. These post-traumatic events are referred to as "secondary injury" (or "secondary spinal cord injury"). Therefore, a significant aspect of the tissue damage and functional loss may be preventable as it is the result of secondary events triggered by the trauma. It is important to treat as promptly as possible when the spinal cord is damaged, in order to promote recovery from or to prevent progress, of neurologic function deficit. It would be advantageous to prevent further damage to the spinal cord and surrounding tissue following a spinal cord injury by treatment as soon as possible after the initial trauma to prevent secondary injury effects.

Currently, the conventional treatment for reducing or minimizing the damage resulting from secondary injury is intravenous injection of the glucocorticoid, methylprednisolone (Bracken et al., *JAMA,* 277(20): 1597-1604 (1997)). Unfortunately, prolonged administration of glucocorticoids has adverse systemic side effects, e.g., increased incidence of sepsis and pneumonia, and a limited therapeutic window. Furthermore, recent studies have raised doubts about the beneficial effects of high doses methylprednisolone after SCI (Schröter et al., *Neuroscience* 2009 161(3): 753-63. Epub 2009 Apr. 11).

There is therefore a continued need for improved materials and methods for the treatment of conditions/diseases associated with neuroinflammation, such as MS and SCI.

The present description refers to a number of documents, the content of which is herein incorporated by reference in their entirety.

SUMMARY OF THE INVENTION

The present invention generally relates to neuroinflammation, and more particularly to the prevention, treatment and/or diagnosis of diseases and conditions associated with neuroinflammation, such as multiple sclerosis (MS) and spinal cord injury (SCI).

More specifically, in accordance with a first aspect of the present invention, there is provided a method of preventing or treating a neuroinflammatory condition in a subject, said method comprising administering to said subject an effective amount of a nerve injurin-induced protein-1 (Ninjurin-1) inhibitor.

In another aspect, the present invention provides a method of inhibiting the recruitment of a myeloid cell across the CNS endothelium comprising contacting said myeloid cell and/or said CNS endothelium with an effective amount of a Ninjurin-1 inhibitor.

In another aspect, the present invention provides a use of a Ninjurin-1 inhibitor for preventing or treating a neuroinflammatory condition in a subject. In another aspect, the present invention provides a use of a Ninjurin-1 inhibitor for the preparation of a medicament for preventing or treating a neuroinflammatory condition in a subject.

In another aspect, the present invention provides a use of a Ninjurin-1 inhibitor for inhibiting the recruitment of a myeloid cell across the CNS endothelium. In another aspect, the present invention provides a use of a Ninjurin-1 inhibitor for the preparation of a medicament for inhibiting the recruitment of a myeloid cell across the CNS endothelium.

In another aspect, the present invention provides a Ninjurin-1 inhibitor for preventing or treating a neuroinflammatory condition in a subject. In another aspect, the present invention provides a Ninjurin-1 inhibitor for the preparation of a medicament for preventing or treating a neuroinflammatory condition in a subject.

In another aspect, the present invention provides a Ninjurin-1 inhibitor for inhibiting the recruitment of a myeloid cell across the CNS endothelium. In another aspect, the present invention provides a Ninjurin-1 inhibitor for the preparation of a medicament for inhibiting the recruitment of a myeloid cell across the CNS endothelium.

In another aspect, the present invention provides a pharmaceutical composition for (i) preventing or treating a neuroinflammatory condition in a subject or (ii) inhibiting the recruitment of a myeloid cell across the CNS endothelium, said composition comprising a Ninjurin-1 inhibitor and a pharmaceutically acceptable carrier.

In an embodiment, the above-mentioned Ninjurin-1 inhibitor blocks Ninjurin-1/Ninjurin-1 homotypic interaction.

In an embodiment, the above-mentioned Ninjurin-1 inhibitor binds to an extracellular domain of a Ninjurin-1 polypeptide. In a further embodiment, the above-mentioned Ninjurin-1 inhibitor binds to a domain comprising a motif corresponding to residues 28 to 35 of a Ninjurin-1 polypeptide.

In an embodiment, the above-mentioned Ninjurin-1 polypeptide is a human Ninjurin-1 polypeptide.

In an embodiment, the above-mentioned Ninjurin-1 inhibitor is a peptide comprising a domain of formula I (SEQ ID NO: 13):

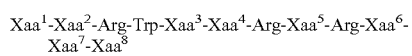

(I), wherein $Xaa^1$, $Xaa^2$, $Xaa^6$, $Xaa^7$ and $Xaa^8$ is each independently any amino acid or is absent;

$Xaa^3$, $Xaa^4$ and $Xaa^5$ is each independently any amino acid;

or a functional analog thereof.

In an embodiment, $Xaa^2$ is Pro. In an embodiment, $Xaa^1$ is Pro. In an embodiment, $Xaa^6$ is Pro. In an embodiment, $Xaa^7$ is Ile. In an embodiment, $Xaa^8$ is Asn. In an embodiment, $Xaa^3$ is Gly. In an embodiment, $Xaa^4$ is Leu. In an embodiment, $Xaa^5$ is Asn or Leu.

In an embodiment, the above-mentioned domain is Pro-Pro-Arg-Trp-Gly-Leu-Arg-Asn-Arg-Pro-Ile-Asn (SEQ ID NO: 6).

In another embodiment, the above-mentioned Ninjurin-1 inhibitor is a peptide comprising a domain of formula II (SEQ ID NO: 14):

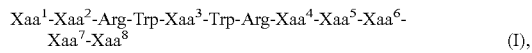

wherein $Xaa^1$, $Xaa^2$, $Xaa^4$ and $Xaa^5$, $Xaa^6$, $Xaa^7$ and $Xaa^8$ is each independently any amino acid or is absent;

$Xaa^3$ is any amino acid;

or a functional analog thereof.

In an embodiment, $Xaa^1$ is Pro. In an embodiment, $Xaa^2$ is Ala. In an embodiment, $Xaa^3$ is Gly. In an embodiment, $Xaa^4$ is His. In an embodiment, $Xaa^5$ is Gly. In an embodiment, $Xaa^6$ is Pro. In an embodiment, $Xaa^7$ is Ile. In an embodiment, $Xaa^8$ is Asn.

The method of claim 7, wherein said domain is Pro-Ala-Arg-Trp-Gly-Trp-Arg-His-Gly-Pro-Ile-Asn (SEQ ID NO: 5).

In another embodiment, the above-mentioned Ninjurin-1 inhibitor is a peptide consisting of the domain of formula I or II defined above.

In another aspect, the present invention provides a method of identifying a compound for preventing or treating a neuroinflammatory condition, said method comprising determining whether: (a) a level of expression of a Ninjurin-1 nucleic acid or encoded polypeptide; (b) a level of Ninjurin-1 activity; or (c) a combination of (a) and (b); is decreased in the presence of a test compound relative to in the absence of said test compound; wherein said decrease is indicative that said test compound may be used for preventing or treating said neuroinflammatory condition.

In another aspect, the present invention provides method of identifying or characterizing a compound for preventing or treating a neuroinflammatory condition, said method comprising: (a) contacting a test compound with a cell comprising a first nucleic acid comprising a transcriptionally regulatory element normally associated with a Ninjurin-1 gene, operably linked to a second nucleic acid comprising a reporter gene capable of encoding a reporter protein; and (b) determining whether reporter gene expression or reporter protein activity is decreased in the presence of said test compound relative to in the absence of said test compound; wherein a decrease in said reporter gene expression or reporter protein activity is indicative that said test compound may be used for preventing or treating said neuroinflammatory condition.

In another aspect, the present invention provides a method of identifying a compound for inhibiting the recruitment of a myeloid cell across the CNS endothelium, said method comprising determining whether: (a) a level of expression of a Ninjurin-1 nucleic acid or encoded polypeptide; (b) a level of Ninjurin-1 activity; or (c) a combination of (a) and (b); is decreased in the presence of a test compound relative to in the absence of said test compound; wherein said decrease is indicative that said test compound may be used for inhibiting the recruitment of a myeloid cell across the CNS endothelium.

In another aspect, the present invention provides a method of identifying or characterizing a compound for inhibiting the recruitment of a myeloid cell across the CNS endothelium, said method comprising: (a) contacting a test compound with a cell comprising a first nucleic acid comprising a transcriptionally regulatory element normally associated with a Ninjurin-1 gene, operably linked to a second nucleic acid comprising a reporter gene capable of encoding a reporter protein; and (b) determining whether reporter gene expression or reporter protein activity is decreased in the presence of said test compound relative to in the absence of said test compound; wherein a decrease in said reporter gene expression or reporter protein activity is indicative that said test compound may be used for inhibiting the recruitment of a myeloid cell across the CNS endothelium.

In another aspect, the present invention provides a method for diagnosing a neuroinflammatory condition in a first subject, said method comprising (a) determining the expression and/or activity of Ninjurin-1 in a sample from said first subject (b) comparing said expression and/or activity to a corresponding reference expression and/or activity; and (c) diagnosing said neuroinflammatory condition based on said comparison.

In an embodiment, the above-mentioned reference expression and/or activity corresponds to an expression and/or activity determined in a sample from a control subject known to not having a neuroinflammatory condition, and wherein a higher expression and/or activity in said sample from said first subject is indicative that said first subject has a neuroinflammatory condition.

In another embodiment, the above-mentioned reference expression and/or activity corresponds to an expression and/or activity determined in a sample from a control subject known to have a neuroinflammatory condition, and wherein a comparable or higher expression and/or activity in said sample from said first subject is indicative that said first subject has neuroinflammatory condition.

In another aspect, the present invention provides a method for monitoring the course of treatment of a patient suffering from a neuroinflammatory condition, the method comprising (a) determining the expression and/or activity of Ninjurin-1 in a sample from said patient; wherein a decrease in said expression and/or activity relative to a corresponding expression and/or activity of Ninjurin-1 determined in a biological sample obtained from said patient at an earlier time is indicative that said patient is responsive to said treatment.

In an embodiment, the above-mentioned neuroinflammatory condition is associated with recruitment of a myeloid cell to the central nervous system (CNS). In a further embodiment, the above-mentioned myeloid cell is a monocyte, a macrophage and/or a dendritic cell.

In an embodiment, the above-mentioned neuroinflammatory condition is associated with a CNS trauma. In a further embodiment, the above-mentioned CNS trauma is spinal cord injury (SCI).

In another embodiment, the above-mentioned neuroinflammatory condition is an autoimmune CNS condition. In a further embodiment, the above-mentioned autoimmune CNS condition is multiple sclerosis (MS).

In an embodiment, the above-mentioned method further comprises, or the above-mentioned agent or composition is further for: (i) reducing the neurological signs, symptoms and/or clinical scores of the neuroinflammatory condition; (ii) reducing tissue damage; and/or (iii) reducing infiltration of myeloid cells into the CNS.

In an embodiment, the above-mentioned CNS endothelium is exposed to an inflammatory environment. In a further embodiment, the above-mentioned inflammatory environment comprises Interferon-gamma (IFN-γ) and/or Tumor Necrosis Factor-alpha (TNF-α).

In another embodiment, the above-mentioned inflammatory environment is associated with the above-mentioned neuroinflammatory condition.

In an embodiment, the above-mentioned sample is a CNS cell or tissue.

In another embodiment, the above-mentioned sample is a blood cell sample. In a further embodiment, the above-mentioned blood cell sample is a peripheral blood mononuclear cell (PBMC) sample.

In an embodiment, the above-mentioned sample comprises myeloid cells. In a further embodiment, the above-mentioned myeloid cells are (i) monocytes; (ii) macrophages, (iii) dendritic cells or (iv) any combination of (i) to (iii).

In an embodiment, the above-mentioned expression and/or activity of Ninjurin-1 is determined by measuring the relative amount of Ninjurin-1-expressing cells in said sample.

Other objects, advantages and features of the present invention will become more apparent upon reading of the following non-restrictive description of specific embodiments thereof, given by way of example only with reference to the accompanying drawings.

BRIEF DESCRIPTION OF THE DRAWINGS

In the appended drawings:

FIG. 1A: Flow cytometry analysis of the expression of Ninjurin-1 in resting human primary BBB-ECs (left panel) treated with astrocyte conditioned media (ACM) (40%, 24 h) (center panel) or treated with pro-inflammatory cytokines TNF+IFN-γ (100 U/ml, 24 h) in the presence of ACM (right panel). Data shown are representative of ten independent experiments. FIG. 1B: Ninjurin-1 immunostaining of resting or activated BBB-ECs. Confocal microscopy confirmed Ninjurin-1 (green) expression at the surface of BBB-ECs and up-regulation following treatment with TNF and IFN-γ (100 U/ml, 16 h). TO-PRO-3 was used for nuclear staining. Scale bar: 10 μm. Data shown are representative of three independent experiments;

FIG. 2A: Flow cytometry analysis of Ninjurin-1 expression on ex vivo human peripheral blood lymphocytes ($CD4^+$, $CD8^+$, $CD19^+$) demonstrates low levels on T and B lymphocytes. FIG. 2B: Flow cytometry analysis of Ninjurin-1 expression on human ex vivo $CD14^+$ monocytes, and in vitro $CD68^+$ macrophages and $CD83^+$ dendritic cells (DCs) demonstrates high expression of Ninjurin-1 on myeloid antigen-presenting cells. FIG. 2C: Western blot (WB) analysis of Ninjurin-1 in ex vivo human leukocytes ($CD8^+$, $CD4^+$, $CD19^+$ and $CD14^+$). Ninjurin-1 is preferentially expressed in $CD14^+$ monocytes. FIG. 2D: Expression of Ninjurin-1 on human $CD68^+$ microglia grown in primary cultures. Data shown are representative of seven (A), five (C), and two (B and D) independent experiments using an equivalent number of preparations and donors. Isotype controls are shown in clear histograms and Ninjurin-1 immunostaining in gray;

FIG. 3A: Ninjurin-1 immunostaining in normal-appearing white matter (NAWM) blood vessels of human CNS post-mortem sections (left panel). Ninjurin-1 expression on infiltrating immune cells and on ECs in MS lesions (right panel). Arrowheads show Ninjurin-1-expressing ECs. Scale bars, 50 µm. FIG. 3B: Percentage of $CD14^+$ monocytes and $CD11c^+$ myeloid cells co-expressing Ninjurin-1 in the cerebrospinal fluid (CSF) and the peripheral blood of MS patients (n=5). Mean±SEM from five independent experiments. FIG. 3C: Co-expression of Ninjurin-1 and Caveolin-1 on ECs within NAWM from MS patients. Scale bar, 30 µm.

FIG. 4A: Western blot for Ninjurin-1 in spinal cord homogenates of myelin oligodendrocyte glycoprotein $(MOG)_{35-55}$-immunized EAE mice (C57BL/6) revealed an upregulation of Ninjurin-1 compared to the control. Levels of Ninjurin-1 correlated with EAE scores (center lane, presymptomatic (PS): score 1; right lane, peak: score 2.5). FIG. 4B: Flow cytometry analysis of Ninjurin-1 expression on MHC $II^+$ (left panel) $CD11c^+$ DCs (middle panel) and $F4/80^+$ macrophages (right panel) obtained from the CNS (brain and spinal cord) of $MOG_{35-55}$-immunized EAE mice (C57BL/6). Data shown are representative of two experiments, gated on $CD3^{neg}$ $CD45^{hi}$ and either MHC II-(left panel), CD11c- (middle panel) or F4/80- (right panel) expressing cells. FIG. 4C: Spinal cords from EAE mice immunostained for Ninjurin-1, MHC II (left panels), CD11c (middle panels), F4/80 (right panels) and nuclear stain TO-PRO-3 (day 14 post-induction, n=6). High power view of areas marked confirmed co-localization of Ninjurin-1 in CNS myeloid antigen-presenting cells (red). Scale bars, 30 µm. FIG. 4D: Western blot for Ninjurin-1 in spinal cord homogenates after SCI in C57BL/6 mice. Spinal cord mechanical injury was performed in mice using the Infinite Horizons™ impactor device. Samples were extracted from uninjured (UI) and from injured mice 1, 3, 7, 14, 21 and 28 days after injury. The expression of Ninjurin-1 increases in the spinal cord of injured mice;

FIG. 5A: In vitro model of the BBB. Human BBB-endothelial cells are grown in Boyden chambers and treated with the Ninjurin-1 blocking peptide $Ninj_{26-37}$ (top chamber) 1 hour prior to the addition of immune cells. FIGS. 5B and C: Human ex vivo $CD4^+$ and $CD8^+$ T lymphocytes (B) and $CD14^+$ monocytes (C) were allowed to migrate across human BBB-endothelial cells for 24 h, in the presence of the human $Ninj_{26-37}$ blocking peptide or a scramble peptide (control). Ninjurin-1 blockade (0.4 mM) significantly restricts the migration of $CD14^+$ monocyte, but not that of $CD4^+$ or $CD8^+$ T cells, across human BBB-endothelial cells. Data shown are representative of seven independent experiments (n=7 blood donors) on six distinct BBB-EC preparations performed in triplicate. FIG. 5D: CFSE-labeled human $CD14^+$ monocytes (green) were seeded on a confluent monolayer of human TNF/IFN-γ-activated BBB-ECs, fixed and immunostained for Ninjurin-1 (left panels). A 15 µm z-stack reconstruction (x-z and y-z) shows Ninjurin-1 (arrows) around the CFSE-loaded migrating monocyte and in the transmigratory cup (arrowheads). Photomicrograph shown is representative of >20 fields obtained from four independent immunostainings performed using four blood donors and two distinct BBB-ECs preparations. Scale bar, 20 µm;

FIG. 6A: Mice treated with $Ninj_{26-37}$ blocking peptide show a significant reduction of the neurological signs, symptoms and clinical scores of the disease. (clinical score: 0=no clinical symptoms; 0.5=partial floppy tail; 1=floppy tail; 2=ataxia; 2.5=weakness of hind limbs; 3=paralysis of one hind limb; 4=paralysis of both hind limbs). FIG. 6B: Flow cytometry analysis of CNS infiltrating leukocytes 14 days postimmunization, comparing the number of $CD3^+$ lymphocytes, $CD11c^+$ DCs (top panels) and $F4/80^+$ macrophages (lower panels) in $Ninj_{26-37}$-treated mice vs. control animals. Data shown are representative of two independent experiments obtained from four mice, gated on $CD45^{hi}$ cells. FIG. 6C: Luxol fast blue-hematoxylin and eosin stainings of EAE spinal cords from $Ninj_{26-37}$-treated mice show a reduction in immune cell infiltration and demyelination, as compared to the control group. Photomicrographs shown are representative of >20 stainings performed on four animals. Dotted lines delineate areas of demyelination. Scale bar, 50 µm. FIG. 6D: Immunofluorescent analyses of spinal cords (14 days post-immunization) confirmed reduction of infiltrating MHC $II^+$ (top panels), $F4/80^+$ (middle panels) and $CD11c^+$ (bottom panels) cells in $Ninj_{26-37}$-treated mice vs. control animals. Nuclei were stained with TO-PRO-3. Photomicrographs shown are representative of >20 immunostainings performed on post-mortem material from 4 animals. Scale bar, 30 µm;

FIGS. 7A-D show the clinical effect of Ninjurin-1 blocking peptide after spinal cord injury. Spinal cord mechanical injury was performed in C57BL/6 mice using the Infinite Horizons™ impactor device. FIG. 7A: Western Blot of spinal cords samples showing Ninjurin-1 expression at day 1, 3, 7, 14, 21 and 28 post-injury. Ctl represents baseline (uninjured) control. Data shown are representative of two experiments performed with three animals. FIGS. 7B and C: Immunostainings and cell counts of $Iba1^+$ and $CD11c^+$ myeloid cell infiltrates in the spinal cord of SCI animals treated with $Ninj_{26-37}$ blocking peptide (200 µg i.p., twice a day) vs. controls. Photomicrographs shown are representative of immunostainings obtained from control and $Ninj_{26-37}$-treated animals mice (n=4 per group, day 7 post-injury). Scale bars, 500 µm. FIG. 7D: The clinical scores (Basso mouse scale, BMS, Basso D. M. et al., (2006). *J Neurotrauma.* 23(5): 635-59) of mice treated with $Ninj_{26-37}$ blocking peptide (●, 200 µg i.p., twice a day) were reduced when compared to control animals (○). Data shown represent two independent experiments using 11 mice per group;

FIGS. 8A-D show the nucleotide and amino acid sequences of Ninjurin-1. FIG. 8A: Nucleotide sequence of human Ninjurin-1 (SEQ ID NO: 1, NCBI Reference Sequence: NM_004148.3). The coding sequence (residues 70 to 530) is indicated in bold. FIG. 8B: Amino acid sequence of human Ninjurin-1 (SEQ ID NO: 2, NCBI Reference Sequence: NP_004139.2). FIG. 8C: Nucleotide sequence of mouse Ninjurin-1 (SEQ ID NO: 3, NCBI Reference Sequence: NM_013610.2). The coding sequence (residues 17 to 475) is indicated in bold. FIG. 8D: Amino acid sequence of mouse Ninjurin-1 (SEQ ID NO: 4, NCBI Reference Sequence: NP_038638.1);

FIG. 13A: Memory $CD4^+$ $CD45RO^+$ T lymphocytes loaded with vital dye Carboxyfluorescein succinimidyl ester (CFSE) were cultured for 6 days with $CD14^+$ monocytes (ratio of 2 T cells for 1 monocyte)+hemagglutinin $(HA)_{306-318}$ peptide in the presence of isotype control (sheep IgG) or sheep anti-human Ninjurin-1 blocking antibody (Ab) (10 µg/ml). Proliferation was assessed by flow cytometry. No difference in proliferation was detected between isotype control (left panel) and Ninjurin-1 Ab condition (right panel). Data shown are representative of 3 independent experiments performed with the blood of healthy donors (n=3). FIGS. 13B and C: Spleen and lymph node cells collected from EAE mice 7 days post-induction were loaded with CFSE and cultured for 2 days with $MOG_{35-55}$, recombinant mouse IL-12 (2.5 ng/ml), recombinant mouse IL-23 (20 ng/ml) in the presence of (B) anti-Ninjurin-1 blocking Ab (or isotype control, 10 µg/ml) or (C) $Ninj_{26-37}$ blocking peptide (or scramble 0.4 mM). Gating was done on $CD3^+$ $CD4^+$ cells and proliferation was assessed by flow cytometry. No difference in proliferation was detected between the Ninjurin-1 blocking groups and control groups. Data shown are representative of three independent experiments (n=3);

FIG. 16 shows the effect of Ninjurin-1 blockade on EAE severity. C57BL/6 animals immunized with $MOG_{35-55}$/CFA were injected intraperitoneally on day 4, 6, 8 and 10 post-immunization with 150 µg of anti-Ninjurin-1 blocking antibody (Ab) or corresponding isotype control. For experiments with the peptides, mice were injected twice daily with 200 µg of scramble or $Ninj_{26-37}$ blocking peptide, from day 3 to day 23 post-immunization. Data represent the number of animals with clinical scores ≥3.0 from day 11 to 17 post-immunization over the total number of mice per group. *P<0.05;

FIG. 18A: Anti-Ninjurin-1 blocking antibody (Ab) or isotype control (each 150 μg per injection per mouse) were injected intraperitoneally (i.p.) on day 4, 6, 8 and 10 post-induction (n=8 mice).

DESCRIPTION OF ILLUSTRATIVE EMBODIMENTS

Figure 1A:
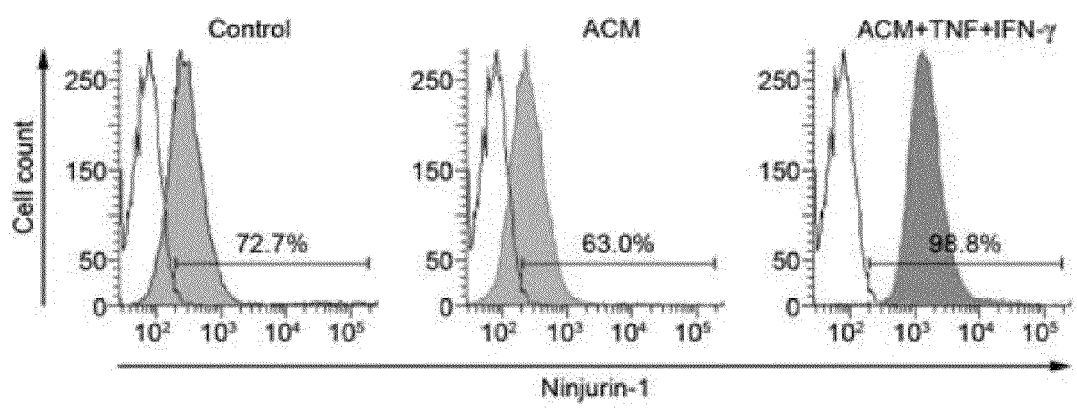
FIGS. 1A-B show the expression of nerve injury-induced protein-1 (Ninjurin-1) in vitro in human blood-brain barrier (BBB)-endothelial cells.

In the studies described herein, the expression of nerve injury-induced protein-1 (Ninjurin-1) on brain and spinal cord endothelial cells (ECs) and on peripheral blood monocytes, as well as its ability to promote myeloid cell recruitment across the BBB, was investigated. The instant inventors have determined that while Ninjurin-1 is expressed at low levels in healthy human and mouse CNS, its immunoreactivity is localized to CNS microvascular endothelium, as well as on microglia, infiltrating macrophages and dendritic cells during neuroinflammatory events. In the peripheral blood, Ninjurin-1 expression was found predominantly on human $CD14^+$ monocytes, but not on the surface of $CD4^+$ or $CD8^+$ T lymphocytes. Using a blocking oligopeptide corresponding to residue 26 to 37 of Ninjurin-1 ($Ninj_{26-37}$) and/or a blocking anti-Ninjurin-1 antibody, it was further demonstrated that Ninjurin-1 significantly contributes to monocyte recruitment/migration into the CNS in vitro and in vivo during EAE and SCI, and that Ninjurin-1 neutralization reduces neuroinflammation, protects against EAE and promotes repair following SCI.

Accordingly, in an aspect, the present invention provides a method of preventing or treating a neuroinflammatory condition in a subject in need thereof, said method comprising administering to said subject in need thereof an effective amount of a Ninjurin-1 inhibitor.

In another aspect, the present invention provides a method of inhibiting the recruitment of a myeloid cell across the CNS endothelium, said method comprising contacting said myeloid cell and/or said CNS endothelium with an effective amount of a Ninjurin-1 inhibitor.

In another aspect, the present invention provides a use of a Ninjurin-1 inhibitor for preventing or treating a neuroinflammatory condition in a subject. The present invention also relates to a use of a Ninjurin-1 inhibitor for the preparation of a medicament for preventing or treating a neuroinflammatory condition in a subject.

In another aspect, the present invention provides a use of a Ninjurin-1 inhibitor for inhibiting the recruitment of a myeloid cell across the CNS endothelium. The present invention also relates to a use of a Ninjurin-1 inhibitor for the preparation of a medicament for inhibiting the recruitment of a myeloid cell across the CNS endothelium.

In another aspect, the present invention provides a Ninjurin-1 inhibitor for preventing or treating a neuroinflammatory condition in a subject. The present invention further relates to a Ninjurin-1 inhibitor for the preparation of a medicament for preventing or treating a neuroinflammatory condition in a subject.

In another aspect, the present invention provides a Ninjurin-1 inhibitor for inhibiting the recruitment of a myeloid cell across the CNS endothelium. The present invention further relates to a Ninjurin-1 inhibitor for the preparation of a medicament for inhibiting the recruitment of a myeloid cell across the CNS endothelium.

Ninjurin-1 (also known as NIN1 or NINJ1) is a type 3b membrane protein known to interact in a homophilic manner through an extracellular binding motif. The nucleotide and amino acid sequences of human and mouse Ninjurin-1 are illustrated in FIGS. 8A-D. While Ninjurin-1 is expressed during embryogenesis and is thought to contribute to CNS and peripheral nervous system (PNS) development, its expression is strikingly up-regulated on neurons and Schwann cells during experimental peripheral nerve injury. In rats, functional inhibition of Ninjurin-1/Ninjurin-1 homotypic interaction using the blocking oligopeptide ($Ninj_{26-37}$) was shown to reduce post-lesional neurite outgrowth, suggesting a positive influence of Ninjurin-1 on nerve regeneration.

"Neuroinflammatory condition" as used herein refers to a condition associated with inflammation of the nervous system, and more particularly the central nervous system (CNS), and which is associated with cell/tissue damage. It is typically characterized by, for example, increased glial activation, increased pro-inflammatory cytokine/chemokine levels (e.g., TNF-α, IFN-γ, IL-1β), increased blood-brain-barrier permeability, and/or increased immune cell (e.g., leukocyte) recruitment/invasion to the CNS. It includes chronic neuroinflammation, such as an inflammation associated with chronic activation of cells of the immune system (i.e., autoimmune-associated neuroinflammation). Such chronic neuroinflammation is observed, for example, in multiple sclerosis. It also include acute neuroinflammation, such as inflammation resulting from an initial trauma to the CNS. Acute neuroinflammation is observed, for example, following CNS injury (e.g., spinal cord injury), and is associated with CNS tissue damage beyond the original site of injury.

In an embodiment, the above-mentioned neuroinflammatory condition is multiple sclerosis (MS). In a further embodiment, the above-mentioned MS is of one of the following subtypes: clinically isolated syndromes (CIS) suggestive of MS, relapsing-remitting MS, primary progressive MS, secondary progressive MS, progressive relapsing MS, or borderline forms of MS (e.g., Devic's disease, Balo concentric sclerosis, Schilder's diffuse sclerosis, Marburg multiple sclerosis), as well as any neurological diseases with signs and symptoms suggestive of MS.

In another embodiment, the above-mentioned neuroinflammatory condition is spinal cord injury, in a further embodiment secondary spinal cord injury.

An "effective amount" refers to an amount effective, at dosages and for periods of time necessary, to achieve the desired prophylactic or therapeutic result. An effective amount refers to the amount of active compound or pharmaceutical agent that elicits the biological or medicinal response in a tissue, system, animal, individual or human that is being sought by a researcher, veterinarian, medical doctor or other clinician, which includes one or more of the following:

(A) Preventing the disease; for example, preventing a neuroinflammatory disease, condition or disorder in an individual that may be predisposed to the disease, condition or disorder but does not yet experience or display the pathology or symptomatology of the disease, (B) Inhibiting the disease; for example, inhibiting a neuroinflammatory disease, condition or disorder in an individual that is experiencing or displaying the pathology or symptomatology of the disease, condition or disorder (i.e., arresting further development of the pathology and/or symptomatology), and (C) Ameliorating the disease; for example, ameliorating a neuroinflammatory disease, condition or disorder in an individual that is experiencing or displaying the pathology or symptomatology of the disease, condition or disorder (i.e., reversing the pathology and/or symptomatology).

The amount of the Ninjurin-1 inhibitor which is effective in the prevention and/or treatment of a particular disease, disorder or condition (e.g., a neuroinflammatory disease, disorder or condition) will depend on the nature and severity of the disease, the chosen prophylactic/therapeutic regimen, the target site of action, the patient's weight, special diets being followed by the patient, concurrent medications being used, the administration route and other factors that will be recognized by those skilled in the art. The dosage will be adapted by the clinician in accordance with conventional factors such as the extent of the disease and different parameters from the patient. Typically, 0.001 to 1000 mg/kg of body weight/day will be administered to the subject. In an embodiment, a daily dose range of about 0.01 mg/kg to about 500 mg/kg, in a further embodiment of about 0.1 mg/kg to about 200 mg/kg, in a further embodiment of about 1 mg/kg to about 100 mg/kg, in a further embodiment of about 10 mg/kg to about 50 mg/kg, may be used. The dose administered to a patient, in the context of the present invention should be sufficient to effect/induce a beneficial prophylactic and/or therapeutic response in the patient over time. The size of the dose also will be determined by the existence, nature, and extent of any adverse side-effects that accompany the administration. Effective doses may be extrapolated from dose response curves derived from in vitro or animal model test systems. For example, in order to obtain an effective mg/kg dose for humans based on data generated from rat studies, the effective mg/kg dosage in rat may be divided by six.

In an embodiment, the above-mentioned treatment comprises the use/administration of more than one (i.e. a combination of) active/therapeutic agent, including the above-mentioned Ninjurin-1 inhibitor. The combination of prophylactic/therapeutic agents and/or compositions of the present invention may be administered or co-administered (e.g., consecutively, simultaneously, at different times) in any conventional dosage form. Co-administration in the context of the present invention refers to the administration of more than one therapeutic in the course of a coordinated treatment to achieve an improved clinical outcome. Such co-administration may also be coextensive, that is, occurring during overlapping periods of time. For example, a first agent may be administered to a patient before, concomitantly, before and after, or after a second active agent is administered. The agents may in an embodiment be combined/formulated in a single composition and thus administered at the same time. In an embodiment, the one or more active agent(s) is used/administered in combination with one or more agent(s) currently used to prevent or treat the disorder in question (e.g., a neuroinflammatory condition such as MS or SCI).

As used herein, the term "Ninjurin inhibitor" includes any compound able to directly or indirectly affect the regulation of Ninjurin-1 by reducing for example the expression of Ninjurin-1 (i.e., transcription and/or the translation), or a Ninjurin-1 activity. It includes intracellular as well as extracellular Ninjurin-1 inhibitors. Without being so limited, such inhibitors include siRNA, antisense molecules, proteins, peptides, small molecules, antibodies, etc.

As used herein the terms "Ninjurin-1 activity" and "Ninjurin-1 function" refer to detectable enzymatic, biochemical or cellular activity attributable to Ninjurin-1. Ninjurin-1 activity may also be measured by protein-protein binding assay using purified Ninjurin-1 and a purified Ninjurin-1 ligand (e.g., Ninjurin-1). As such, in an embodiment, determining whether a compound decreases Ninjurin-1 activity comprises determining whether the compound inhibits or decreases Ninjurin-1-Ninjurin-1 homotypic binding. In an embodiment, such a binding assay may be performed using cells expressing Ninjurin-1 on their surface, thus via measurement of cell-cell binding of such Ninjurin-1-positive cells. Ninjurin-1 activity may also be measured in a cell recruitment/migration assay, such as the assay described in Example 4 below, or using a Ninjurin-mediated adhesion assay, as described for example in Araki et al., *J. Biol Chem.* 1997 272(34) 21373-21380 and in U.S. Pat. No. 6,559,288).

Ninjurin-1 activity could also be indirectly measured by evaluating the level of expression of Ninjurin-1, or a fragment thereof, in cells as well as in a biological sample (tissue, organ, fluid). Ninjurin-1 expression levels could be determined at the polypeptide and/or nucleic acid levels using any standard methods known in the art (see below). Ninjurin-1 activity could also be indirectly measured by evaluating the level of expression or activity of a reporter gene (e.g., luciferase, β-galactosidase, alkaline phosphatase, GFP) operably linked to a transcriptionally regulatory element normally associated with a Ninjurin-1 gene.

In an embodiment, the above-mentioned Ninjurin-1 inhibitor is an antisense or RNAi-based inhibitory molecule.

Generally, the principle behind antisense technology is that an antisense molecule hybridizes to a target nucleic acid and effects modulation of gene expression such as transcription, splicing, translocation of the RNA to the site of protein translation, translation of protein from the RNA. The modulation of gene expression can be achieved by, for example, target degradation or occupancy-based inhibition. An example of modulation of RNA target function by degradation is RNase H-based degradation of the target RNA upon hybridization with a DNA-like antisense compound. Another example of modulation of gene expression by target degradation is RNA interference (RNAi). RNAi is a form of antisense-mediated gene silencing involving the introduction of dsRNA (typically of less than 30 nucleotides in length, and generally about 19 to 24 nucleotides in length) leading to the sequence-specific reduction of targeted endogenous mRNA levels, here the RNA transcript of the Ninjurin-1 gene. Such dsRNA are generally substantially complementary to at least part of an RNA transcript of the Ninjurin-1 gene. Another example of modulation of gene expression is the RNA analogue Locked Nucleic Acid (LNA). Other examples relate to double stranded nucleic acid molecules including small nucleic acid molecules, such as short interfering nucleic acid (siNA), short interfering RNA (sRNA), micro-RNA (miRNA). The use of single stranded antisense oligonucleotides (ASO) is also encompassed by the method of the present invention. Sequence-specificity makes antisense compounds extremely attractive as therapeutics to selectively modulate the expression of genes involved in the pathogenesis of any one of a variety of diseases.

Chemically modified nucleosides, such as 2'-substituted arabinonucleosides (e.g., 2'F-ANA) and 2'-substituted RNA (e.g., 2'F-RNA), may be used for incorporation into antisense compounds to enhance one or more properties, such as nuclease resistance, pharmacokinetics or affinity for a target RNA.

As used herein "antisense molecule" is meant to refer to an oligomeric molecule, particularly an antisense oligonucleotide for use in modulating the activity or function of nucleic acid molecules encoding a Ninjurin-1 polypeptide (e.g., the polypeptide of SEQ ID NO: 2), ultimately modulating the amount of Ninjurin-1 produced in cells (e.g., CNS cells, immune cells). This is accomplished by providing oligonucleotide molecules which specifically hybridize with one or more nucleic acids encoding Ninjurin-1. As used herein, the term "nucleic acid encoding a Ninjurin-1 polypeptide" encompasses DNA encoding said polypeptide, RNA (including pre-mRNA and mRNA) transcribed from such DNA, and also cDNA derived from such RNA (e.g., a nucleic acid comprising the coding sequence of the nucleotide sequence set forth in SEQ ID NO: 1). The specific hybridization of an oligomeric compound with its target nucleic acid interferes with the normal function of the nucleic acid. The overall effect of such interference with target nucleic acid function is modulation of the expression of Ninjurin-1. In the context of the present invention, "modulation" means either an increase (stimulation) or a decrease (inhibition) in the expression of a gene.

In the context of this invention, "hybridization" means hydrogen bonding between complementary nucleoside or nucleotide bases. Terms "specifically hybridizable" and "complementary" are the terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of utility, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed. Such conditions may comprise, for example, 400 mM NaCl, 40 mM PIPES pH 6.4, 1 mM EDTA, at 50 to 70° C. for 12 to 16 hours, followed by washing. The skilled person will be able to determine the set of conditions most appropriate for a test of complementarity of two sequences in accordance with the ultimate application of the hybridized nucleotides.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases. Examples of modified nucleotides include a 2'-O-methyl modified nucleotide, a nucleotide comprising a 5'-phosphorothioate group, a terminal nucleotide linked to a cholesteryl derivative, a 2'-deoxy-2'-fluoro modified nucleotide, a 2'-deoxy-modified nucleotide, a locked nucleotide, an abasic nucleotide, a 2'-amino-modified nucleotide, a 2'-alkyl-modified nucleotide, a morpholino nucleotide, a phosphoramidate and a non-natural base comprising nucleotide.

Methods to produce antisense molecules directed against a nucleic acid are well known in the art. The antisense molecules of the invention may be synthesized in vitro or in vivo.

Reagents and kits for performing RNAi are available commercially from for example Ambion Inc. (Austin, Tex., USA), New England Biolabs Inc. (Beverly, Mass., USA) and Invitrogen (Carlsbad, Calif., USA).

The antisense molecule may be expressed from recombinant viral vectors, such as vectors derived from adenoviruses, adeno-associated viruses, retroviruses, herpesviruses, and the like. Such vectors typically comprises a sequence encoding an antisense molecule of interest (e.g., a dsRNA specific for Ninjurin-1) and a suitable promoter operatively linked to the antisense molecule for expressing the antisense molecule. The vector may also comprise other sequences, such as regulatory sequences, to allow, for example, expression in a specific cell/tissue/organ, or in a particular intracellular environment/compartment. Methods for generating, selecting and using viral vectors are well known in the art.

Antisense molecules (siRNA and shRNA) inhibiting the expression of human Ninjurin-1 are commercially available, for example from Santa Cruz Biotechnology Inc. (Cat. Nos sc-75915, sc-75915-SH and sc-75915-V) and from Invitrogen (NINJ1 Stealth RNAi™ siRNA, Cat. Nos. HSS107188, HSS107189 and HSS107190). Also, several providers (e.g., InvivoGen, Qiagen, Ambion, Inc.) offer custom-made antisense synthesis services.

In an embodiment, the above-mentioned Ninjurin-1 inhibitor is a Ninjurin-1 antibody.

By "Ninjurin-1 antibody" or "anti-Ninjurin-1" in the present context is meant an antibody capable of detecting/recognizing (i.e. binding to) a Ninjurin-1 protein or a Ninjurin-1 protein fragment. In an embodiment, the above-mentioned antibody inhibits the biological activity of Ninjurin-1, such as Ninjurin-1/Ninjurin-1 homotypic interaction or Ninjurin-1-mediated cell recruitment. In another embodiment, the Ninjurin-1 protein fragment is an extracellular domain of Ninjurin-1.

In an embodiment, the antibody specifically binds to (interacts with) a Ninjurin-1 polypeptide (e.g., the polypeptide of SEQ ID NO: 2) and displays no substantial binding to other naturally occurring proteins other than the ones sharing the same antigenic determinants as a Ninjurin-1 polypeptide. The term antibody or immunoglobulin is used in the broadest sense, and covers monoclonal antibodies (including full-length monoclonal antibodies), polyclonal antibodies, multispecific antibodies, and antibody fragments so long as they exhibit the desired biological activity. Antibody fragments comprise a portion of a full length antibody, generally an antigen binding or variable region thereof. Examples of antibody fragments include Fab, Fab', F(ab')2, and Fv fragments, diabodies, linear antibodies, single-chain antibody molecules, single domain antibodies (e.g., from camelids), shark NAR single domain antibodies, and multispecific antibodies formed from antibody fragments. Antibody fragments can also refer to binding moieties comprising CDRs or antigen binding domains including, but not limited to, $V_H$ regions ($V_H$, $V_H$-$V_H$), anticalins, PepBodies, antibody-T-cell epitope fusions (Troybodies) or Peptibodies. Additionally, any secondary antibodies, either monoclonal or polyclonal, directed to the first antibodies would also be included within the scope of this invention.

In general, techniques for preparing antibodies (including monoclonal antibodies and hybridomas) and for detecting antigens using antibodies are well known in the art (Campbell, 1984, In "Monoclonal Antibody Technology: Laboratory Techniques in Biochemistry and Molecular Biology", Elsevier Science Publisher, Amsterdam, The Netherlands) and in Harlow et al., 1988 (in: Antibody A Laboratory Manual, CSH Laboratories). The term antibody encompasses herein polyclonal, monoclonal antibodies and antibody variants such as single-chain antibodies, humanized antibodies, chimeric antibodies and immunologically active fragments of antibodies (e.g., Fab and Fab' fragments) which inhibit or neutralize their respective interaction domains and/or are specific thereto.

Polyclonal antibodies are preferably raised in animals by multiple subcutaneous (s.c.), intravenous (i.v.) or intraperitoneal (i.p.) injections of the relevant antigen (e.g., Ninjurin-1 polypeptide or a fragment thereof) with or without an adjuvant. It may be useful to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals may be immunized against the antigen (e.g., Ninjurin-1 polypeptide or a fragment thereof, such as a fragment comprising residues 26 to 37 of a Ninjurin-1 polypeptide), immunogenic conjugates, or derivatives by combining the antigen or conjugate (e.g., 100 µg for rabbits or 5 µg for mice) with 3 volumes of Freund's complete adjuvant and injecting the solution intradermally at multiple sites. One month later the animals are boosted with the antigen or conjugate (e.g., with ⅕ to ¹⁄₁₀ of the original amount used to immunize) in Freund's complete adjuvant by subcutaneous injection at multiple sites. Seven to 14 days later the animals are bled and the serum is assayed for antibody titer. Animals are boosted until the titer plateaus. Preferably, for conjugate immunizations, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal antibodies may be made using the hybridoma method first described by Kohler et al., Nature, 256: 495 (1975), or may be made by recombinant DNA methods (e.g., U.S. Pat. No. 6,204,023). Monoclonal antibodies may also be made using the techniques described in U.S. Pat. Nos. 6,025,155 and 6,077,677 as well as U.S. Patent Application Publication Nos. 2002/0160970 and 2003/0083293.

In the hybridoma method, a mouse or other appropriate host animal, such as a rat, hamster or monkey, is immunized (e.g., as hereinabove described) to elicit lymphocytes that produce or are capable of producing antibodies that will specifically bind to the antigen used for immunization. Alternatively, lymphocytes may be immunized in vitro. Lymphocytes then are fused with myeloma cells using a suitable fusing agent, such as polyethylene glycol, to form a hybridoma cell.

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In an embodiment, the above-mentioned antibody is raised against an extracellular domain of a Ninjurin-1 polypeptide (i.e. an extracellular domain of a Ninjurin-1 polypeptide is used for immunization). In a further embodiment, the above-mentioned antibody is raised against a Ninjurin-1 polypeptide fragment comprising a domain corresponding to residues 28 to 35 of a Ninjurin-1 polypeptide. In a further embodiment, the above-mentioned antibody is raised against a Ninjurin-1 polypeptide fragment comprising a domain corresponding to residues 26 to 37 of a Ninjurin-1 polypeptide.

In an embodiment, the above-mentioned antibody blocks or interferes with Ninjurin-1 homotypic interaction, for example by competing for the Ninjurin-1 binding domain or by sterically hindering the Ninjurin-1 binding domain. In another embodiment, the above-mentioned antibody binds to a domain corresponding to residues 28 to 35 of a Ninjurin-1 polypeptide. In a further embodiment, the above-mentioned antibody binds to a domain corresponding to residues 26 to 37 of a Ninjurin-1 polypeptide.

Ninjurin-1 inhibitors may also be in the form of non-antibody-based scaffolds, such as avimers (Avidia); DARPins (Molecular Partners); Adnectins (Adnexus), Anticalins (Pieris) and Affibodies (Affibody). The use of alternative scaffolds for protein binding is well known in the art (see, for example, Binz and Plückthun, 2005, *Curr. Opin. Biotech.* 16: 1-11).

In an embodiment, the Ninjurin-1 inhibitor (e.g., anti-Ninjurin-1 antibody) blocks Ninjurin-1/Ninjurin-1 homotypic interaction, for example by competing for the Ninjurin-1 binding domain or by sterically hindering the Ninjurin-1 binding domain. In a further embodiment, the above-mentioned Ninjurin-1 inhibitor binds to an extracellular domain of a Ninjurin-1 polypeptide. In another embodiment, the above-mentioned antibody binds to a domain corresponding to or comprised within residues 28 to 35 of a Ninjurin-1 polypeptide. In a further embodiment, the above-mentioned antibody binds to a domain corresponding to or comprised within residues 26 to 37 of a Ninjurin-1 polypeptide (e.g., the mouse or human Ninjurin-1 polypeptide depicted in FIG. 8).

Anti-Ninjurin-1 antibodies are commercially available, for example from Santa Cruz Biotechnology, inc. (Cat No. sc-79647 and sc-79649), Abcam™ (Cat No. ab67916 and ab85891), Sigma-Aldrich™ (Cat No. SAB1400186 and SAB2101590), R&D Systems™ (Cat No. AF5105), Novus Biologicals™ (Cat. No. H00004814-B01P and H00004814-M01A). These antibodies, or antigen-binding fragments thereof, In an embodiment, the anti-Ninjurin-1 blocking antibody is the blocking antibody described in the examples below, or an antigen-binding fragment thereof.

In an embodiment, given the known involvement of Trp and Arg residues of the above-noted domain in Ninjurin-1-mediated adhesion (see, for example, U.S. Pat. No. 6,559,288 and Araki et al., *J. Biol. Chem.* (1997) 272(34):21373-80), the above-mentioned Ninjurin-1 inhibitor is a peptide comprising a domain of formula I (SEQ ID NO: 13):

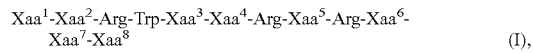

$$\text{Xaa}^1\text{-Xaa}^2\text{-Arg-Trp-Xaa}^3\text{-Xaa}^4\text{-Arg-Xaa}^5\text{-Arg-Xaa}^6\text{-Xaa}^7\text{-Xaa}^8 \quad (I),$$

wherein $Xaa^1$, $Xaa^2$, $Xaa^6$, $Xaa^7$ and $Xaa^8$ is any amino acid or is absent;

$Xaa^3$, $Xaa^4$ and $Xaa^5$ is any amino acid;

or a functional analog thereof.

In an embodiment, $Xaa^2$ is Pro. In an embodiment, $Xaa^1$ is Pro. In an embodiment, $Xaa^6$ is Pro. In an embodiment, $Xaa^7$ is Ile. In an embodiment, $Xaa^8$ is Asn. In an embodiment, $Xaa^3$ is Gly. In an embodiment, $Xaa^4$ is Leu. In an embodiment, $Xaa^5$ is Asn or Leu.

In an embodiment, the above-mentioned domain is Pro-Pro-Arg-Trp-Gly-Leu-Arg-Asn-Arg-Pro-Ile-Asn (SEQ ID NO:6).

In another embodiment, the above-mentioned Ninjurin-1 inhibitor is a peptide comprising a domain of formula II (SEQ ID NO: 14):

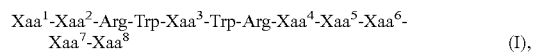

$$\text{Xaa}^1\text{-Xaa}^2\text{-Arg-Trp-Xaa}^3\text{-Trp-Arg-Xaa}^4\text{-Xaa}^5\text{-Xaa}^6\text{-Xaa}^7\text{-Xaa}^8 \quad (I),$$

wherein $Xaa^1$, $Xaa^2$, $Xaa^4$ and $Xaa^5$, $Xaa^6$, $Xaa^7$ and $Xaa^8$ is each independently any amino acid or is absent;

$Xaa^3$ is any amino acid;

or a functional analog thereof.

In an embodiment, $Xaa^1$ is Pro. In an embodiment, $Xaa^2$ is Ala. In an embodiment, $Xaa^3$ is Gly. In an embodiment, $Xaa^4$ is His. In an embodiment, $Xaa^5$ is Gly. In an embodiment, $Xaa^6$ is Pro. In an embodiment, $Xaa^7$ is Ile. In an embodiment, $Xaa^8$ is Asn.

In an embodiment, the above-mentioned domain is Arg-Trp-Gly-Trp-Arg (SEQ ID NO: 15).

In an embodiment, the above-mentioned domain is Arg-Trp-Gly-Trp-Arg-His-Gly-Pro (SEQ ID NO: 16).

In an embodiment, the above-mentioned domain is Pro-Ala-Arg-Trp-Gly-Trp-Arg-His-Gly-Pro-Ile-Asn (SEQ ID NO: 5).

In another embodiment, the above-mentioned Ninjurin-1 inhibitor is a peptide consisting of the domain of formula I defined above.

The term "amino acid" as used herein includes both L- and D-isomers of the naturally occurring amino acids as well as other amino acids (e.g., naturally-occurring amino acids, non-naturally-occurring amino acids, amino acids which are not encoded by nucleic acid sequences, etc.) used in peptide chemistry to prepare synthetic analogs of peptides. Examples of naturally-occurring amino acids are glycine, alanine, valine, leucine, isoleucine, serine, threonine, etc. Other amino acids include for example norleucine, norvaline, cyclohexyl alanine, biphenyl alanine, homophenyl alanine, naphthyl alanine, pyridyl alanine, phenyl alanines substituted at the ortho, para and meta positions with alkoxy, halogen or nitro groups etc. These amino acids are well known in the art of biochemistry/peptide chemistry.

The term "functional analog" (or "functional variant/derivative") refers to a peptide/domain having at least one modification as compared to the peptide/domain defined above, and which retain the activity of inhibiting Ninjurin-1 (e.g., blocking Ninjurin-1/Ninjurin-1 homotypic interaction).

In embodiments, the modification is a deletion, an insertion, a substitution or a chemical modification of one or more amino acids. The modification may be, for example, a deletion of (e.g., one to five) consecutive or non-consecutive amino acids, a substitution of (e.g., one to five) amino acids, one or more substitution(s) of a naturally occurring amino acid (L-amino acid) by a corresponding D-amino acid, an extension of the sequence by e.g., one, two, three or more amino acids.

In an embodiment, the above-mentioned substitution(s) are conserved amino acid substitutions.

As used herein, the term "conserved amino acid substitutions" (or sometimes "conservative amino acid substitutions") refers to the substitution of one amino acid for another at a given location in the peptide/domain, where the substitution can be made without substantial loss of the relevant Ninjurin-1 inhibitory activity. In making such changes, substitutions of like amino acid residues can be made on the basis of relative similarity of side-chain substituents, for example, their size, charge, hydrophobicity, hydrophilicity, and the like, and such substitutions may be assayed for their effect on the function of the peptide/domain by routine testing.

In some embodiments, conserved amino acid substitutions may be made where an amino acid residue is substituted for another having a similar hydrophilicity value (e.g., within a value of plus or minus 2.0), where the following may be an amino acid having a hydropathic index of about −1.6 such as Tyr (−1.3) or Pro (−1.6) are assigned to amino acid residues (as detailed in U.S. Pat. No. 4,554,101, incorporated herein by reference): Arg (+3.0); Lys (+3.0); Asp (+3.0); Glu (+3.0); Ser (+0.3); Asn (+0.2); Gln (+0.2); Gly (O); Pro (−0.5); Thr (−0.4); Ala (−0.5); His (−0.5); Cys (−1.0); Met (−1.3); Val (−1.5); Leu (−1.8); Ile (−1.8); Tyr (−2.3); Phe (−2.5); and Trp (−3.4).

In other embodiments, conserved amino acid substitutions may be made where an amino acid residue is substituted for another having a similar hydropathic index (e.g., within a value of plus or minus 2.0). In such embodiments, each amino acid residue may be assigned a hydropathic index on the basis of its hydrophobicity and charge characteristics, as follows: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glu (−3.5); Gln (−3.5); Asp (−3.5); Asn (−3.5); Lys (−3.9); and Arg (−4.5).

In other embodiments, conserved amino acid substitutions may be made where an amino acid residue is substituted for another in the same class, where the amino acids are divided into non-polar, acidic, basic and neutral classes, as follows: non-polar: Ala, Val, Leu, Ile, Phe, Trp, Pro, Met; acidic: Asp, Glu; basic: Lys, Arg, His; neutral: Gly, Ser, Thr, Cys, Asn, Gln, Tyr.

Conservative amino acid changes can include the substitution of an L-amino acid by the corresponding D-amino acid, by a conservative D-amino acid, or by a naturally-occurring, non-genetically encoded form of amino acid, as well as a conservative substitution of an L-amino acid. Naturally-occurring non-genetically encoded amino acids include beta-alanine, 3-amino-propionic acid, 2,3-diamino propionic acid, alpha-aminoisobutyric acid, 4-amino-butyric acid, N-methylglycine (sarcosine), hydroxyproline, ornithine, citrulline, t-butylalanine, t-butylglycine, N-methylisoleucine, phenylglycine, cyclohexylalanine, norleucine, norvaline, 2-napthylalanine, pyridylalanine, 3-benzothienyl alanine, 4-chlorophenylalanine, 2-fluorophenylalanine, 3-fluorophenylalanine, 4-fluorophenylalanine, penicillamine, 1,2,3,4-tetrahydroisoquinoline-3-carboxylix acid, beta-2-thienylalanine, methionine sulfoxide, homoarginine, N-acetyl lysine, 2-amino butyric acid, 2-amino butyric acid, 2,4,-diamino butyric acid, p-aminophenylalanine, N-methylvaline, homocysteine, homoserine, cysteic acid, epsilon-amino hexanoic acid, delta-amino valeric acid, or 2,3-diaminobutyric acid.

In other embodiments, conservative amino acid changes include changes based on considerations of hydrophilicity or hydrophobicity, size or volume, or charge. Amino acids can be generally characterized as hydrophobic or hydrophilic, depending primarily on the properties of the amino acid side chain. A hydrophobic amino acid exhibits a hydrophobicity of greater than zero, and a hydrophilic amino acid exhibits a hydrophilicity of less than zero, based on the normalized consensus hydrophobicity scale of Eisenberg et al. (*J. Mol. Biol.* 179: 125-142, 1984). Genetically encoded hydrophobic amino acids include Gly, Ala, Phe, Val, Leu, Ile, Pro, Met and Trp, and genetically, encoded hydrophilic amino acids include Thr, His, Glu, Gln, Asp, Arg, Ser, and Lys.

Hydrophobic or hydrophilic amino acids can be further subdivided based on the characteristics of their side chains. For example, an aromatic amino acid is a hydrophobic amino acid with a side chain containing at least one aromatic or heteroaromatic ring, which may contain one or more substituents.

An apolar amino acid is a hydrophobic amino acid with a side chain that is uncharged at physiological pH and which has bonds in which a pair of electrons shared in common by two atoms is generally held, equally by each of the two atoms (i.e., the side chain is not polar). Genetically encoded apolar amino acids include Gly, Leu, Val, Ile, Ala, and Met. Apolar amino acids can be further subdivided to include aliphatic amino acids, which is a hydrophobic amino acid having an aliphatic hydrocarbon side chain. Genetically encoded aliphatic amino acids include Ala, Leu, Val, and Ile.

A polar amino acid is a hydrophilic amino acid with a side chain that is uncharged at physiological pH, but which has one bond in which the pair of electrons shared in common by two atoms is held more closely by one of the atoms. Genetically encoded polar amino acids include Ser, Thr, Asn, and Gln.

An acidic amino acid is a hydrophilic amino acid with a side chain pKa value of less than 7. Acidic amino acids typically have negatively charged side chains at physiological pH due to loss of a hydrogen ion. Genetically encoded acidic amino acids include Asp and Glu. A basic amino acid is a hydrophilic amino acid with a side chain pKa value of greater than 7. Basic amino acids typically have positively charged side chains at physiological pH due to association with hydronium ion. Genetically encoded basic amino acids include Arg, Lys, and His.

The above classifications are not absolute and an amino acid may be classified in more than one category. In addition, amino acids can be classified based on known behavior and or characteristic chemical, physical, or biological properties based on specified assays or as compared with previously identified amino acids. Amino acids can also include bifunctional moieties having amino acid-like side chains.

Conservative changes can also include the substitution of a chemically derivatised moiety for a non-derivatised residue, by for example, reaction of a functional side group of an amino acid.

In addition to the substitutions outlined above, synthetic amino acids providing similar side chain functionality can also be introduced into the peptide/domain. For example, aromatic amino acids may be replaced with D- or L-naphthylalanine, D- or L-phenylglycine, D- or L-2-thienylalanine, D- or L-1-, 2-, 3-, or 4-pyrenylalanine, D- or L-3-thienylalanine, D- or L-(2-pyridinyl)-alanine, D- or L-(3-pyridinyl)-alanine, D- or L-(2-pyrazinyl)-alanine, D- or L-(4-isopropyl)-phenylglycine, D-(trifluoromethyl)-phenylglycine, D-(trifluoromethyl)-phenylalanine, D-p-fluorophenylalanine, D- or L-p-biphenylalanine D- or L-p-methoxybiphenylalanine, D- or L-2-indole(alkyl)alanines, and D- or L-alkylalanines wherein the alkyl group is selected from the group consisting of substituted or unsubstituted methyl, ethyl, propyl, hexyl, butyl, pentyl, isopropyl, iso-butyl, and iso-pentyl.

Non-carboxylate amino acids can be made to possess a negative charge, as provided by phosphono- or sulfated (e.g., —$SO_3H$) amino acids, which are to be considered as non-limiting examples.

Other substitutions may include unnatural alkylated amino acids, made by combining an alkyl group with any natural amino acid. Basic natural amino acids such as lysine and arginine may be substituted with alkyl groups at the amine ($NH_2$) functionality. Yet other substitutions include nitrile derivatives (e.g., containing a CN-moiety in place of the $CONH_2$ functionality) of asparagine or glutamine, and sulfoxide derivative of methionine. In addition, any amide linkage in the peptide/domain may be replaced by a ketomethylene, hydroxyethyl, ethyl/reduced amide, thioamide or reversed amide moieties, (e.g., (—C=O)—$CH_2$—), (—CHOH)—$CH_2$—), ($CH_2$—$CH_2$—), (—C=S)—NH—), or (—NH—(—C=O) for (—C=O)—NH—)).

Other modifications are also included within the definition of functional analog of the peptide/domain of the present invention. For example, the size of the peptide/domain can be reduced by deleting one or more amino acids, and/or amino acid mimetics or dipeptide mimics containing non-peptide bonds may be used. Examples of using molecular scaffolds such as benzodiazepine, azepine, substituted gamma lactam rings, keto-methylene pseudopeptides, β-turndipeptide cores and β-aminoalcohols for these purposes are known to peptide chemists and are described in for example *Peptidomimetic protocols* (Methods in molecular medicine Vol. 23) W. M. Kazmierski (ed.), Humana Press and *Advances in Amino Acid Mimetics and Peptidomimetics*, Vols. 1 & 2, A. Abell (Ed).

Covalent modifications of the peptide/domain are thus included within the scope of the present invention. Such modifications may be introduced into the peptide/domain for example by reacting targeted amino acid residues of the peptide/domain with an organic derivatizing agent that is capable of reacting with selected side chains or terminal residues. The following examples of chemical derivatives are provided by way of illustration and not by way of limitation.

Cysteinyl residues may be reacted with alpha-haloacetates (and corresponding amines), such as 2-chloroacetic acid or chloroacetamide, to give carboxymethyl or carboxyamidomethyl derivatives. Histidyl residues may be derivatized by reaction with compounds such as diethylprocarbonate e.g., at pH 5.5-7.0 because this agent is relatively specific for the histidyl side chain, and para-bromophenacyl bromide may also be used; e.g., where the reaction is preferably performed in 0.1M sodium cacodylate at pH 6.0.

Lysinyl and amino terminal residues may be reacted with compounds such as succinic or other carboxylic acid anhydrides. Other suitable reagents for derivatizing alpha-amino-containing residues include compounds such as imidoesters, e.g., methyl picolinimidate; pyridoxal phosphate; pyridoxal; chloroborohydride; trinitrobenzenesulfonic acid; O-methylisourea; 2,4 pentanedione; and transaminase-catalyzed reaction with glyoxylate.

Arginyl residues may be modified by reaction with one or several conventional reagents, among them phenylglyoxal, 2,3-butanedione, 1,2-cyclohexanedione, and ninhydrin according to known method steps. Derivatization of arginine residues is typically performed in alkaline conditions because of the high pKa of the guanidine functional group. Furthermore, these reagents may react with the groups of lysine as well as the arginine epsilon-amino group. The specific modification of tyrosinyl residues per se is well-known, such as for introducing spectral labels into tyrosinyl residues by reaction with aromatic diazonium compounds or tetranitromethane. N-acetylimidazol and tetranitromethane may be used to form O-acetyl tyrosinyl species and 3-nitro derivatives, respectively.

Carboxyl side groups (aspartyl or glutamyl) may be selectively modified by reaction with carbodiimides (R'—N=C=N—R') such as 1-cyclohexyl-3-(2-morpholinyl-(4-ethyl) carbodiimide or 1-ethyl-3-(4-azonia-4,4-dimethylpentyl) carbodiimide. Furthermore aspartyl and glutamyl residues may be converted to asparaginyl and glutaminyl residues by reaction with ammonium ions. Glutaminyl and asparaginyl residues may be frequently deamidated to the corresponding glutamyl and aspartyl residues. Other modifications of the peptides in the present invention may include hydroxylation of proline and lysine, phosphorylation of hydroxyl groups of seryl or threonyl residues, methylation of the alpha-amino groups of lysine, arginine, and histidine side chains acetylation of the N-terminal amine, methylation of main chain amide residues (or substitution with N-methyl amino acids) and, in some instances, amidation of the C-terminal carboxyl groups, according to known method steps.

Covalent attachment of fatty acids (e.g., $C_6$-$C_{18}$) to the peptide/domain may confer additional biological properties such as protease resistance, plasma protein binding, increased plasma half-life, intracellular penetration, etc. The above description of modification of a peptide/domain does not limit the scope of the approaches nor the possible modifications that can be engineered.

In embodiments, the N- and/or C-terminal amino acids of the above-mentioned peptide may be modified by amidation, acetylation, acylation or other modifications known in the art. In an embodiment, the amino terminal residue (i.e., the free amino group at the N-terminal end of the peptide) of the peptide is modified (e.g., for protection against degradation). In an embodiment, the modification is acylation with a $C_2$-$C_{16}$ acyl group, in a further embodiment, the modification is acetylation.

In an embodiment, the carboxy terminal residue (i.e., the free carboxy group at the C-terminal end of the peptide) of said peptide is modified (e.g., for protection against degradation). In an embodiment, the modification is an amidation.

In an embodiment, the above-mentioned peptide contains about 100 amino acids or less. In a further embodiment, the above-mentioned peptide contains about 90 amino acids or less. In a further embodiment, the above-mentioned peptide contains about 80 amino acids or less. In a further embodiment, the above-mentioned peptide contains about 70 amino acids or less. In a further embodiment, the above-mentioned peptide contains about 60 amino acids or less. In a further embodiment, the above-mentioned peptide contains about 50 amino acids or less. In a further embodiment, the above-mentioned peptide contains about 40 amino acids or less. In a further embodiment, the above-mentioned peptide contains about 30 amino acids or less. In a further embodiment, the above-mentioned peptide contains about 20 amino acids or less. In a further embodiment, the above-mentioned peptide contains about 15 amino acids or less. In a further embodiment, the above-mentioned peptide contains between about 5 to about 15 amino acids. In a further embodiment, the above-mentioned peptide contains 5, 6, 7, 8, 9, 10, 11, 12, 13, 14 or 15 amino acids.

The above-mentioned peptide may be produced by expression in a host cell comprising a nucleic acid encoding the peptide (recombinant expression) or by chemical synthesis (e.g., solid-phase peptide synthesis). Peptides can be readily synthesized by automated solid phase procedures well known in the art. Suitable syntheses can be performed by utilizing "T-boc" or "Fmoc" procedures. Techniques and procedures for solid phase synthesis are described in for example *Solid Phase Peptide Synthesis: A Practical Approach*, by E. Atherton and R. C. Sheppard, published by IRL, Oxford University Press, 1989. Alternatively, the peptides may be prepared by way of segment condensation, as described, for example, in Liu et al., *Tetrahedron Lett.* 37: 933-936, 1996; Baca et al., *J. Am. Chem. Soc.* 117: 1881-1887, 1995; Tam et al., *Int. J. Peptide Protein Res.* 45: 209-216, 1995; Schnolzer and Kent, *Science* 256: 221-225, 1992; Liu and Tam, *J. Am. Chem. Soc.* 116: 4149-4153, 1994; Liu and Tam, *Proc. Natl. Acad. Sci. USA* 91: 6584-6588, 1994; and Yamashiro and Li, *Int. J. Peptide Protein Res.* 31: 322-334, 1988). Other methods useful for synthesizing the peptides are described in Nakagawa et al., *J. Am. Chem. Soc.* 107: 7087-7092, 1985. Commercial providers of peptide synthetic services may also be used to prepare synthetic peptides in the D- or L-configuration. Such providers include, for example, Advanced ChemTech (Louisville, Ky.), Applied Biosystems (Foster City, Calif.), Anaspec (San Jose, Calif.), and Cell Essentials (Boston, Mass.).

Peptides and peptide analogues comprising naturally occurring amino acids encoded by the genetic code may also be prepared using recombinant DNA technology using standard methods. Peptides produced by recombinant technology may be modified (e.g., N-terminal acylation [e.g., acetylation], C-terminal amidation, cyclization/formation of a loop within the peptide [e.g., via formation of a disulphide bridge between Cys residues]) using methods well known in the art. Therefore, in embodiments, in cases where a peptide described herein contains naturally occurring amino acids encoded by the genetic code, the peptide may be produced using recombinant methods, and may in embodiments be subjected to for example the just-noted modifications (e.g., acylation, amidation, cyclization).

"Recombinant technology" refers to the production of a peptide or polypeptide by recombinant techniques, wherein generally, a nucleic acid encoding peptide is inserted into a suitable expression vector which is in turn used to transform/transfect a host cell to produce the protein. The term "recombinant" when made in reference to a protein or a polypeptide refers to a peptide, polypeptide or protein molecule which is expressed using a recombinant nucleic acid construct created by means of molecular biological techniques. Recombinant nucleic acid constructs may include a nucleotide sequence which is ligated to, or is manipulated to become ligated to, a nucleic acid sequence to which it is not ligated in nature, or to which it is ligated at a different location in nature. Referring to a nucleic acid construct as "recombinant" therefore indicates that the nucleic acid molecule has been manipulated using genetic engineering, i.e., by human intervention. Recombinant nucleic acid constructs may for example be introduced into a host cell by transformation/transfection. Such recombinant nucleic acid constructs may include sequences derived from the same host cell species or from different host cell species, which have been isolated and reintroduced into cells of the host species. Recombinant nucleic acid construct sequences may become integrated into a host cell genome, either as a result of the original transformation of the host cells, or as the result of subsequent recombination and/or repair events.

The peptides of the invention can be purified by many techniques well known in the art, such as reverse phase chromatography, high performance liquid chromatography (HPLC), ion exchange chromatography, size exclusion chromatography, affinity chromatography, gel electrophoresis, and the like. The actual conditions used to purify a particular peptide or peptide analog will depend, in part, on synthesis strategy and on factors such as net charge, hydrophobicity, hydrophilicity, and the like, and will be apparent to those of ordinary skill in the art. For affinity chromatography purification, any antibody which specifically binds the peptide or peptide analog may for example be used.

In an embodiment, the above-mentioned peptide is substantially pure. A compound is "substantially pure" when it is separated from the components that naturally accompany it. Typically, a compound is substantially pure when it is at least 60%, more generally 75%, preferably over 90% and more preferably over 95%, by weight, of the total material in a sample. Thus, for example, a polypeptide that is chemically synthesized or produced by recombinant technology will generally be substantially free from its naturally associated components. A substantially pure peptide can be obtained, for example, by extraction from a natural source; by expression of a recombinant nucleic acid molecule encoding a peptide compound; or by chemical synthesis. Purity can be measured using any appropriate method such as column chromatography, gel electrophoresis, HPLC, etc.

In another aspect, the present invention provides a composition comprising the above-mentioned Ninjurin-1 inhibitor and a pharmaceutically acceptable carrier or excipient. Such compositions may be prepared in a manner well known in the pharmaceutical art. Supplementary active compounds can also be incorporated into the compositions. As used herein "pharmaceutically acceptable carrier" or "excipient" includes any and all solvents, buffers, dispersion media, coatings, antibacterial and antifungal agents, isotonic and absorption delaying agents, and the like that are physiologically compatible. The carrier can be suitable, for example, for intravenous, parenteral, subcutaneous, intramuscular, intracranial, intraorbital, ophthalmic, intraventricular, intracapsular, intraspinal, intrathecal, epidural, intracisternal, intraperitoneal, intranasal or pulmonary (e.g., aerosol) administration (see Remington: The Science and Practice of Pharmacy by Alfonso R. Gennaro, 2003, 21$^{th}$ edition, Mack Publishing Company).

Formulations suitable for oral administration may include (a) liquid solutions, such as an effective amount of active agent(s)/composition(s) suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for compounds/compositions of the invention include ethylenevinyl acetate copolymer particles, osmotic pumps, implantable infusion systems, and liposomes. Formulations for inhalation may contain excipients, (e.g., lactose) or may be aqueous solutions containing, for example, polyoxyethylene-9-lauryl ether, glycocholate and deoxycholate, or may be oily solutions for administration in the form of nasal drops, or as a gel.

For preparing pharmaceutical compositions from the compound(s)/composition(s) of the present invention, pharmaceutically acceptable carriers are either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material.

In powders, the carrier is a finely divided solid, which is in a mixture with the finely divided active component. In tablets, the active component is mixed with the carrier having the necessary binding properties in suitable proportions and compacted in the shape and size desired. The powders and tablets may typically contain from 5% or 10% to 70% of the active compound/composition. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Liquid form preparations include solutions, suspensions, and emulsions, for example, water or water/propylene glycol solutions. For parenteral injection, liquid preparations can be formulated in solution in aqueous polyethylene glycol solution.

Aqueous solutions suitable for oral use are prepared by dissolving the Ninjurin-1 inhibitor in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, and other well-known suspending agents.

In an embodiment, the Ninjurin-1 inhibitor is formulated/administered such that it comes into contact with neural cells or neural tissue, such as central nervous system (CNS) cells or tissue. Such tissue includes brain and spinal cord (e.g., cervical, thoracic, or lumbar) tissue. As such, in embodiments, the Ninjurin-1 inhibitor can be administered to treat neural cells/tissue in vivo via direct intracranial injection or injection into the cerebrospinal fluid (e.g., intrathecal injection). Alternatively, the Ninjurin-1 inhibitor can be administered systemically (e.g. intravenously) and may come into contact with the affected neural tissue via lesions (where the blood-brain barrier is compromised), or, in a further embodiment, may be in a form capable of crossing the blood-brain barrier and entering the neural system (e.g., CNS). Further, in an embodiment, a composition of the invention may be formulated for such administration to neural cells/tissue. Methods and reagents for delivering compounds to the CNS are well known in the art (see, for example, Ken A. Witt and Thomas P. Davis, AAPS Journal. 2006; 8(1): E76-E88; Misra et al, J Pharm Pharmaceut Sci 6(2):252-273, 2003; Pathan et al, Recent Patents on Drug Delivery & Formulation 2009, 3: 71-89). In an embodiment, the above-mentioned Ninjurin-1 inhibitor may be linked (directly or indirectly) to a moiety capable or targeting a neural cells/tissue (e.g., a CNS targeting moiety), for example a molecule binding to a receptor expressed in the CNS (e.g., on the BBB). Such CNS targeting moieties are well known in the art (see, for example, U.S. Patent publication No. 2010/0015117).

The composition may also contain more than one active compound for the particular indication being treated, preferably those with complementary activities that do not adversely affect each other. It may be desirable to use the above-mentioned Ninjurin-1 inhibitor or composition in addition to one or more agents currently used to prevent or treat the disorder in question. The above-mentioned Ninjurin-1 inhibitor may be formulated in a single composition or in several individual compositions which may be co-administered in the course of the treatment.

The invention further provides a kit or package comprising the above-mentioned Ninjurin-1 inhibitor or the above-mentioned composition, together with instructions for (i) the prevention and/or treatment of a neuroinflammatory condition in a subject and/or (ii) for inhibiting the recruitment of a myeloid cell across the CNS endothelium. The kit may further comprise, for example, containers, buffers, a device (e.g., syringe) for administering the Ninjurin-1 inhibitor or a composition comprising same.

Given the correlation between Ninjurin-1 expression/activity and (i) neuroinflammation as well as (ii) immune cell recruitment to the CNS, compounds which are capable of decreasing Ninjurin-1 expression/activity may be used for the prevention and/or treatment of neuroinflammatory conditions and/or for inhibiting immune cell recruitment to the CNS. Therefore, the invention further relates to screening methods (e.g. in vitro methods) for the identification and characterization of compounds capable of decreasing/inhibiting Ninjurin-1 expression and/or activity, which may be used for the prevention and/or treatment of neuroinflammatory conditions and/or for inhibiting immune cell recruitment to the CNS.

In another aspect, the present invention provides a method of identifying a compound for preventing or treating a neuroinflammatory condition, said method comprising determining whether: (a) a level of expression of a Ninjurin-1 nucleic acid or encoded polypeptide; (b) a level of Ninjurin-1 activity (e.g., Ninjurin-1 homotypic binding activity); or (c) a combination of (a) and (b), is decreased in the presence of a test compound relative to in the absence of said test compound; wherein said decrease is indicative that said test compound may be used for preventing or treating said neuroinflammatory condition.

In another aspect, the present invention provides a method of identifying or characterizing a compound for preventing or treating a neuroinflammatory condition, said method comprising: (a) contacting a test compound with a cell comprising a first nucleic acid comprising a transcriptionally regulatory element normally associated with a Ninjurin-1 gene, operably linked to a second nucleic acid comprising a reporter gene capable of encoding a reporter protein; and (b) determining whether reporter gene expression or reporter protein activity is decreased in the presence of said test compound; wherein a decrease in said reporter gene expression or reporter protein activity is indicative that said test compound may be used for preventing or treating said neuroinflammatory condition.

In another aspect, the present invention provides a method of identifying a compound for inhibiting the recruitment of a myeloid cell across the CNS endothelium, said method comprising determining whether: (a) a level of expression of a Ninjurin-1 nucleic acid or encoded polypeptide; (b) a level of Ninjurin-1 activity (e.g., Ninjurin-1 homotypic binding activity); or (c) a combination of (a) and (b), is decreased in the presence of a test compound relative to in the absence of said test compound; wherein said decrease is indicative that said test compound may be used for inhibiting the recruitment of a myeloid cell across the CNS endothelium.

In another aspect, the present invention provides a method of identifying or characterizing a compound for inhibiting the recruitment of a myeloid cell across the CNS endothelium, said method comprising: (a) contacting a test compound with a cell comprising a first nucleic acid comprising a transcriptionally regulatory element normally associated with a Ninjurin-1 gene, operably linked to a second nucleic acid comprising a reporter gene capable of encoding a reporter protein; and (b) determining whether reporter gene expression or reporter protein activity is decreased in the presence of said test compound: wherein a decrease in said reporter gene expression or reporter protein activity is indicative that said test compound may be used for inhibiting the recruitment of a myeloid cell across the CNS endothelium.

In an embodiment, the above-mentioned Ninjurin-1 activity is a binding activity. Methods to measure the binding of a compound to Ninjurin-1 are well known in the art (see, for example, U.S. Pat. No. 6,559,288).

The above-noted screening method or assay may be applied to a single test compound or to a plurality or "library" of such compounds (e.g., a combinatorial library). Any such compounds may be utilized as lead compounds and further modified to improve their therapeutic, prophylactic and/or pharmacological properties for preventing and/or treating a neuroinflammatory condition.

Test compounds (drug candidates) may be obtained from any number of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural or synthetically produced libraries and compounds are readily modified through conventional chemical, physical and biochemical means.

Screening assay systems may comprise a variety of means to enable and optimize useful assay conditions. Such means may include but are not limited to: suitable buffer solutions, for example, for the control of pH and ionic strength and to provide any necessary components for optimal activity and stability (e.g., protease inhibitors), temperature control means for optimal activity and/or stability, of Ninjurin-1, and detection means to enable the detection of its activity. A variety of such detection means may be used, including but not limited to one or a combination of the following: radiolabelling, antibody-based detection, fluorescence, chemiluminescence, spectroscopic methods (e.g., generation of a product with altered spectroscopic properties), various reporter enzymes or proteins (e.g., horseradish peroxidase, green fluorescent protein), specific binding reagents (e.g., biotin/(strept)avidin), and others.

As noted above, the invention further relates to methods for the identification and characterization of compounds capable of decreasing Ninjurin-1 gene expression. Such a method may comprise assaying Ninjurin-1 gene expression in the presence versus the absence of a test compound. Such gene expression may be measured by detection of the corresponding RNA or protein, or via the use of a suitable reporter construct comprising one or more transcriptional regulatory element(s) normally associated with a Ninjurin-1 gene, operably-linked to a reporter gene.

A first nucleic acid sequence is "operably-linked" with a second nucleic acid sequence when the first nucleic acid sequence is placed in a functional relationship with the second nucleic acid sequence. For instance, a promoter is operably-linked to a coding sequence if the promoter affects the transcription or expression of the coding sequences.

Generally, operably-linked DNA sequences are contiguous and, where necessary to join two protein coding regions, in reading frame. However, since, for example, enhancers generally function when separated from the promoters by several kilobases and intronic sequences may be of variable lengths, some polynucleotide elements may be operably-linked but not contiguous. "Transcriptional regulatory element" is a generic term that refers to DNA sequences, such as initiation and termination signals, enhancers, and promoters, splicing signals, polyadenylation signals which induce or control transcription of protein coding sequences with which they are operably-linked. The expression of such a reporter gene may be measured on the transcriptional or translational level, e.g., by the amount of RNA or protein produced. RNA may be detected by for example Northern analysis or by the reverse transcriptase-polymerase chain reaction (RT-PCR) method (see for example Sambrook et al. (1989) Molecular Cloning: A Laboratory Manual ($2^{nd}$ edition), Cold Spring Harbor Laboratory Press, Cold Spring Harbor, N.Y., USA).

Protein levels may be detected either directly using affinity reagents (e.g., an antibody or fragment thereof (for methods, see for example Harlow, E. and Lane, D (1988) Antibodies: A Laboratory Manual, Cold Spring Harbor Laboratory Press, Cold Spring Harbor, N.Y.); a ligand which binds the protein) or by other properties (e.g., fluorescence in the case of green fluorescent protein) or by measurement of the protein's activity, which may entail enzymatic activity to produce a detectable product (e.g., with altered spectroscopic properties) or a detectable phenotype (e.g., alterations in cell growth/function). Suitable reporter genes include but are not limited to chloramphenicol acetyltransferase, beta-D galactosidase, luciferase, or green fluorescent protein (GFP).

Ninjurin-1 protein expression levels could be determined using any standard methods known in the art. Non-limiting examples of such methods include Western blot, tissue microarray, immunoblot, enzyme-linked immunosorbant assay (ELISA), radioimmunoassay (RIA), immunoprecipitation, surface plasmon resonance, chemiluminescence, fluorescent polarization, phosphorescence, immunohistochemical analysis, matrix-assisted laser desorption/ionization time-of-flight (MALDI-TOF) mass spectrometry, microcytometry, microscopy, fluorescence activated cell sorting (FACS), flow cytometry, and assays based on a property of the protein including but not limited to DNA binding, ligand binding, or interaction with other protein partners.

Methods to determine Ninjurin-1 nucleic acid (mRNA) levels are known in the art, and include for example polymerase chain reaction (PCR), reverse transcriptase-PCR (RT-PCR) (e.g., as in Example 3 below), in situ PCR, SAGE, quantitative PCR (q-PCR), in situ hybridization, Southern blot, Northern blot, sequence analysis, microarray analysis, detection of a reporter gene, or other DNA/RNA hybridization platforms. For RNA expression, preferred methods include, but are not limited to: extraction of cellular mRNA and Northern blotting using labeled probes that hybridize to transcripts encoding all or part of one or more of the genes of this invention; amplification of mRNA expressed from one or more of the genes of this invention using gene-specific primers, polymerase chain reaction (PCR), quantitative PCR (q-PCR), and reverse transcriptase-polymerase chain reaction (RT-PCR), followed by quantitative detection of the product by any of a variety of means; extraction of total RNA from the cells, which is then labeled and used to probe cDNAs or oligonucleotides encoding all or part of the genes of this invention, arrayed on any of a variety of surfaces; in situ hybridization.

In embodiments, competitive screening assays may be done by combining a Ninjurin-1 polypeptide, or a fragment thereof (a Ninjurin-1 binding domain) and a probe to form a probe: Ninjurin-1 binding domain complex in a first sample followed by adding a test compound. The binding of the test compound is determined, and a change, or difference in binding of the probe in the presence of the test compound indicates that the test compound is capable of binding to the Ninjurin-1 binding domain and potentially modulating Ninjurin-1 activity.

The binding of the test compound may be determined through the use of competitive binding assays. In this embodiment, the probe is labeled with an affinity label such as biotin. Under certain circumstances, there may be competitive binding between the test compound and the probe, with the probe displacing the candidate agent. In one case, the test compound may be labeled. Either the test compound, or a compound of the present invention, or both, is added first to the Ninjurin-1 binding domain for a time sufficient to allow binding to form a complex.

The assay may be carried out in vitro utilizing a source of Ninjurin-1 which may comprise a naturally isolated or recombinantly produced Ninjurin-1 (or a variant/fragment thereof), in preparations ranging from crude to pure. Such assays may be performed in an array format. In certain embodiments, one or a plurality of the assay steps are automated.

In embodiments, the assays described herein may be performed in a cell or cell-free format.

A homolog, variant and/or fragment of Ninjurin-1 which retains activity (e.g., a binding activity) may also be used in the methods of the invention.

"Homology", "homologous" and "homolog" refer to sequence similarity between two polypeptide molecules. Homology can be determined by comparing each position in the aligned sequences. A degree of homology between amino acid sequences is a function of the number of identical or matching amino acids at positions shared by the sequences. Two nucleotide or amino acid sequences are considered "substantially identical" if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%, e.g., with any of the sequences described herein. As used herein, a given percentage of homology between sequences denotes the degree of sequence identity in optimally aligned sequences. An "unrelated" or "non-homologous" sequence shares less than 40% identity, though preferably less than about 25% identity, with any of the sequences described herein.

Optimal alignment of sequences for comparisons of identity may be conducted using a variety of algorithms, such as the local homology algorithm of Smith and Waterman, 1981, *Adv. Appl. Math* 2: 482, the homology alignment algorithm of Needleman and Wunsch, 1970, *J. Mol. Biol.* 48: 443, the search for similarity method of Pearson and Lipman, 1988, *Proc. Natl. Acad. Sci. USA* 85: 2444, and the computerised implementations of these algorithms (such as GAP, BESTFIT, FASTA and TFASTA in the Wisconsin Genetics Software Package, Genetics Computer Group, Madison, Wis., U.S.A.). Sequence identity may also be determined using the BLAST algorithm, described in Altschul et al., 1990, *J. Mol. Biol.* 215:403-10 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighbourhood word score threshold. Initial neighbourhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program may use as defaults a word length (W) of 11, the BLOSUM62 scoring matrix (Henikoff and Henikoff, 1992, *Proc. Natl. Acad. Sci. USA* 89: 10915-10919) alignments (B) of 50, expectation (E) of 10 (or 1 or 0.1 or 0.01 or 0.001 or 0.0001), M=5, N=4, and a comparison of both strands. One measure of the statistical similarity between two sequences using the BLAST algorithm is the smallest sum probability (P(N)), which provides an indication of the probability by which a match between two nucleotide or amino acid sequences would occur by chance. In alternative embodiments of the invention, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M $NaHPO_4$, 7% sodium dodecyl sulfate (SDS), 1 mM EDTA at 65° C., and washing in 0.2×SSC/0.1% SDS at 42° C. (see Ausubel, et al. (eds), 1989, *Current Protocols in Molecular Biology*, Vol. 1, Green Publishing Associates, Inc., and John Wiley & Sons, Inc., New York, at p. 2.10.3). Alternatively, hybridization to filter-bound sequences under stringent conditions may, for example, be performed in 0.5 M $NaHPO_4$, 7% SDS, 1 mM EDTA at 65° C., and washing in 0.1×SSC/0.1% SDS at 68° C. (see Ausubel, et al. (eds), 1989, supra). Hybridization conditions may be modified in accordance with known methods depending on the sequence of interest (see Tijssen, 1993, *Laboratory Techniques in Biochemistry and Molecular Biology—Hybridization with Nucleic Acid Probes*, Part I, Chapter 2 "Overview of principles of hybridization and the strategy of nucleic acid probe assays", Elsevier, New York). Generally, stringent conditions are selected to be about 5° C. lower than the thermal melting point for the specific sequence at a defined ionic strength and pH.

In an embodiment, the above-mentioned homolog, variant and/or fragment of Ninjurin-1 comprises a region corresponding to residues 28 to 35 ($Arg^{28}$-$Pro^{35}$) of the human Ninjurin-1 polypeptide (FIG. 8B). In a further embodiment, the above-mentioned Ninjurin-1 polypeptide or fragment thereof comprises a region corresponding to residues 26 to 37 ($Pro^{26}$-$Asn^{37}$) of the human Ninjurin-1 polypeptide.

The present inventors have shown in human samples and neuroinflammatory mouse models (EAE and SCI) that Ninjurin-1 is expressed or overexpressed on CNS cells and peripheral immune cells (myeloid cells) in neuroinflammatory conditions, and thus that Ninjurin-1 may be used as a biological marker for the detection and characterization of neuroinflammatory conditions.

Therefore, in another aspect, the invention relates to the diagnosis and prognosis of a neuroinflammatory condition. The invention thus provides a method for diagnosing or prognosing a neuroinflammatory condition in a subject based on the expression and/or activity of Ninjurin-1 determined in a sample (e.g., a CNS sample or a blood/blood cell sample) from the subject. The expression and activity of Ninjurin-1 in the sample may be determined using the assays/methods described above.

In an embodiment, the method may comprise determining whether Ninjurin-1 activity and/or expression is modulated, e.g., upregulated or increased, relative to a control/reference activity or expression. In yet another embodiment, the control Ninjurin-1 expression or activity can be selected from an established standard, a corresponding Ninjurin-1 expression or activity determined in the subject (in a sample from the subject) at an earlier time; a corresponding Ninjurin-1 expression or activity determined in a control subject known to not having a neuroinflammatory condition (e.g., a healthy subject). In such cases, an increased or higher expression and/or activity in the sample from the subject relative to the control activity or expression is indicative that the subject has a neuroinflammatory condition. "Higher expression" as used herein refers to (i) higher expression of Ninjurin-1 on one or more given cells present in the sample and/or (ii) increased amount (absolute or relative amount) of Ninjurin-1-expressing/positive cells in the sample.

In another embodiment, the control Ninjurin-1 expression or activity is a corresponding expression or activity in a control subject known to have a neuroinflammatory condition. In such a case, a comparable or higher Ninjurin-1 expression and/or activity in a sample from the subject relative to the control expression or activity is indicative that the subject has a neuroinflammatory condition.

Methods for normalizing the level of expression of a gene are well known in the art. For example, the expression level of a gene of the present invention can be normalized on the basis of the relative ratio of the mRNA level of this gene to the mRNA level of a housekeeping gene or the relative ratio of the protein level of the protein encoded by this gene to the protein level of the housekeeping protein, so that variations in the sample extraction efficiency among cells or tissues are reduced in the evaluation of the gene expression level. A "housekeeping gene" is a gene the expression of which is substantially the same from sample to sample or from tissue to tissue, or one that is relatively refractory to change in response to external stimuli. A housekeeping gene can be any RNA molecule other than that encoded by the gene of interest that will allow normalization of sample RNA or any other marker that can be used to normalize for the amount of total RNA added to each reaction. For example, the GAPDH gene, the G6PD gene, the actin gene, ribosomal RNA, 36B4 RNA, PGK1, RPLP0, or the like, may be used as a housekeeping gene.

Methods for calibrating the level of expression of a gene are well known in the art. For example, the expression of a gene can be calibrated using reference samples, which are commercially available. Examples of reference samples include, but are not limited to: Stratagene™ QPCR Human Reference Total RNA, Clontech™ Universal Reference Total RNA, and XpressRef™ Universal Reference Total RNA.

In an embodiment, the above-mentioned method comprises determining the level of a Ninjurin-1 nucleic acid (e.g., the nucleic acid of SEQ ID NO: 1 or a nucleic acid which encodes the polypeptide of SEQ ID NO: 2) in the sample. In another embodiment, the above-mentioned method comprises determining the level of a Ninjurin-1 polypeptide (e.g., the polypeptide of SEQ ID NO: 2) in the sample. In an embodiment, the level of a Ninjurin-1 polypeptide is determined using an anti-Ninjurin-1 antibody.

"Sample" or "biological sample" refers to any solid or liquid sample isolated from a live being. In a particular embodiment, it refers to any solid or liquid sample isolated from a human, such as a biopsy material, blood, saliva, synovial fluid, urine, amniotic fluid and cerebrospinal fluid. In an embodiment, the above-mentioned sample is obtained from the central nervous system (e.g., a CNS cell, tissue or fluid). In a further embodiment, the CNS cell is obtained by a biopsy. In a further embodiment, the CNS cell is a CNS endothelial cell.

In another embodiment, the above-mentioned sample is a blood sample or a blood cell sample. In a further embodiment, the above-mentioned blood cell sample is a peripheral blood mononuclear cell (PBMC) sample. In an embodiment, the above-mentioned blood or blood cell sample comprises myeloid cells, such as monocytes and/or dendritic cells. In an embodiment, the above-mentioned blood or blood cell sample may be submitted to one or more cell depletion or enrichment steps, so as to enrich the sample in one or more cell types of interest (e.g., myeloid cells, such as monocytes and/or dendritic cells). In an embodiment, the above-mentioned method comprises determining the proportion or relative amount of Ninjurin-$1^+$-cell in said sample and comparing it to a corresponding proportion or relative amount in a control/reference sample.

In an embodiment, the methods of diagnosis/prognostication noted above may be performed in conjunction with the therapeutic/prophylactic methods noted above, for preventing and/or treating a neuroinflammatory condition in a subject. Such a method thus comprises the diagnosis or prognostication of a neuroinflammatory condition in a subject and, in accordance with the diagnosis/prognosis, decreasing Ninjurin-1 levels in the subject (e.g., in a cell, tissue or organ of the subject) thereby to prevent or treat the neuroinflammatory condition.

In another aspect, the present invention provides a method for monitoring the course of treatment of a patient suffering from a neuroinflammatory condition (e.g., MS, SCI), the method comprising (a) determining the expression and/or activity of Ninjurin-1 in a sample from said patient; wherein a decrease in said expression and/or activity relative to a corresponding expression and/or activity of Ninjurin-1 determined in a biological sample obtained from said patient at an earlier time is indicative that said patient is responsive to said treatment. In an embodiment, a similar or an increased expression and/or activity relative to a corresponding expression and/or activity of Ninjurin-1 determined in a biological sample obtained from said patient at an earlier time is indicative that said patient is not responsive to said treatment.

The present invention also provides a kit or package comprising a reagent useful for determining Ninjurin-1 expression and activity (e.g., a ligand that specifically binds a Ninjurin-1 polypeptide such as an anti-Ninjurin-1 antibody, or a ligand that specifically binds a Ninjurin-1 nucleic acid such as an oligonucleotide). Such kit may further comprise, for example, instructions for the prognosis and/or diagnosis of a neuroinflammatory condition, control samples, containers, reagents useful for performing the methods (e.g., buffers, enzymes), etc.

As used herein the term "subject" is meant to refer to any animal, such as a mammal including human, mice, rat, dog, cat, pig, cow, monkey, horse, etc. In an embodiment, the above-mentioned subject is a mammal, in a further embodiment a human.

The present invention is illustrated in further details by the following non-limiting examples.

EXAMPLE 1

Materials and Methods

BBB-endothelial cell isolation and culture. BBB-endothelial cells were isolated from non-epileptic material according to a previously published protocol (Prat et al., *J Neuropathol Exp Neurol.* 2000 59(10):896-906; Biernacki et al., *J Neuropathol Exp Neurol.* 2001 60(12): 1127-36; Prat et al., *Arch Neurol.* 2002 59(3): 391-7). BBB-endothelial cells were grown in primary cultures in media composed of Medium 199 (Gibco® Invitrogen, Burlington, ON, Canada) supplemented with 20% clone M3 conditioned media, 10% fetal bovine serum (FBS), 5% normal human serum (HS), 0.13% endothelial cell growth supplement (ECGS) and 0.2% insulin-transferrin-selenium on 0.5% gelatin-coated tissue culture plastic plates (all reagents from Sigma, Oakville, ON, Canada). For treatments, the BBB-endothelial cells were grown in culture media in the presence of 40% astrocyte conditioned media (ACM), until they reach confluency. When indicated BBB-endothelial cells were activated for 24 hours with 100 U/ml of Tumor Necrosis Factor (TNF) and 100 U/ml of Interferon (IFN)-γ (Biosource-Invitrogen, Carlsbad, Calif., USA) in the presence of 40% ACM and the absence of ECGS. As previously demonstrated, these cells express factor VIII, von Willebrand factor, Ulex Agglutenens Europaensis-1-binding sites, endothelial antigen HT-7; and are susceptible to tumor necrosis factor (TNF)-induced CD54 and CD106 up-regulation. Immunoreactivity for glial fibrillary acidic protein and α-myosin could not be detected, confirming the absence of contaminating astrocytes and smooth muscle cells, respectively. The absence of monocytes and macrophages was confirmed by immunostaining with anti-CD14 and anti-CD11c antibodies.

Astrocyte and microglia isolation and culture. Astrocytes were cultured as previously described (Jack et al., 2005; Wosik et al., 2007). Astrocytes were grown in primary cultures in complete Dulbecco's Modified Eagle Media (DMEM) (Invitrogen) supplemented with 10% FBS on plastic plates. Astrocyte-conditioned media (ACM) was harvested once a week from confluent flasks and used in the culture media of the BBB-endothelial cells when mentioned. Human adult microglia were cultured as previously described (Lambert et al., 2008) in DMEM supplemented with 10% FBS.

Leukocyte isolation and culture. Venous blood samples were obtained from consenting healthy donors or Multiple Sclerosis (MS) patients in accordance with institutional guidelines. Peripheral blood mononuclear cells (PBMCs) were isolated from whole blood by a density gradient centrifugation using Ficoll-Paque™ PLUS (GE Healthcare, Bio-Sciences AB, Sweden). Ex vivo $CD4^+$, $CD8^+$, $CD14^+$ and $CD19^+$ cells were isolated from PBMCs using CD4, CD8, CD14 and CD19 mouse anti-human MicroBeads respectively (Miltenyi Biotec Inc., Auburn, Calif., USA). To generate mature DCs, PBMCs were first cultured in RPMI 1640 (Wisent Inc., St-Bruno, Qc, Canada), supplemented with 5% HS (Sigma), 2 mM L-glutamine, 100 U/ml penicillin and 100 μg/ml streptomycine (Sigma) for 2 hours at 37° C. to enable the cells to adhere. The media was removed and the cells were washed with PBS to remove the non adherent cells. Fresh culture media containing 20 ng/ml of Granulocyte Macrophage Colony Stimulating Factor (GM-CSF, BD Biosciences) and 10 ng/ml of Interleukin (IL)-4 (R&D Systems, Minneapolis, Minn., USA). Culture media was replaced every 2 days with fresh media, containing GM-CSF and IL-4, to remove the non adherent cells. After 6 days, 100 ng/ml of lipopolysaccharide (LPS, from *Escherichia coli* Serotype 0111:B4, Sigma) was added. Mature DCs were harvested 2 days later for analysis.

Flow Cytometric analysis of Ninjurin-1 expression. Cells were harvested and resuspended in FACS buffer composed of PBS supplemented with 1% FBS (Biosource-Invitrogen) and 0.1% $NaN_3$ (Sigma). The cells were incubated with HS (Biosource-Invitrogen) to prevent unspecific binding. BBB-endothelial cells and PBMCs were incubated for 1 h at 4° C. with the primary unconjugated monoclonal mouse anti-Ninjurin-1 antibody (20 μg/ml, BD Biosciences), or with the Functional Grade Purified Mouse IgG2a Isotype Control (20 μg/ml, ebioscience, Inc., San Diego, Calif., USA). Cells were then incubated for 30 min at 4° C. with an allophycocyanin (APC)-conjugated goat anti-mouse Ig (2 μg/ml, BD Biosciences) to detect specific binding. Cells were then counter-stained for 30 min at 4° C. with mouse anti-human conjugated antibodies: Human Leukocyte Antigen (HLA)-ABC, Intracellular cell adhesion molecule (ICAM)-1, CD3, CD4, CD8, CD19, HLA-DR, CD14, CD83, CD123, CD209, CD11c or with corresponding isotype controls (all from BD Biosciences). To study the expression of Ninjurin-1 on murine immune cells, the mouse monoclonal anti-Ninjurin-1 antibody was biotinylated, to prevent unspecific binding of the secondary antibody. A buffer exchange was performed with a Slide-A-Lyzer® Dialysis Cassette (3.5-20K Cassettes, Thermo Scientific, Rockford, Ill., USA) to remove glycerol and bovine serum albumin (BSA) from the antibody solution using Melon™ Gel IgG Spin Purification Kit. Biotin was added using the EZ-Link® Micro $NHS-PEO_4$-Biotinylation kit according to the manufacturer's instructions (Thermo Scientific). Murine peripheral blood or CNS mononuclear cells were incubated for 1 h at 4° C. with the primary biotinylated monoclonal mouse anti-Ninjurin-1 antibody (5 μg/ml, BD Biosciences), or with the Biotin-conjugated IgG2a, K isotype control (5 μg/ml, ebioscience). Cells were then incubated for 30 min at 4° C. with secondary antibody goat anti-peroxidase—APC (2 μg/ml, BD Biosciences). Counter-staining with anti-mouse CD3, CD4, CD8, CD11b, CD11c, CD45, F4/80, Ly6C, MHC class II or with corresponding isotype controls (BD Biosciences and BioLegend, San Diego, Calif., USA) were performed. Cells were acquired on a BD LSR™ II Flow cytometer and analyzed using the BD FACSDiva™ software (BD Biosciences).

Western blot. Ex vivo $CD4^+$, $CD8^+$, $CD14^+$ and $CD19^+$ cells (isolated using MACS™ beads, Miltenyi Biotec), mature dendritic cells, primary cultures of BBB endothelial and CNS material from EAE or SCI animals were lysed in denaturing buffer (0.1% SDS in 50 mM Tris-HCl pH 8.5) with Proteinase Inhibitor Cocktail (BD BaculoGold™, BD Biosciences), and sonicated using the Vibra Cell™ ultrasonic processor (Sonics & Materials, Inc., Newtown, Conn., USA). Proteins were quantified using the BCA™ Protein Assay kit (Thermo Scientific). Thirty micrograms of proteins were separated on a 12% SDS-PAGE gel and the proteins were transferred on Immun-Blot™ PVDF Membrane (Bio-Rad Laboratories, Hercules, Calif., USA). The membranes were blocked (1 h at room temperature) with 5% donkey serum (Sigma), or with 5% non-fat dry milk, in Tris Buffered Saline-0.1% Tween®20 (Sigma-Aldrich, St-Louis, Mo., USA) and then incubated overnight at 4° C. with the primary antibody: polyclonal sheep anti-Human Ninjurin-1 (1:100 dilution; R&D Systems) or monoclonal mouse anti-Ninjurin-1 (1:150 dilution; BD Biosciences). Secondary antibody Peroxidase-conjugated affiniPure Donkey Anti-Sheep IgG (H+L) (1:10,000 dilution; Jackson ImmunoResearch Laboratories, West Grove, Pa., USA) or secondary antibody rabbit anti-mouse immunoglobulins/HRP (1:1000 dilution; DakoCytomation, Glostrup, Denmark), and ECL™ Westernblotting Analysis System (Amersham™ GE Healthcare, Buckinghamshire, UK) were used to detect specific binding. Mouse anti-β-Actin (1:20,000 dilution; Sigma) was used as a loading control (rabbit anti-mouse immunoglobulins/HRP; 1:1000 dilution; DakoCytomation). HepG2 cell lysate was used as a positive control for the expression of Ninjurin-1 (BD Bioscience). For spinal cord injury material, proteins were extracted from 5 mm length of spinal cord tissue containing the lesion site.

Immunocytofluorescent stainings. BBB-endothelial cells were grown in chambers slides (Lab Tek™, Nunc™, by Thermoscientific) and were either un-treated or treated for 24 h with TNF and IFN-λ (100 U/ml). Cells were fixed for 10 minutes at room temperature with 70% ethanol and incubated overnight at 4° C. with mouse monoclonal anti-Ninjurin-1 (1:50 dilution; BD Biosciences). Counter-staining with F-actin (Sigma) were performed. Slides were mounted using Gelvatol containing either Hoechst 33258 pentahydrate (10 µg/ml, Molecular Probes, Eugene, Oreg., USA) or TO-PRO-3 (Invitrogen), as nuclear stains.

Immunofluorescent stainings of human and mouse CNS material. Luxol Fast Blue (LFB) and H&E stainings (Wosik et al., 2007) were performed on human and mouse brain tissue specimens obtained from four MS patients (autopsy) and EAE/SCI animals. Sections showing acute demyelinating lesions and active perivascular mononuclear cell infiltration were selected (8 to 12 blocks per MS donor), and compared to normal-appearing white matter from the same donors (8 blocks per donor) and to non-neurological disease controls (3 donors; 9-11 blocks per donor). Mean age was 49±6 years and disease duration ranged from 3 to 23 years. The cause of death was pneumonia (2), urosepsis (1) and barbiturate intoxication (1). Sections (n=40) from MS patients (n=5) and disease controls (n=5) were fixed in −20° C. acetone for 10 minutes, hydrated in PBS and blocked with the avidin/biotin blocking kit (Invitrogen). CNS material from EAE (n=6) and SCI (n=6) animals were collected following rapid intra-cardiac PBS perfusion and snap-frozen in liquid nitrogen. Non-specific immunoglobulin binding was blocked with 10% goat serum for 30 minutes at room temperature (rt). Sections were incubated for 40 minutes with Biotin-labelled mouse anti-Ninjurin-1 (1/50, R&D Systems) diluted in 3% goat serum and washed 7 times with PBS and 0.05% Tween™ 20 after each incubation. Ninjurin-1 immunostaining was revealed using Cy3- or HRP-labelled streptavidin (DakoCytomation). Sections were mounted using Gelvatol containing either Hoechst 33258 pentahydrate (10 µg/ml, Molecular Probes) or TO-PRO-3 (Invitrogen), as nuclear stains. Additional immunostainings were performed using monoclonal Abs raised against human or mouse CD3, -CD4, CD11c, F4/80, Mac-2 and -IBA-1. Negative controls were performed omitting the primary antibody. Fluorescence was visualized on a Leica™ DM6000 B epifluorescent microscope equipped with a DFC480 digital camera (Leica Microsystems, Wetzlar Germany) or on a Leica™ SP5 confocal microscope. Images were acquired using Openlab™ 4.0.4 (Improvision, Waltham, Mass.) and processed and analyzed with Adobe Photoshop™ CS2 (Adobe, Mountain View, Calif.). Numbers of CD11c+ DCs, F4/80+ macrophages and MHC II+ cells in spinal cord were quantified in pictures of 15 random fields of the spinal cord (two mice per treatment group). All counts were made by two investigators 'blinded' to the identity of the treatment group.

Ninjurin-1 blocking peptides and antibodies. Peptides corresponding to the adhesion motif of Ninjurin-1, located between amino acids 26 and 37 of Ninjurin-1 [ human sequence: PARWGWRHGPIN (SEQ ID NO: 5); mouse sequence: PPRWGLRNRPIN (SEQ ID NO: 6)], were used as a blocking peptides (referred to as Ninj$_{26-37}$). An irrelevant peptide (sequence: WRGNPGIRWAPH, SEQ ID NO: 12) was also used as a control (scramble). Custom Ninj$_{26-37}$ blocking and control peptides were synthesized by Alpha Diagnostic International (ADI, San Antonio, Tex., USA). In vitro and in vivo assays were also performed using a sheep anti-human Ninjurin-1 blocking Ab or the corresponding isotype control (Sheep IgG; both from R&D Systems).

In vitro model of the BBB. BBB-ECs grown in primary cultures were used to generate an in vitro model of the human BBB, as published previously (Cayrol et al., Nature Immunol 9(2): 137-45 Epub 2007 Dec. 23). Human BBB-endothelial cells (25×10$^3$ cells/chamber) were grown in primary culture on 3 µm porous membrane (Becton Dickinson Labware, Franklin Lakes, N.J., USA), coated with 0.5% gelatin (Sigma), in endothelial cell culture media supplemented with 40% ACM, for 4 days to reach confluency. The BBB-endothelial cells were treated with 0.4 mM of scramble peptide (WRGNPGIRWAPH, SEQ ID NO: 12), 0.4 mM of human Ninj$_{26-37}$ (PARWGWRHGPIN; SEQ ID NO: 5), 10 µg/ml of sheep IgG isotype control or 10 µg/ml of sheep anti-human Ninjurin-1 blocking Ab one hour prior to the addition of the leukocytes. Human ex vivo CD14$^+$ monocytes, or CD4$^+$, or CD8$^+$ lymphocytes were isolated, from consenting healthy donors, as described above. The leukocytes were added to the upper chamber (1×10$^6$ cells/chamber) and were allowed to migrate across human BBB-endothelial cells for 24 h. The cells that migrated through the BBB-endothelial cells, were recovered from the lower chamber and counted manually. All migration data shown represent at least 3 independent experiments performed in triplicate.

Flow system. Human BBB-ECs (2.5×10$^5$ cells/slide) were cultured on a µ-slide™ of 0.6 mm (Ibidi Integrated BioDiagnostics) in EC media in a final volume of 200 µl for 4 days to reach confluency. After 4 days, the media was replaced with fresh media and the µ-slide™ was placed inside a live chamber in order to assemble the flow system (Live Chamber 37° C. and 5% CO2). The µ-slide was connected to the flow system with a 50 cm long perfusion set tubing (aperture diameter of 0.8 mm) with a 90° angled connector. The flow generated by the Ibidi pump system was controlled via the Ibidi pump control software (Ibidi Integrated BioDiagnostics). BBB-ECs were treated with the scramble peptide (0.4 mM), human Ninj$_{26-37}$ peptide (0.4 mM), isotype control (10 µg/ml) or anti-Ninjurin-1 blocking Ab (10 µg/ml) 1 h prior to the addition of monocytes in a volume of 4 ml with a constant flow (applied air pressure: −3.7 mbar, flow rate: 0.43 ml/min, shear stress: 0.56 dyn/cm$^2$, shear rate: 27 γ/sec, cycle duration: 120 sec, unidirectional flow). After isolation of human monocytes, cells were labeled with CFSE and treated for 1 h at 4° C. CFSE-labeled monocytes (5×10$^6$) were then added to the flow system for a final volume of 5 ml. Pictures to evaluate the number of adherent cells were taken using a Leica™ DMI-6000 inverted microscope focused on BBB-ECs. The cell velocity was evaluated using a Hamamatsu™ ORCA-ER digital camera combined with the Impovisation Volocity™ software v5.3.1. Image capture and time-lapse acquisition videos were recorded at constant intervals during 1 h. Cell images and tracking were automatically quantified and analyzed from pictures and videos taken using an algorithm in Volocity™ software, removing clump cells and small debris based on their size and their basal fluorescence.

Human and Mouse T lymphocyte proliferation assay. The role of Ninjurin-1 in unspecific and specific T cell activation was assessed using the vital dye CFSE (Invitrogen). PBMCs, CD4$^+$CD45RO$^+$ memory T cells and CD14$^+$ monocytes were isolated from consenting healthy donors, as previously described (Kebir et al., 2007). PBMCs and CD4$^+$CD45RO$^+$ were resuspended at a concentration of 10×10$^6$ cells/ml in RPMI 1640 and incubated for 10 min at 37° C. with 5 mM CFSE. CFSE labeling was quenched with HS; cells were washed and resuspended in RPMI 1640 supplemented with 5% HS, 2 mM L-glutamine, 100 U/ml penicillin, 100 µg/ml streptomycine (Sigma). Unspecific activation of PBMCs was achieved by addition of anti-human CD3 Ab (2.5 µg/ml, clone OKT3, eBioscience) and recombinant human IL-2 (20 U/ml, BD Biosciences). Specific activation was achieved by adding CD14$^+$ monocytes and HA$_{306-318}$ peptide (30 mg/ml) to CFSE labeled-CD4$^+$CD45RO$^+$ cells. Cells were cultured for 6 days in the presence of scramble peptide (0.4 mM), Ninj$_{26-37}$ blocking peptide (0.4 mM), isotype control (10 µg/ml) or anti-Ninjurin-1 blocking antibody (10 µg/ml) and then harvested for FACS analysis. For proliferation assays in mice, spleen and lymph nodes were collected from EAE animals 7 days post-induction, mashed separately and passed through a 70 µm cell strainer to make single cell suspensions. Splenocytes were treated with 0.83% ammonium chloride for 3 min at room temperature to lyse red blood cells. Cells were then passed again through another 70 µm cell strainer, combined with lymph nodes cells, labeled with CFSE and resuspended in RPMI 1640 with 10% FBS. Cells were then cultured for 2 days with 15 µg/ml MOG$_{35-55}$, 2.5 ng/ml recombinant mouse IL-12, 20 ng/ml recombinant mouse IL-23 and with anti-Ninjurin-1 blocking Ab (or isotype control at 10 µg/ml) or Ninj$_{26-37}$ blocking peptide (or scramble peptide at 0.4 mM). Cells were harvested for FACS analysis.

EAE mice. Experimental autoimmune encephalomyelitis (EAE) was induced by active immunization of female purchased from Charles River Laboratories (Montréal, Qc, Canada) and Jackson Laboratory (Bar Habor, Me., USA). Seven-8 week old mice were injected subcutaneously with 200 µg of myelin oligodendrocytes glycoprotein (MOG)$_{35-55}$ peptide [Sequence: MEVGWYRSPFSRVVHLYRNGK (SEQ ID NO: 7)] emulsified in complete Freund's Adjuvant supplemented with 600 µg of *Mycobacterium tuberculosis* H37RA (DIFCO Laboratories, Detroit, Mich., USA). On day 0 and 2, mice were injected intraperitoneally with 500 ng of Pertussis toxin (List Biological Laboratories, INC., Campbell, Calif., USA). Starting on day 3, mice were injected intraperitoneally, twice a day, with 200 µg of murine Ninj$_{26-37}$ blocking peptide or the scramble peptide or with PBS used as the vehicle control. For experiments carried out with Ninjurin-1 neutralizing Ab, mice were injected with 150 µg of anti-Ninjurin-1 blocking Ab or isotype control at days 4, 6, 8 and 10 post-induction. Animals were monitored daily for signs of EAE and the scoring system was as follows: 0=no clinical symptoms; 0.5=partial floppy tail, 1=floppy tail; 2=ataxia; 2.5=weakness in hind limbs, 3=paralysis of one hind limb; 4=paralysis of both hind limbs, 5=moribund.

Spinal cord injury. Adult (8-10 weeks old) female C57BL/6 mice were anesthetized with ketamine:xylazine:acepromazine (50:5:1 mg/kg). After performing a laminectomy at the 11$^{th}$ thoracic vertebrae, the exposed spinal cord was contused using the Infinite Horizons™ Impactor device (Precision Scientific Instrumentation, Lexington, Ky.). Injuries were made using a force of 60 kDynes, and only animals that had tissue displacements ranging between 500-700 µm were used for experiments. Mice were injected intraperitoneally with 100 µg of the murine Ninj$_{26-37}$ blocking peptide or PBS (in 200 µl) every 12 hours, starting one hour after injury and for 7 days, or with PBS as a vehicle control. Locomotor recovery was evaluated in an open-field test using the Basso Mouse Scale (BMS) (Basso D. M. et al., (2006). *J Neurotrauma*. 23(5): 635-59). The BMS analysis of hind limb movements and coordination was carried out by two trained independent technicians and the consensus score taken. The final score is presented as mean±SEM.

Quantitative Real Time PCR (qRT-PCR). RNA from 5 mm length of the uninjured and injured spinal cord containing the lesion site was harvested at 1, 3, 7, 14, 21 and 28 dpi and extracted using RNeasy™ Lipid Tissue kit (Qiagen, Mississauga, Ontario, Canada). Three individual spinal cords per time point were used. 1 µl of the RT product was added to 24 µl of Brilliant™ SYBR™ Green quantitative PCR Master Mix (Stratagene), and qRT-PCR was performed to analyze the expression of Ninjurin-1 (MX4000 apparatus, Stratagene). The primers used for Ninjurin-1 amplification were: 5'-AGG GCC ATG AAG ATC AGA ACT GGA-3' (sense, SEQ ID NO: 8) and 5'-ATG GAT TTG CTG CAT GTC CTT GGG-3' (antisense, SEQ ID NO: 9). GAPDH was used as a housekeeping gene for control, and the primers used for GAPDH amplification were: 5'-CAA AGT TGT CAT GGA TGA CC-3' (sense, SEQ ID NO; 10) and 5'-CCA TGG AGA AGG CTG GGG-3' (antisense, SEQ ID NO: 11) (Cayrol et al., 2008, supra). The amount of cDNA was calculated based on the threshold cycle (CT) value, and was standardized by the amount of housekeeping gene using the 2-ΔΔCT method (Livak and Schmittgen, *Methods* 2001 25(4): 402-408). ΔΔCT were calculated as follow: ΔΔCT=(CT. Target−CT, GAPDH)−(CT. Target−CT, GADPH).

Statistical analysis. Statistical analyses were performed using PRISM 4 Graphpad™ Software (San Diego, Calif.) and data are presented as the mean±the standard error of the mean (SEM). One-way analysis of variance (ANOVA) was performed followed by Bonferroni multiple comparison post-test for all experiments except for the migration across the BBB, which was done using two-way ANOVA. Only p values <0.05 were considered significant. The data reported are either from either one representative experiment out of 3 independent experiments or pooled from 3 to 10 experiments.

EXAMPLE 2

Expression of Ninjurin-1 in Human BBB-endothelial Cells and Blood Cells

Figure 1B:
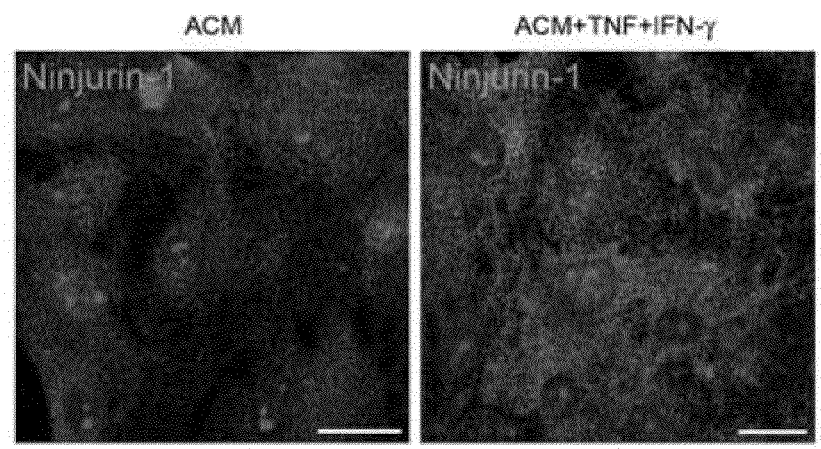
Figure 2A:
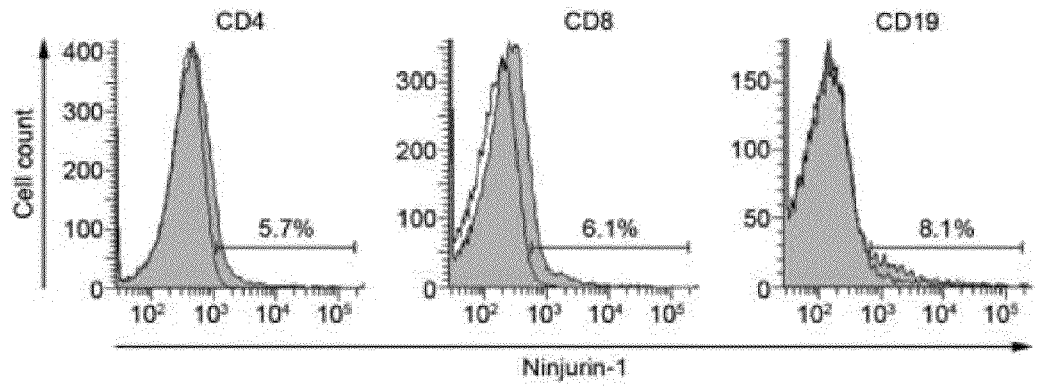
FIGS. 2A-2D show the expression of Ninjurin-1 on human cells.
Figure 2B:
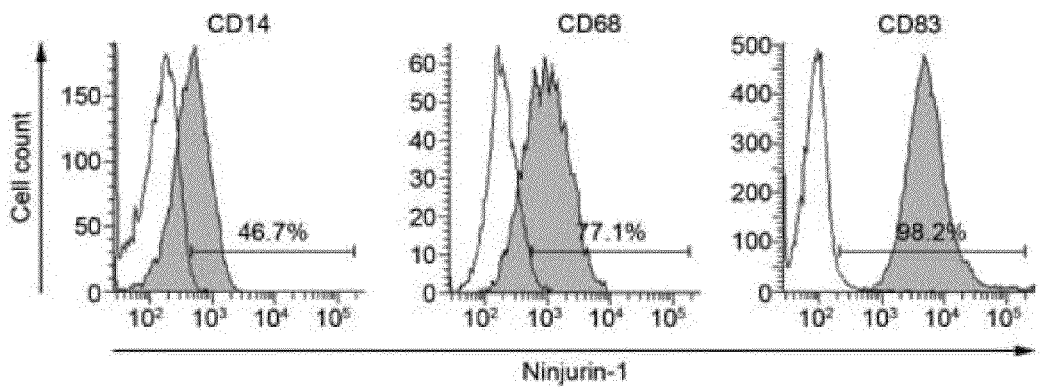
Figure 2C:
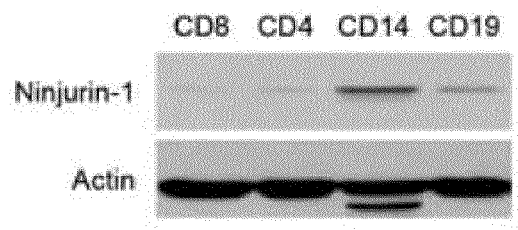
Figure 2D:
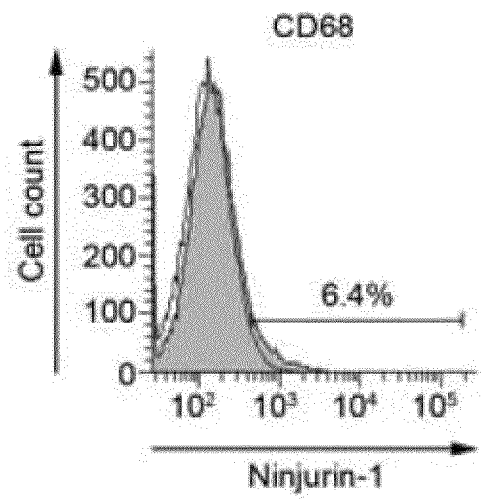
Figure 12:
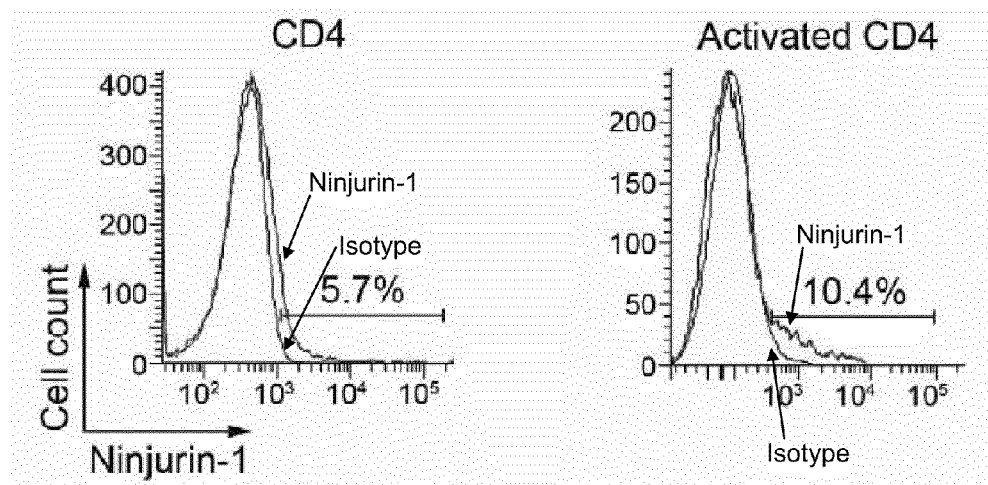
FIG. 12 shows the expression of Ninjurin-1 on activated $CD4^+$ T lymphocytes. Flow cytometry analyses of Ninjurin-1 expression on ex vivo human $CD4^+$ T lymphocytes (left panel) and on activated $CD4^+$ T lymphocytes (right panel) showing a moderate increase in Ninjurin-1 expression as compared to ex vivo T cells. CD4 activation was achieved by culture of PBMCs in presence of anti-human CD3 antibody (2.5 µg/ml, clone OKT3) and recombinant human IL-2 (20 U/ml) for 5 days.

Ninjurin-1 is expressed on the surface of human brain endothelial cells in vitro and in situ, and that its expression is upregulated in the context of inflammation. The expression of Ninjurin-1 on BBB-endothelial cells was shown to increase following treatment with proinflammatory cytokines, such as TNF and IFN-γ, as demonstrated by flow cytometry, Western blot and immunocytofluorescence (FIGS. 1A and 1B). In addition to being present on endothelial cells, Ninjurin-1 is also expressed by different subtypes of human leukocytes, preferentially on cells of the myeloid lineage such as $CD14^+$ monocytes, $CD68^+$ macrophages and $CD83^+$ dendritic cells (DCs) (FIGS. 2B and 2C). In contrast, human peripheral blood T and B lymphocytes ($CD4^+$ T cells, $CD8^+$ T cells, as well as $CD19^+$ B cells) only show weak or modest expression of Ninjurin-1 (FIGS. 2A and 2C). Activated $CD4^+$ T lymphocytes show a moderate increase in Ninjurin-1 expression as compared to ex vivo T cells (FIG. 12).

Thus, Ninjurin-1, the ligand involved in the interaction with endothelial Ninjurin-1 through homotypic interaction, is primarily expressed by human peripheral blood myeloid cells (myeloid antigen-presenting cells).

EXAMPLE 3

Expression of Ninjurin-1 in Neuroinflammatory Conditions

Figure 3A:
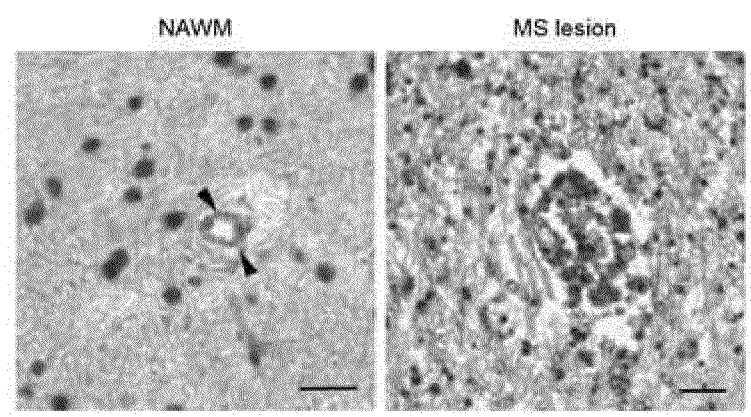
FIGS. 3A-C show the in situ detection of Ninjurin-1 in multiple sclerosis (MS) lesions.
Figure 3B:
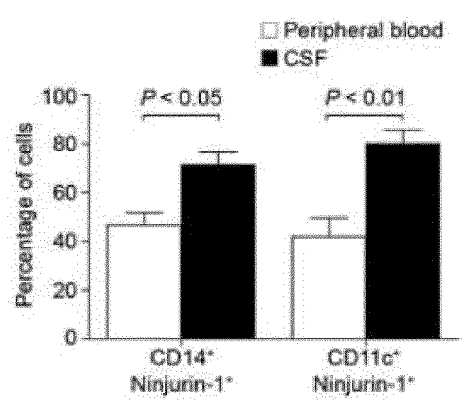
Figure 3C:
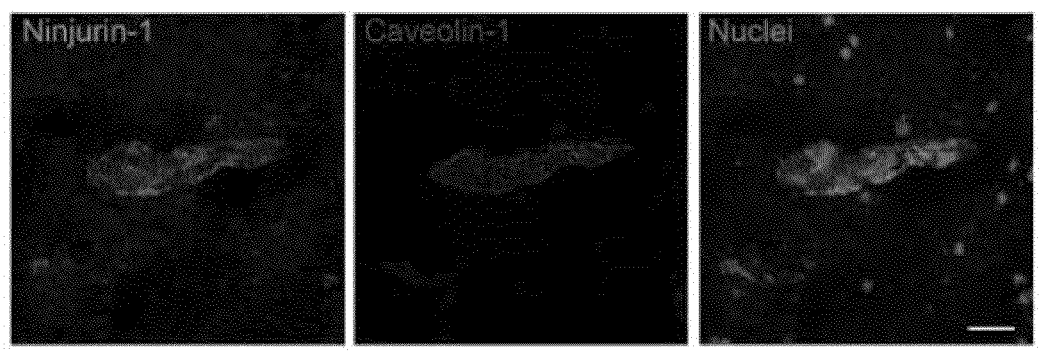
Figure 3D:
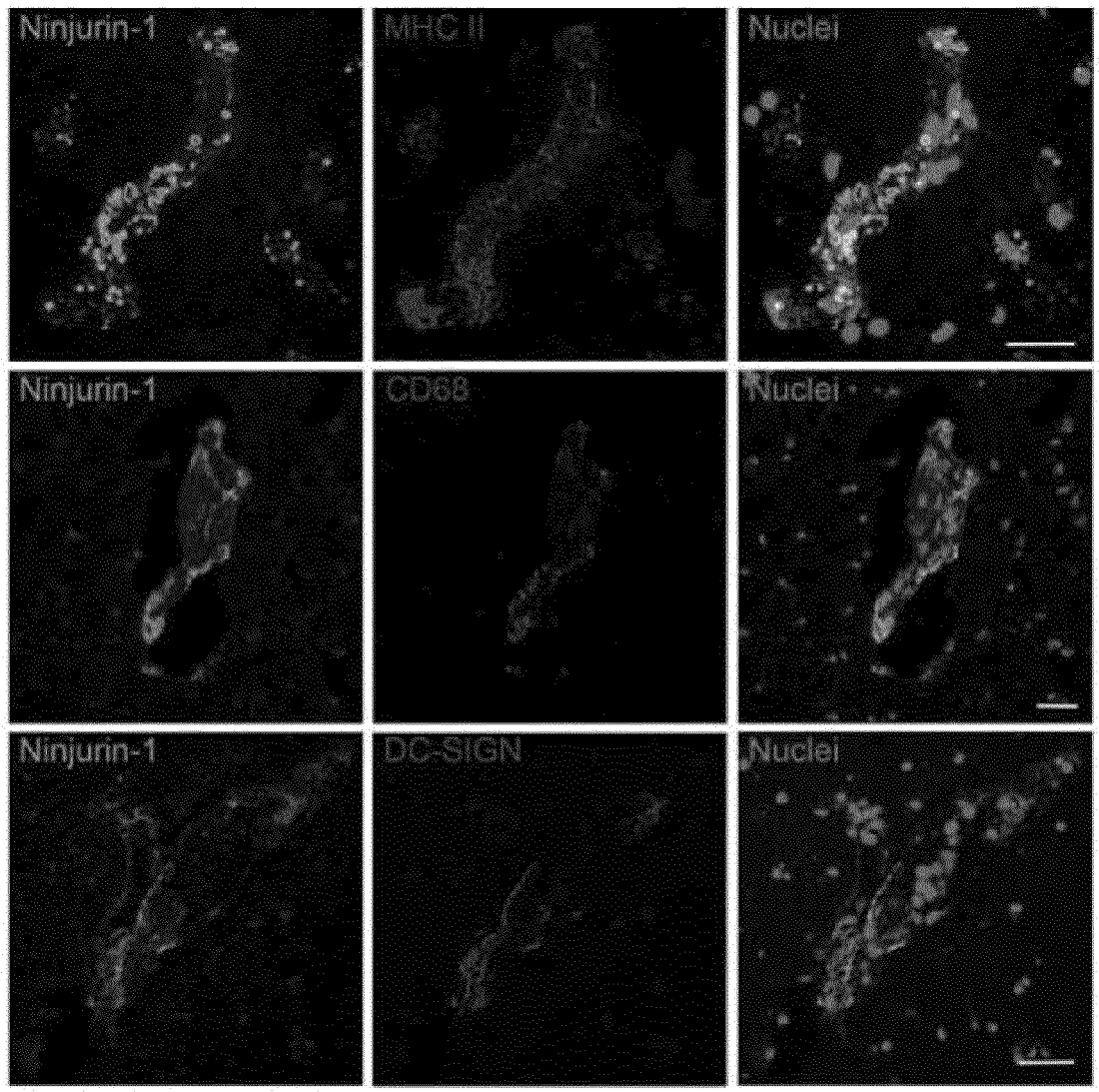
FIG. 3D: Immunofluorescent staining and confocal microscopy analysis of active MS lesions expressing Ninjurin-1 and either MHC (top panels), $CD68^+$ (middle panels) or $DC\text{-}SIGN^+$ (bottom panels). Co-localization is seen in right panels with TO-PRO-3 nuclear staining. Scale bars, 30 µm. Photomicrographs shown are representative of immunostainings performed on 12 active plaques and 15 NAWM obtained from frozen CNS material of MS patients (n=3)
Figure 4A:
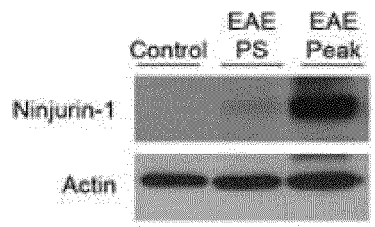
FIGS. 4A-D show the expression of Ninjurin-1 in the CNS of mice affected by experimental autoimmune encephalomyelitis (EAE) and spinal cord injury (SCI).
Figure 4B:
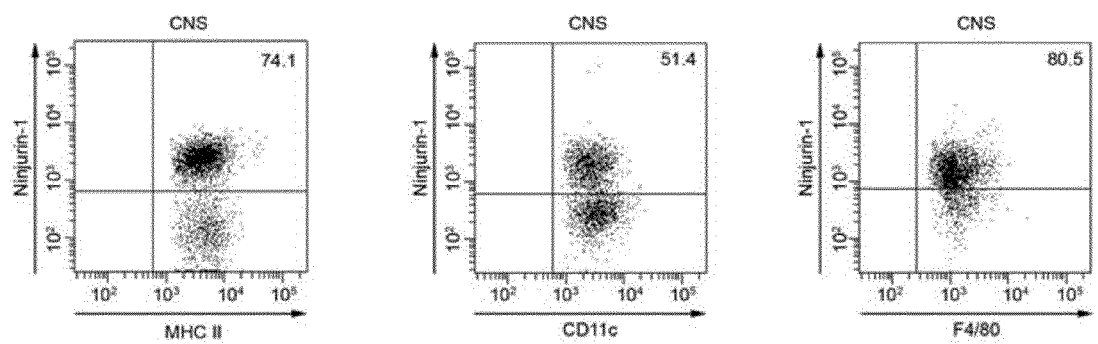
Figure 4C:
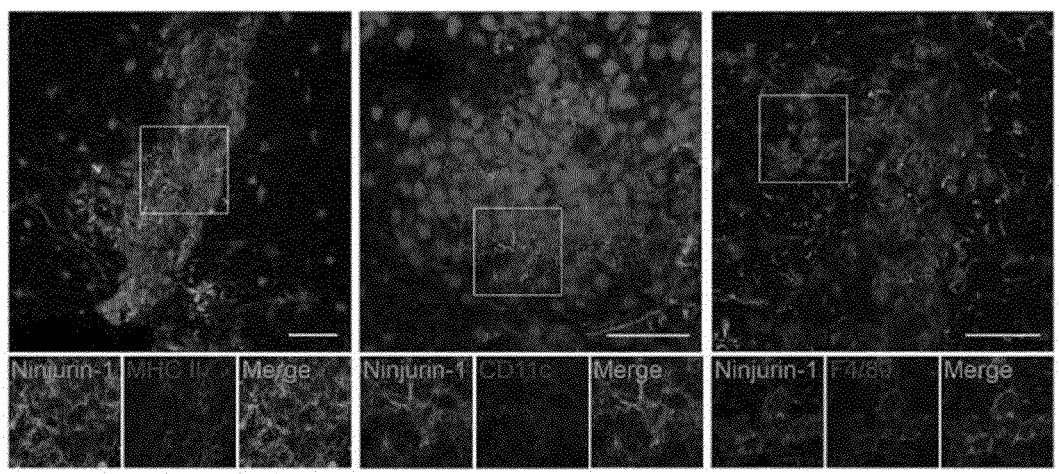
Figure 4D:
Figure 14:
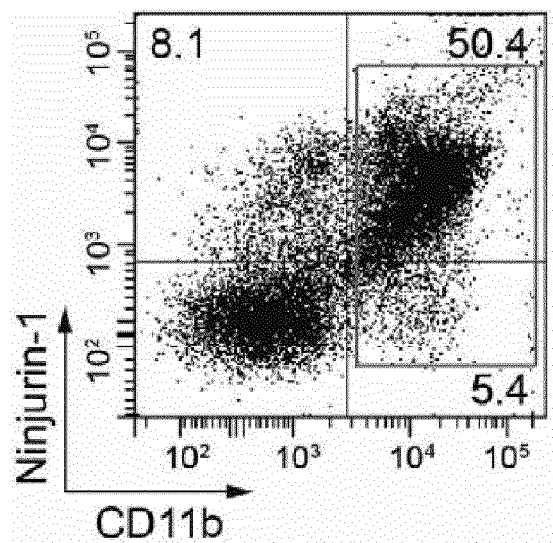
FIG. 14 shows the expression of Ninjurin-1 by antigen-presenting cells. Flow cytometry analysis showing expression of Ninjurin-1 and CD11b in CNS cells (brain and spinal cord homogenates) of $MOG_{35-55}$-immunized mice. Most Ninjurin-$1^+$ cells are $CD11b^+$ antigen-presenting cells (APCs) and most $CD11b^+$ cells are Ninjurin-$1^+$. Data shown are representative of two independent experiments.

Although Ninjurin-1 signal is weak on vessels in human control non-inflamed CNS specimens in situ, its expression significantly increases on the cerebral vascular endothelium in MS lesions (FIG. 3A). Ninjurin-1 is also detected in situ in infiltrating immune cells within MS lesions, and particularly in MHC II, $CD68^+$ and DC-SIGN$^+$ cells (FIG. 3D). FIG. 3B shows that the proportion of $CD14^+$ and $CD11c^+$ cells co-expressing Ninjurin-1 is increased in the cerebrospinal fluid (CSF) as compared to the peripheral blood of MS patients. These results suggest a role for Ninjurin-1 in the histopathology of MS. Similarly, Ninjurin-1 is expressed in spinal cord homogenates of mice affected with experimental autoimmune encephalomyelitis (EAE) and on $CD11c^+$ DCs and $F4/80^+$ macrophages infiltrating the CNS. EAE was induced in C57BL/6 mice by active immunization with myelin oligodendrocytes glycoprotein $(MOG)_{35-55}$ peptide (myelin oligodendrocyte glycoprotein emulsified in complete Freund's adjuvant) as previously described (Cayrol et al., 2008, supra). An increase in the expression of Ninjurin-1 protein in the spinal cord of mice affected with EAE was observed (FIG. 4A). Upregulation of Ninjurin-1 expression correlated with higher disease score (FIG. 4A). Furthermore, MHC II$^+$, $CD11c^+$ and $F4/80^+$ myeloid cells that have reached the CNS express high levels of Ninjurin-1, as observed by flow cytometry (FIG. 4B) and immunostaining of spinal cords (FIG. 4C). Also, it was observed that most Ninjurin-1$^+$ cells are $CD11b^+$ antigen-presenting cells (APCs), and most $CD11b^+$ cells are Ninjurin-1$^+$ (FIG. 14).

EXAMPLE 4

Figure 5A:
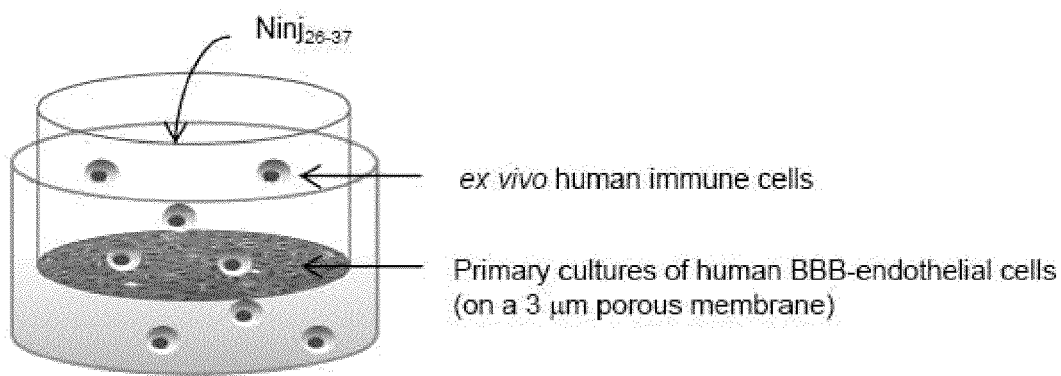
FIGS. 5A-D show the effect of Ninjurin-1 blockade on $CD14^+$ monocyte migration across human BBB-endothelial cells. The adhesion motif of human Ninjurin-1 is used as a blocking peptide, called $Ninj_{26-37}$ (sequence: $NH_2$—PPRWGLRNRPIN—COOH).
Figure 5B:
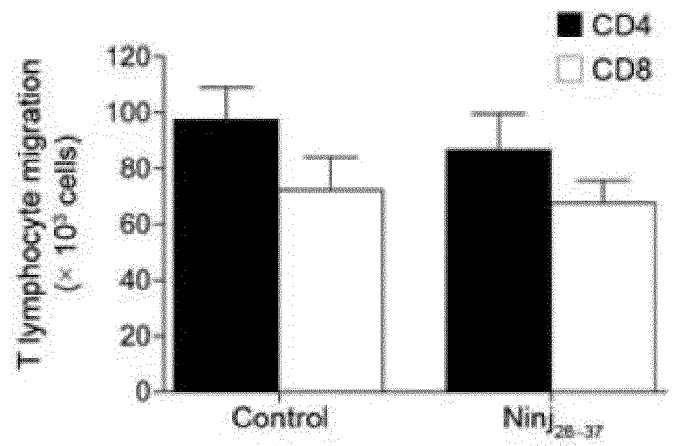
Figure 5C:
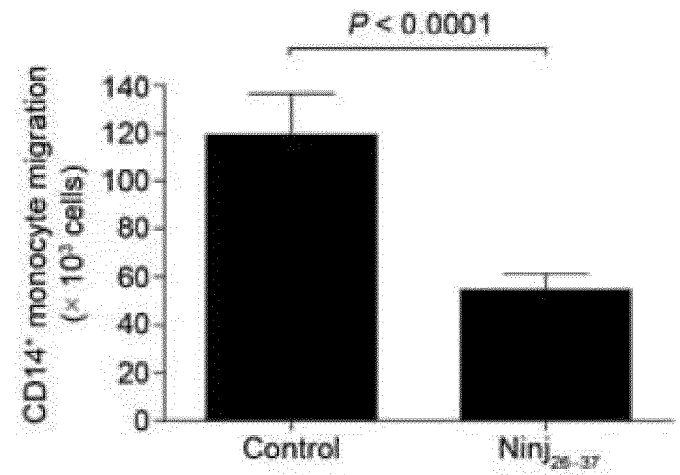
Figure 5D:
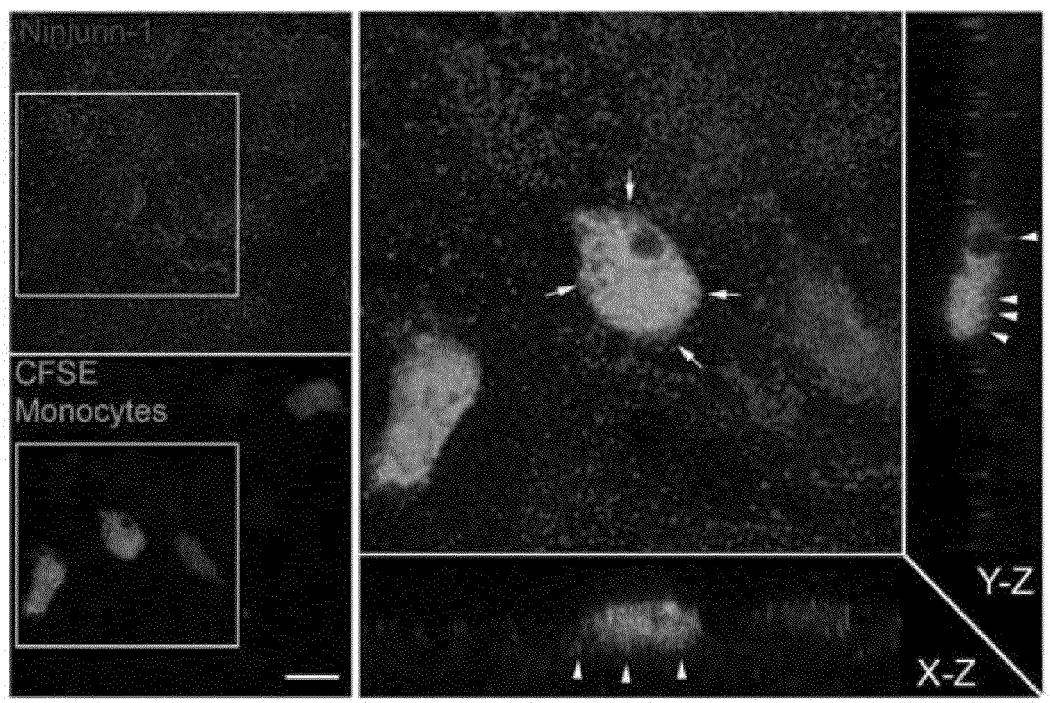
Figure 11:
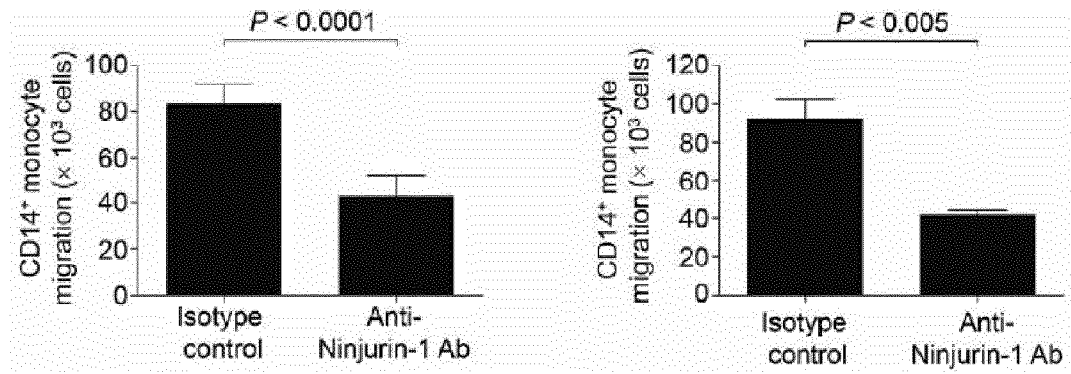
FIG. 11 shows the effect of pre-treatment of endothelial cells or $CD14^+$ monocytes with an anti-Ninjurin-1 antibody. Left panel: Ex vivo human $CD14^+$ monocytes were allowed to migrate across a monolayer of human BBB-ECs for 24 h. BBB-ECs were previously pre-treated for 1 h at 37° C. in the presence of isotype control (sheep IgG) or sheep anti-human Ninjurin-1 blocking antibody (Ab) (10 µg/ml). Ninjurin-1 blockade with the Ab significantly restricts the migration of $CD14^+$ monocytes across BBB-ECs as compared with the isotype control. Data shown are representative of seven independent experiments (n=7 blood donors) performed in triplicate using six distinct BBB-EC preparations. Right panel: Ex vivo human $CD14^+$ monocytes were pre-treated with isotype control or blocking Ab (10 µg/ml) for 1 h at 4° C. prior to migration across a monolayer of untreated human BBB-ECs. Pre-treatment with Ninjurin-1 blocking Ab significantly restricts the migration of $CD14^+$ monocytes across BBB-ECs. Data shown are representative of five independent experiments (n=5 blood donors) performed in triplicate using three distinct BBB-EC preparations.

Effect of Ninjurin-1 Blockade on Immune Cell Migration Across the Human BBB Endothelium Using an in vitro model of the human BBB (FIG. 5A), it was demonstrated that pre-treatment of BBB-endothelial cells with the human blocking peptide $Ninj_{26-37}$ or with an anti-Ninjurin-1 blocking antibody decreases the migration of freshly isolated (ex vivo) peripheral blood human $CD14^+$ monocytes across the endothelium (FIG. 5C and FIG. 11). The blocking $Ninj_{26-37}$ peptide did not any effect on the migration of $CD4^+$ and $CD8^+$ T lymphocytes in this model (FIG. 5B). FIG. 5D shows that Ninjurin-1 staining is observed around CFSE-loaded migrating $CD14^+$ monocytes and in the transmigratory cup (arrowheads). A similar decrease in $CD14^+$ monocyte migration across the endothelium was observed when monocytes were pre-treated for 1 h with an anti-Ninjurin-1 blocking antibody (FIG. 11)

EXAMPLE 5

Effect of Ninjurin-1 Blockade in Murine Models of Neuroinflammation

Figure 6A:
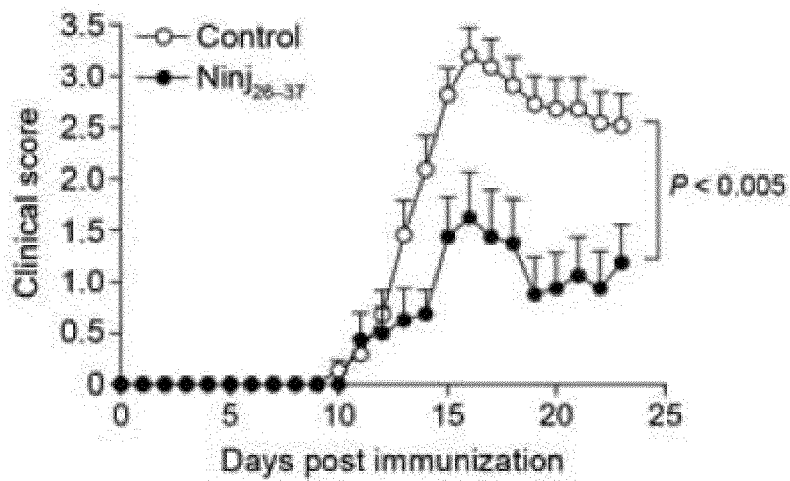
FIGS. 6A-D show the clinical effects of Ninjurin-1 blocking peptide ($Ninj_{26-37}$) in EAE mice. EAE was induced by active immunization with $MOG_{35-55}$/CFA in C57BL/6 mice. Some animals received intraperitoneal (i.p.) injections of 200 µg twice a day (b.i.d.) of mouse $Ninj_{26-37}$ from day 3 to day 23 post-immunization (●, n=24 mice); others received PBS (○, n=22 mice) in the same manner.
Figure 6B:
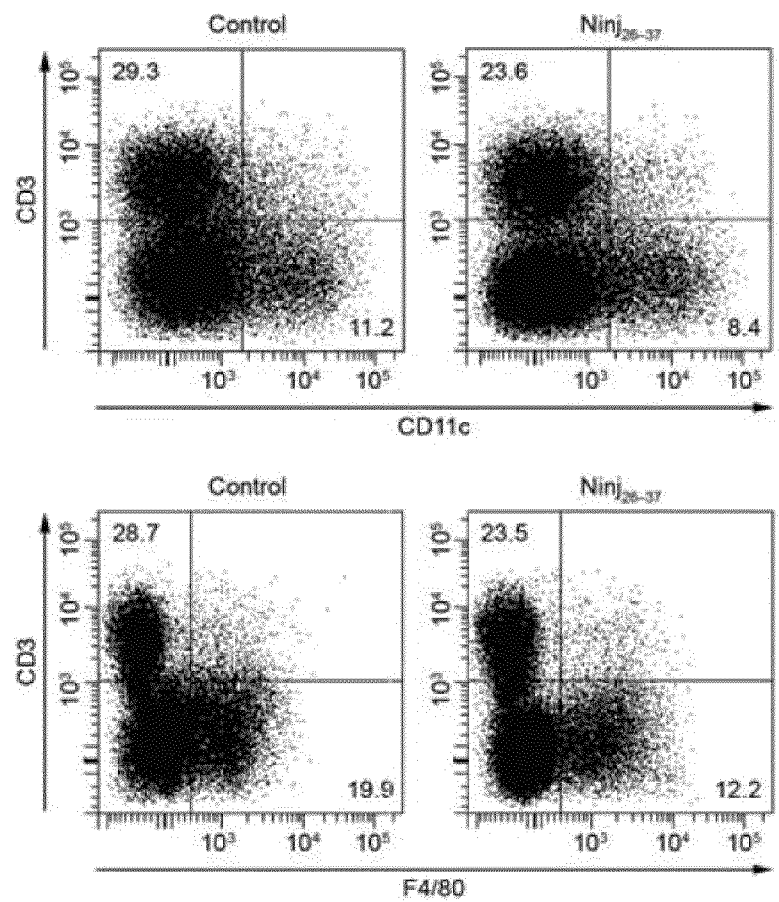
Figure 6C:
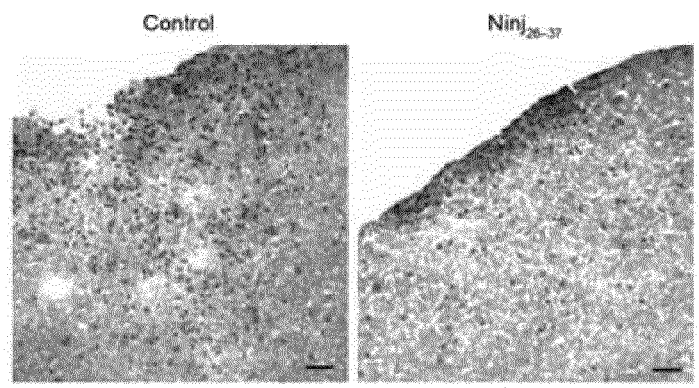
Figure 6D:
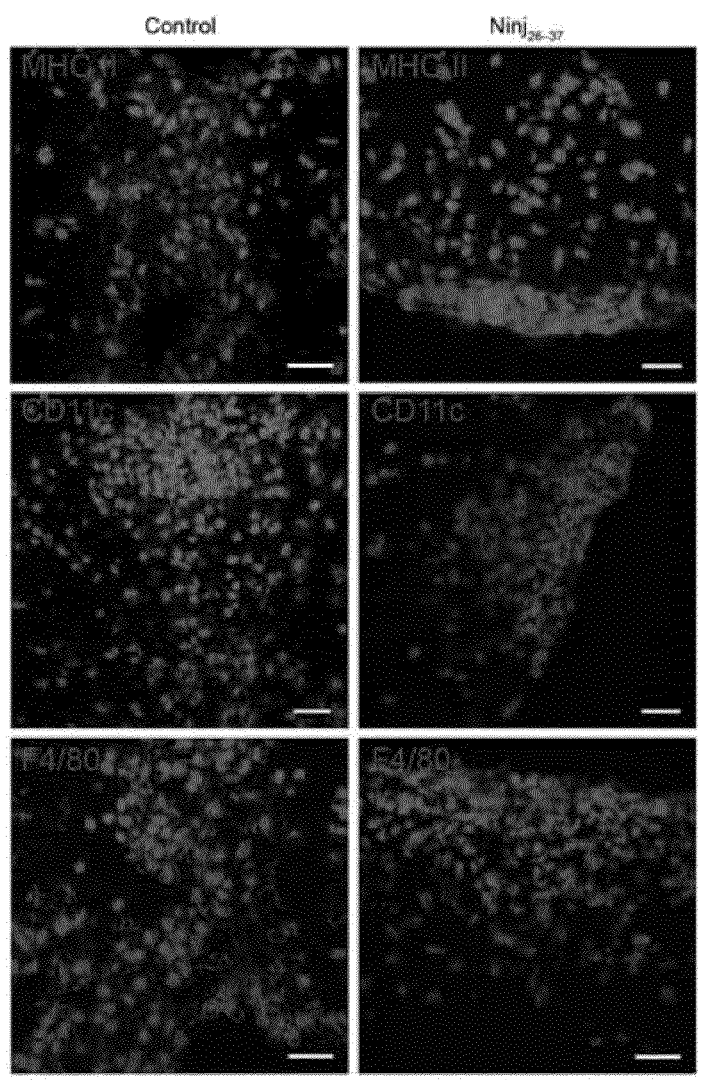
Figure 15:
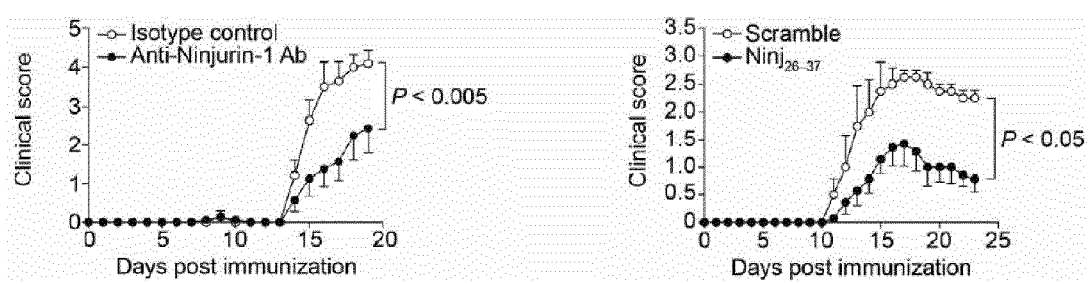
FIG. 15 shows the effect of Ninjurin-1 blockade on EAE clinical scores. Experimental allergic encephalomyelitis (EAE) was induced by active immunization in C57BL/6 animals with $MOG_{35-55}$/CFA. Disease score was measured as follows: 0, no clinical symptoms; 1, floppy tail; 2, ataxia; 3, paralysis of one hind limb; 4, paralysis of both hind limbs, 5, moribund. Left panel: Anti-Ninjurin-1 blocking antibody (Ab) or isotype control (150 mg per injection per mouse) were injected intraperitoneally (i.p.) on day 4, 6, 8 and 10 post-induction (n=8 mice). Mice treated with anti-Ninjurin-1 Ab (●) show a significant reduction in clinical scores as compared to isotype control animals (○). Right panel: Ninjurin-1 blocking peptide ($Ninj_{26-37}$) or scramble (200 mg twice daily per mouse) were injected i.p. from day 3 to 23 post-immunization (n=8 mice). Mice treated with $Ninj_{26-37}$ blocking peptide (●) show a significant reduction in clinical scores as compared to scramble-treated animals (○)
Figure 17:
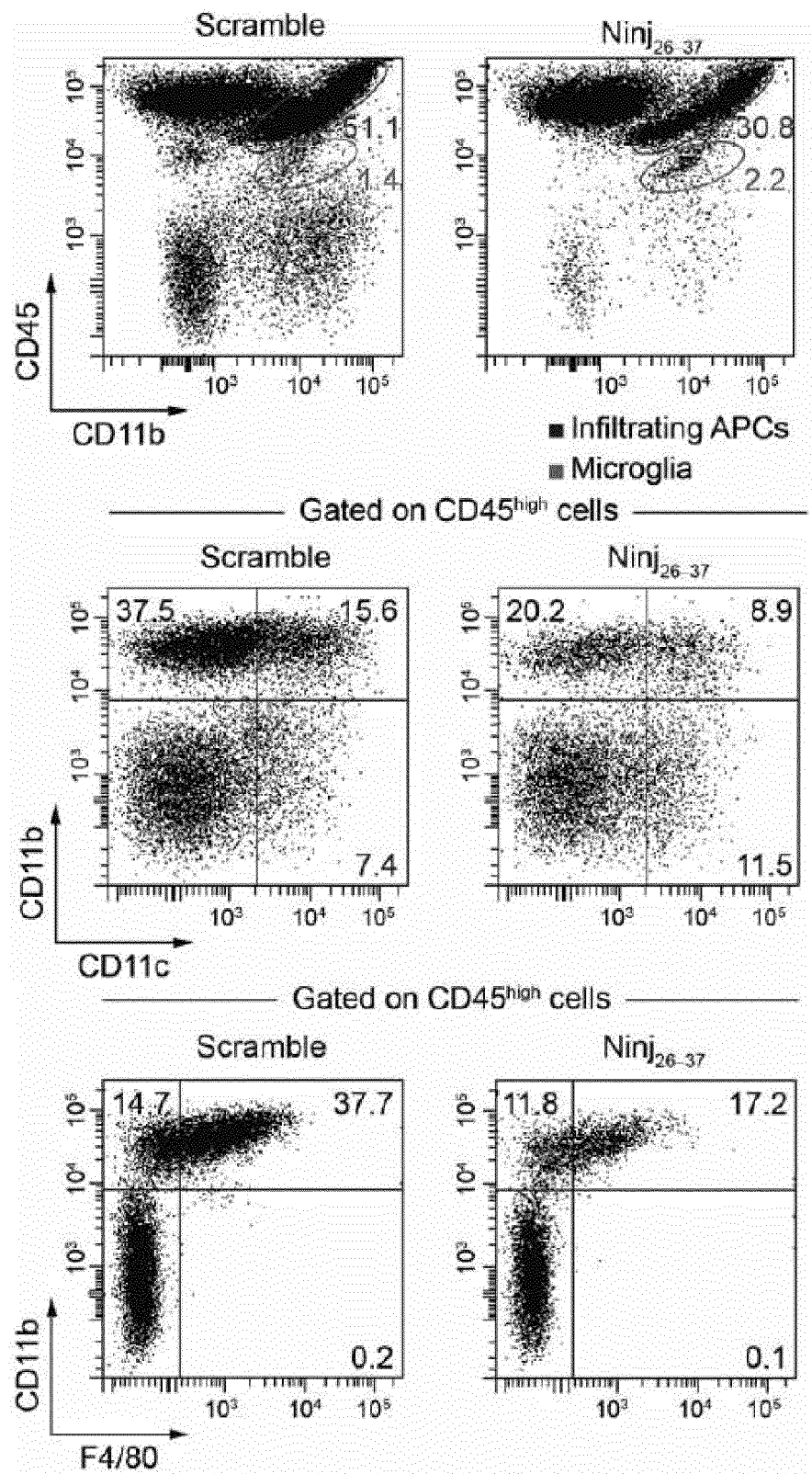
FIG. 17 shows the effect of Ninjurin-1 blockade with blocking peptide on APC infiltration in EAE mice. Flow cytometry analysis of CNS infiltrating cells in EAE mice 14 days post-immunization, comparing the number of $CD45^{hi}$ $CD11b^+$ infiltrating APCs (upper ovals), $CD45^{lo}$ $CD11b^+$ microglia (lower ovals) (upper panels), $CD45^{hi}$ $CD11b^+$ $CD11c^+$ DCs (middle panels) and $CD45^{hi}$ $CD11b^+$ $F4/80^+$ macrophages (lower panels) in Ninjurin-1 blocking peptide ($Ninj_{26-37}$) vs. scramble mice. The percentage of $CD45^{hi}$ $CD11b^+$ infiltrating APCs was markedly reduced in animals treated with $Ninj_{26-37}$ blocking peptide as compared to those treated with the scramble peptide. Conversely, the percentage of $CD45^{hi}$ $CD11b^+$ microglia remained unchanged between the different groups. Analysis of the specific subtypes of APCs revealed a reduction in infiltrating $CD45^{hi}$ $CD11b^+$ $CD11c^+$ DCs and $CD45^{hi}$ $CD11b^+$ $F4/80^+$ macrophages in the CNS of EAE mice treated with the $Ninj_{26-37}$ blocking peptide relative to the scramble group. Data shown are representative of two independent experiments obtained from four mice.
Figure 18A:
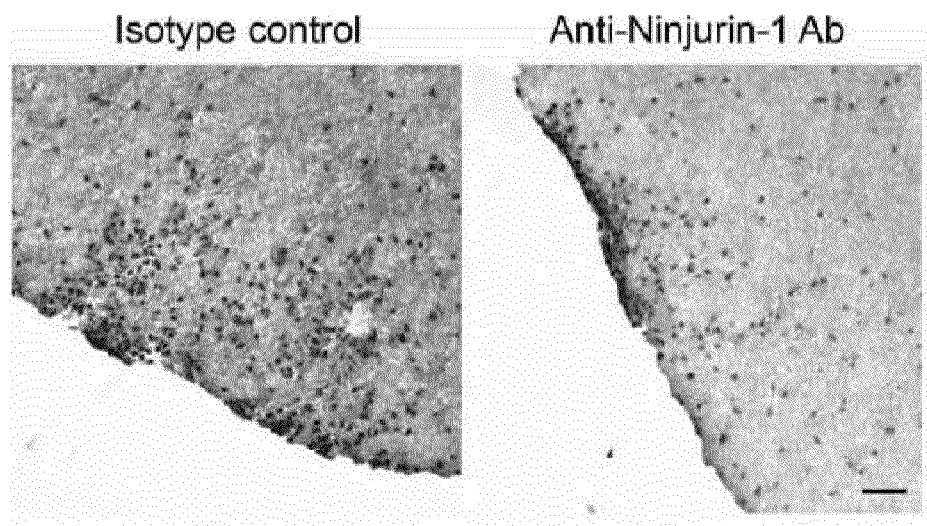
FIGS. 18A and B show the effect of Ninjurin-1 blockade on demyelination and immune cell infiltration in the CNS of EAE mice. EAE was induced by active immunization in C57BL/6 animals with $MOG_{35-55}$/CFA.
Figure 18B:
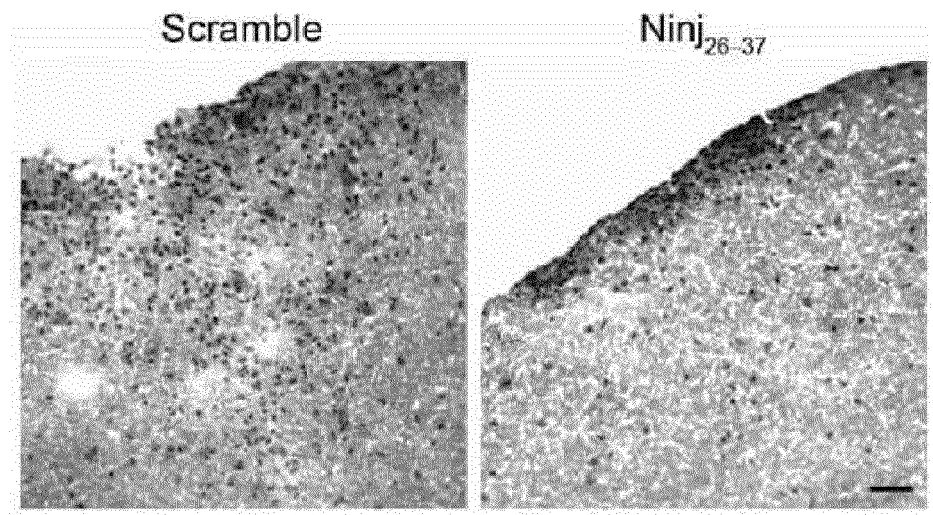
FIG. 18B: $Ninj_{26-37}$ blocking peptide or scramble peptide (200 μg twice daily per mouse) were injected i.p. from day 3 to 23 post-immunization (n=8 mice). Luxol fast blue-hematoxylin and eosin stainings of EAE spinal cord from Ninjurin-1-treated mice show a reduction in immune cell infiltration and demyelination, as compared to the control groups. Photomicrographs shown are representative of >20 stainings performed on four animals. Scale bar, 50 mm.
Figure 19A:
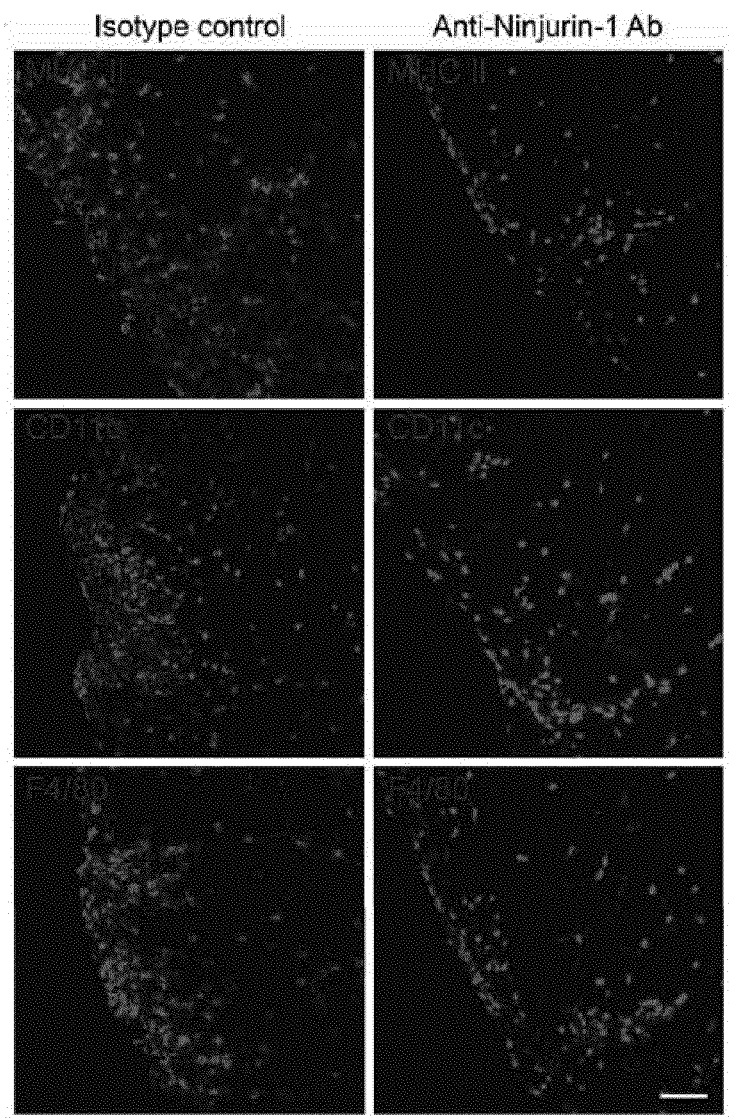
FIGS. 19A and B show the effect of Ninjurin-1 blockade with a blocking antibody on myeloid cell infiltration into the CNS of EAE mice. EAE was induced by active immunization in C57BL/6 animals with $MOG_{35-55}$/CFA. Anti-Ninjurin-1 blocking antibody (Ab) or isotype control (each 150 μg per injection per mouse) were injected intraperitoneally (i.p.) on day 4, 6, 8 and 10 post-induction (n=8 mice). Immunostainings (FIG. 19A) and cell counts (FIG. 19B) of MHC $II^+$ (upper panels in A, left bars in B), $CD11c^+$ (middle panels in A, middle bars in B) and $F4/80^+$ (lower panels in A, right bars in B) cells in spinal cord sections (14 days post-immunization) confirmed the significant reduction of infiltrating myeloid cells in anti-Ninjurin-1-treated mice as compared to the isotype control animals. Nuclei were stained with TO-PRO-3. Photomicrographs shown are representative of >20 immunostainings performed on post-mortem material from 4 animals. Scale bar, 30 μm.
Figure 19B:
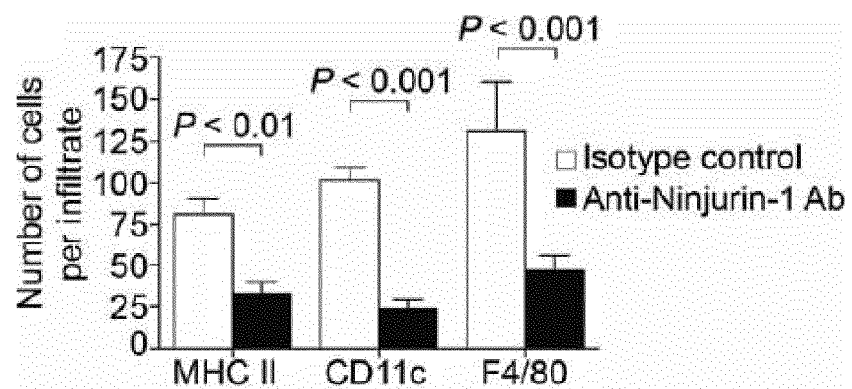
Figure 20A:
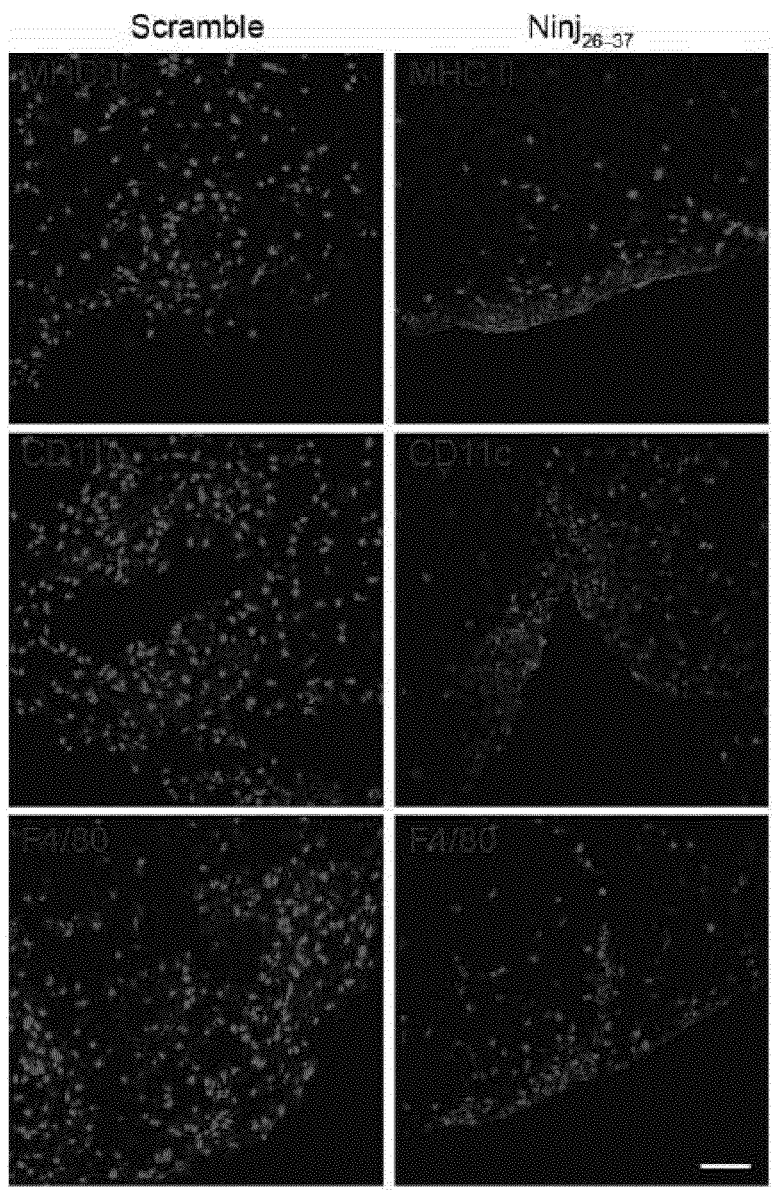
FIGS. 20A and 20B show the effect of Ninjurin-1 blockade with a blocking peptide on myeloid cell infiltration into the CNS of EAE mice. EAE was induced by active immunization in C57BL/6 animals with $MOG_{35-55}$/CFA. Ninjurin-1 blocking peptide ($Ninj_{26-37}$) or scramble (200 mg twice daily per mouse) were injected intraperitoneally (i.p.) on from day 3 to 23 post-immunization (n=8 mice). Immunostainings (FIG. 20A) and cell counts (FIG. 20B) of MHC IL (upper panels in A, left bars in B), $CD11c^+$ (middle panels in A, middle bars in B) and $F4/80^+$ (lower panels in A, right bars in B) cells in spinal cord sections (14 days post-immunization) confirmed the significant reduction of infiltrating myeloid cells in mice treated with the $Ninj_{26-37}$ peptide as compared to scramble animals. Nuclei were stained with TO-PRO-3. Photomicrographs shown are representative of >20 immunostainings performed on post-mortem material from 4 animals. Scale bar, 30 μm.
Figure 20B:
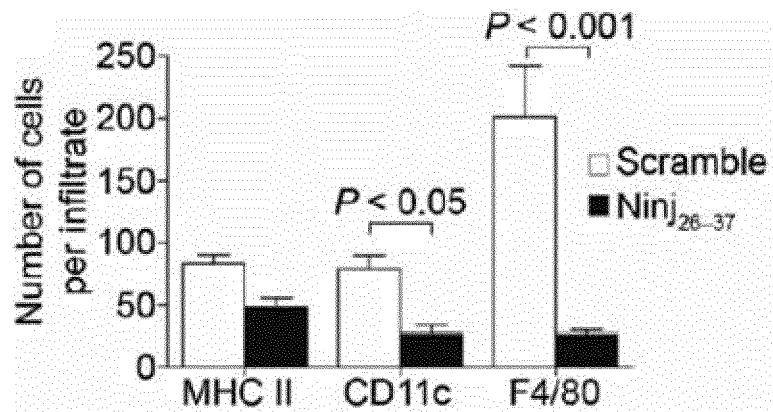
Figure 21:
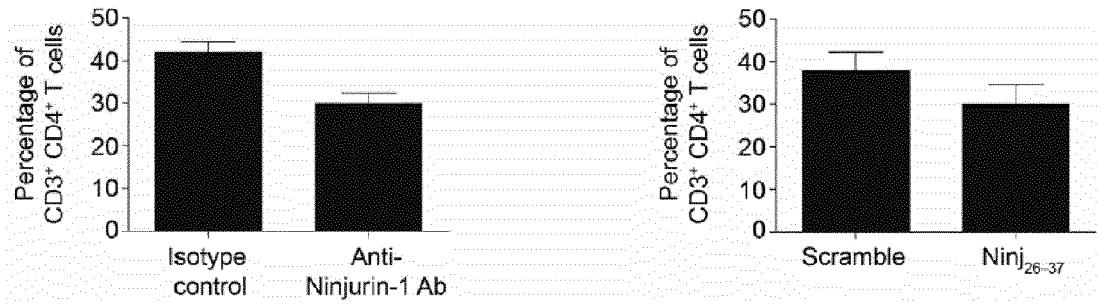
FIG. 21 shows the effect of Ninjurin-1 blockade on $CD3^+$ $CD4^+$ T cell infiltration into the CNS. Frequency of $CD4^+$ T lymphocytes in the CNS of EAE mice. Mice treated with anti-Ninjurin-1 blocking Ab (left panel) or $Ninj_{26-37}$ blocking peptide (right panel) exhibit moderate reduction of $CD3^+$ $CD4^+$ cells in the CNS as compared to either isotype control- or scramble-injected animals. Data shown are representative of two independent experiments obtained from four mice. Error bars represent the SEM.
Figure 22:
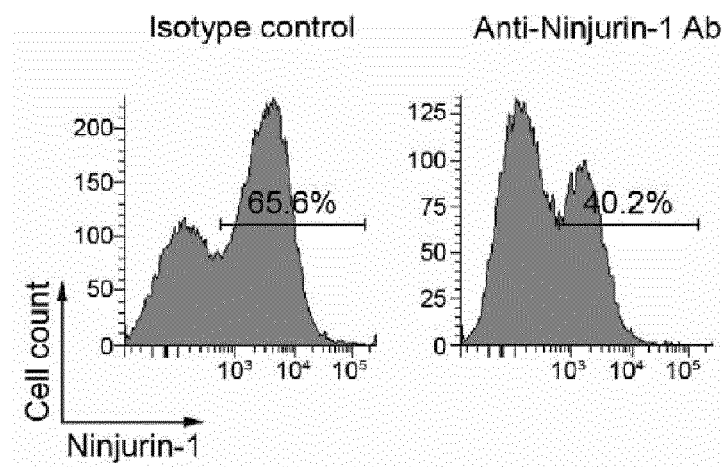
FIG. 22 shows the effect of Ninjurin-1 blockade with a blocking antibody on Ninjurin-1$^+$ cell infiltration into the CNS of EAE mice. Ninjurin-1 expression on CNS cells (brain and spinal cord homogenates) from $MOG_{35-55}$-immunized mice. Mice treated with anti-Ninjurin-1 blocking Ab have less Ninjurin-1$^+$ CNS cells (right panel) as compared to isotype control-treated mice (left panel). Data shown are representative of two independent experiments obtained from four mice.
Figure 23:
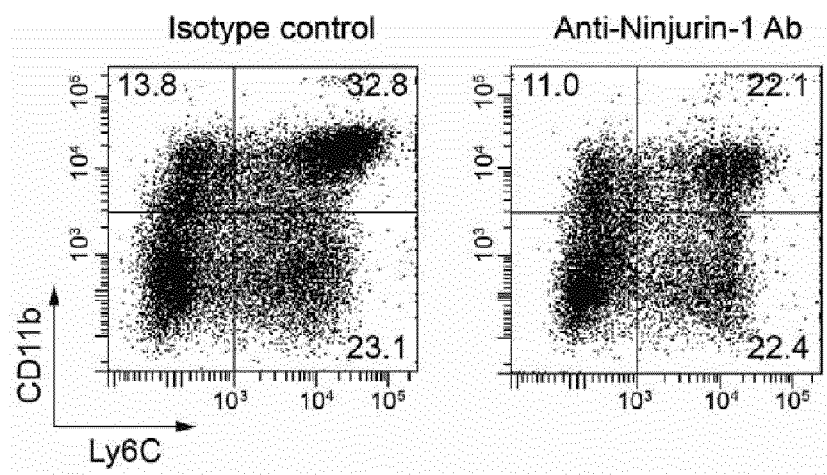
FIG. 23 shows the effect of Ninjurin-1 blockade with a blocking antibody on inflammatory antigen-presenting cell infiltration into the CNS of EAE mice. Ly6C expression on CNS cells (brain and spinal cord homogenates) from $MOG_{35-55}$-immunized mice. Mice treated with anti-Ninjurin-1 blocking Ab have less $CD11b^+$ $Ly6C^+$ inflammatory antigen-presenting cells (APCs) (right panel) as compared to isotype control-treated mice (left panel). Data shown are representative of two independent experiments obtained from four mice.

Two distinct murine models of CNS inflammation were used: EAE (autoimmune-based inflammation, mimicking MS in humans) and SCI (traumatic- or injury-induced inflammation). As shown above, Ninjurin-1 is expressed in the CNS of mice affected with EAE, and on infiltrating $CD11b^+$ antigen presenting cells (FIG. 14), infiltrating $F4/80^+$ macrophages and $CD11c^+$ dendritic cells (FIG. 4). EAE was induced by active immunization of C57BL/6 mice with $MOG_{35-55}$ peptide, as described above. Some animals received i.p. injections of 200 μg b.i.d. of $Ninj_{26-37}$ from day 3 to day 23 post-immunization; while control animals received a scramble peptide or a physiological saline solution. The data depicted in FIG. 6A and FIG. 15 (right panel) shows a significant reduction of the neurological signs, symptoms and clinical scores of the disease in animals treated with the $Ninj_{26-37}$ blocking peptide as compared to the control group. A significant decrease in EAE clinical scores was also observed following administration of an anti-Ninjurin-1 blocking antibody (FIG. 15, left panel), and the number of animals with EAE clinical scores ≥3.0 from day 11 to 17 post-immunization is decreased in the groups treated with the anti-Ninjurin-1 blocking antibody or the $Ninj_{26-37}$ blocking peptide, relative to control groups (FIG. 16), demonstrating a decrease in severity. The histopathological analysis shows an important reduction in tissue damage (demyelination) and immune cell infiltration in animals treated with $Ninj_{26-37}$ (FIGS. 6D and 18B) or anti-Ninjurin-1 Ab (FIG. 18A). Furthermore, a reduction of infiltrating immune cells (more particularly myeloid cells such as $F4/80^+$ macrophages and $CD11c^+$ dendritic cells) was also observed by flow cytometry (FIGS. 6B and 17) and immunofluorescence (FIGS. 6D, 18A, 18B, 19A, 19B, 20A and 20B) in mice treated with a blocking anti-Ninjurin-1 antibody or $Ninj_{26-37}$ blocking peptide. The frequency of $CD4^+$ T lymphocytes in the CNS of EAE mice was moderately reduced in mice treated with anti-Ninjurin-1 blocking Ab (FIG. 21, left panel) or $Ninj_{26-37}$ blocking peptide (FIG. 21, right panel), as compared to either isotype control- or scramble-injected animals. FIG. 22 shows that EAE mice treated with anti-Ninjurin-1 blocking Ab (right panel) have less Ninjurin-1$^+$ CNS cells (brain and spinal cord homogenates) as compared to isotype control-treated mice (left panel). Also, mice treated with anti-Ninjurin-1 blocking Ab have less $CD11b^+$ $Ly6C^+$ "inflammatory" antigen-presenting cells (right panel) as compared to isotype control-treated mice (left panel). Data shown are representative of two independent experiments obtained from four mice.

Figure 7C:
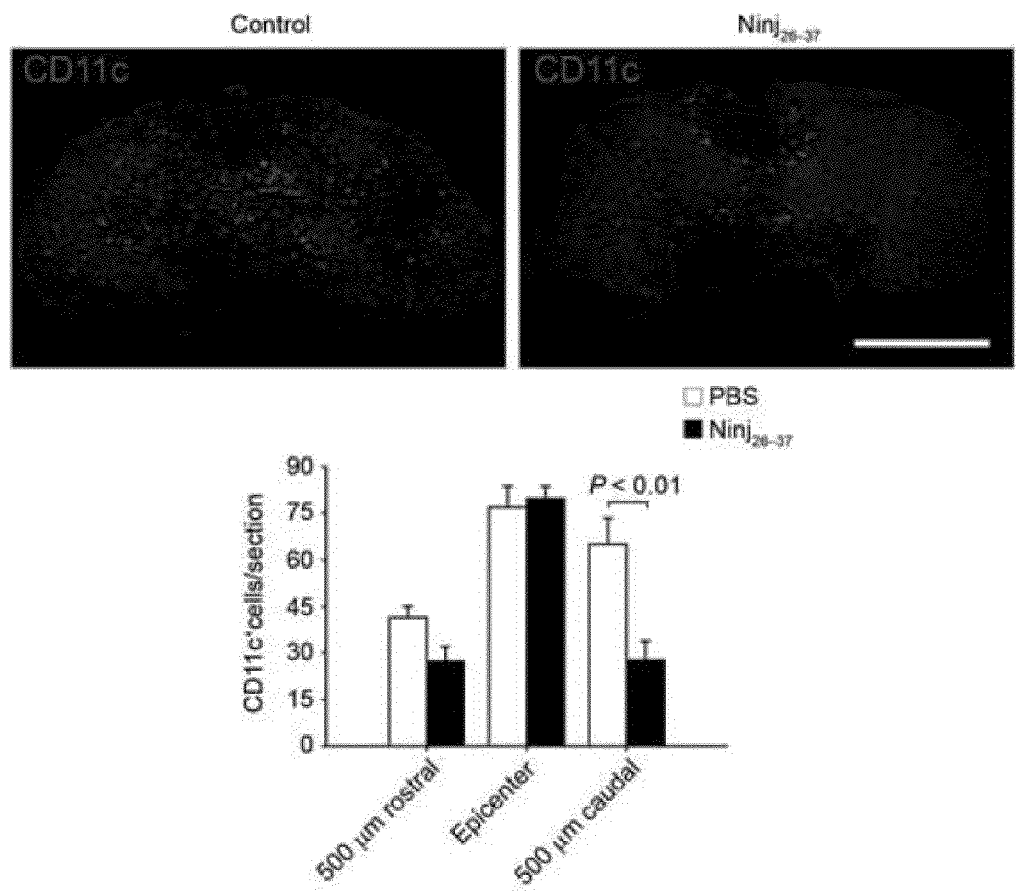
Figure 7D:
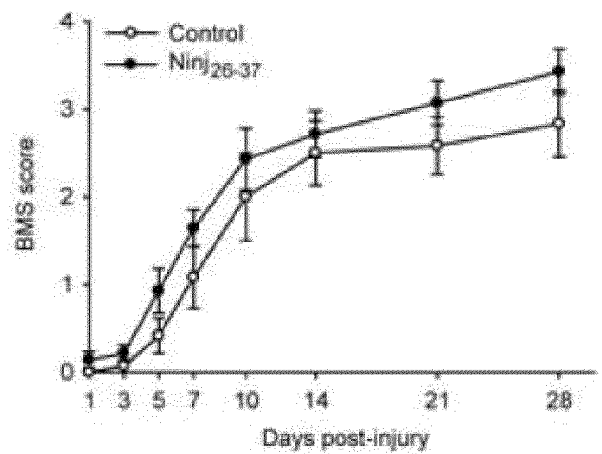

The infiltration of myeloid cells in the injured spinal cord significantly contributes to tissue damage and delays the clinical and pathological recovery in the murine model of SCI. SCI experiments were performed with the Infinite Horizons™ impactor device (Precision Scientific Instrumentation). FIG. 7A shows that there is a significant increase in the expression of Ninjurin-1 in spinal cord homogenates of injured mice. Neutralization of Ninjurin-1 was performed with the murine $Ninj_{26-37}$ blocking peptide after SCI. Some animals received i.p. injections of 200 μg b.i.d. of $Ninj_{26-37}$ from day 1 to 7 following injury, and the control group was injected in the same manner with an irrelevant peptide (sequence: WRGNPGIRWAPH, SEQ ID NO: 12). The infiltration of Iba1+ (FIG. 7B) and CD11c+ (FIG. 7C) myeloid cells in the spinal cord of SCI animals treated with Ninj$_{26-37}$ blocking peptide was reduced as compared to animals treated with the control peptide. Also, the clinical scores (Basso mouse scale, BMS) of mice treated with 200 μg of the Ninj$_{26-37}$ blocking peptide were reduced as compared to control animals (FIG. 7D).

EXAMPLE 6

Figure 9A:
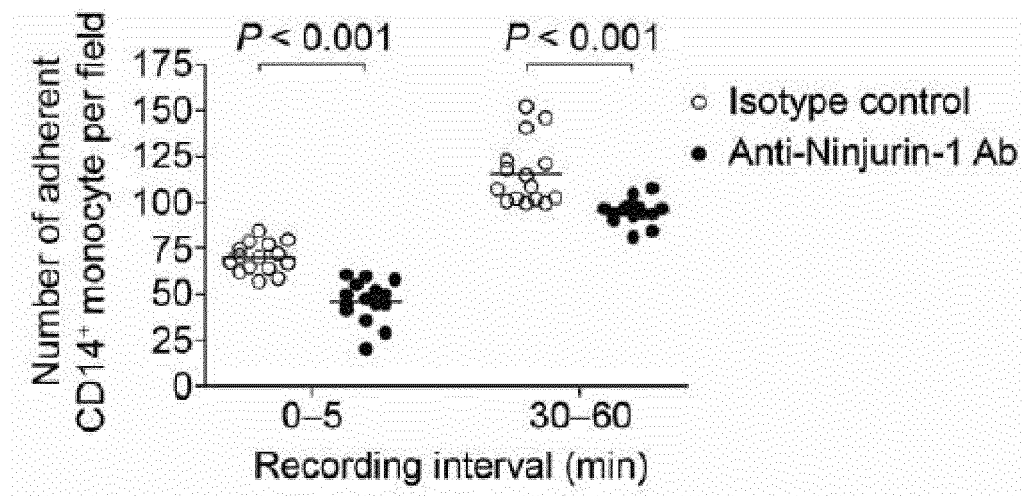
FIGS. 9A and 9B show the effect of Ninjurin-1 blockade on monocyte adhesion to a BBB-ECs monolayer in an in vitro flow system. Monocyte-BBB-EC interactions were analyzed under physiologic shear stress conditions. BBB-ECs were grown to confluence on flow capillary slides (Ibidi microslide I Luer 0.6 mm). Primary cultures of human BBB-ECs were then submitted to flow conditions (0.43 ml/min, Ibidi pump system) and CFSE-labelled ex vivo isolated monocytes were added in the presence of the sheep anti-human Ninjurin-1 blocking antibody (Ab) or the isotype control, a sheep IgG (10 µg/ml, FIG. 9A) or Ninjurin blocking peptide ($Ninj_{26-37}$) or the scramble peptide (0.4 mM, FIG. 9B). Pictures of adherent $CD14^+$ monocytes were captured between 0-5 min and 30-60 min after addition of cells in the flow system. Volocity™ software was used to determine the number of adherent cells per frame, which is represented by a single dot. For each recording interval, 15 pictures were taken randomly. Bars are representative of the mean for a data set. Ninjurin-1 blockade with either the antibody (Ab) (FIG. 9A) or the peptide ($Ninj_{26-37}$) (FIG. 9B) significantly restricts the adhesion of $CD14^+$ monocytes on BBB-ECs as compared to the corresponding controls. Data shown are representative of four independent experiments (n=4 blood donors each).
Figure 9B:
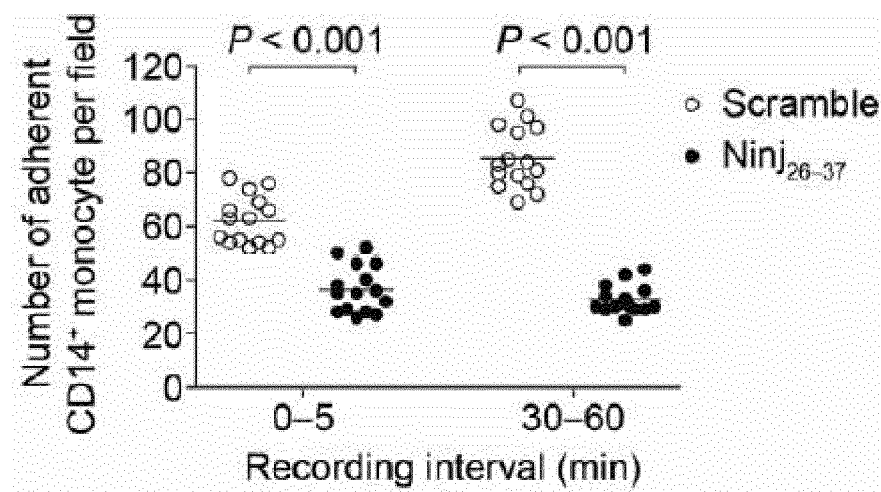
Figure 10A:
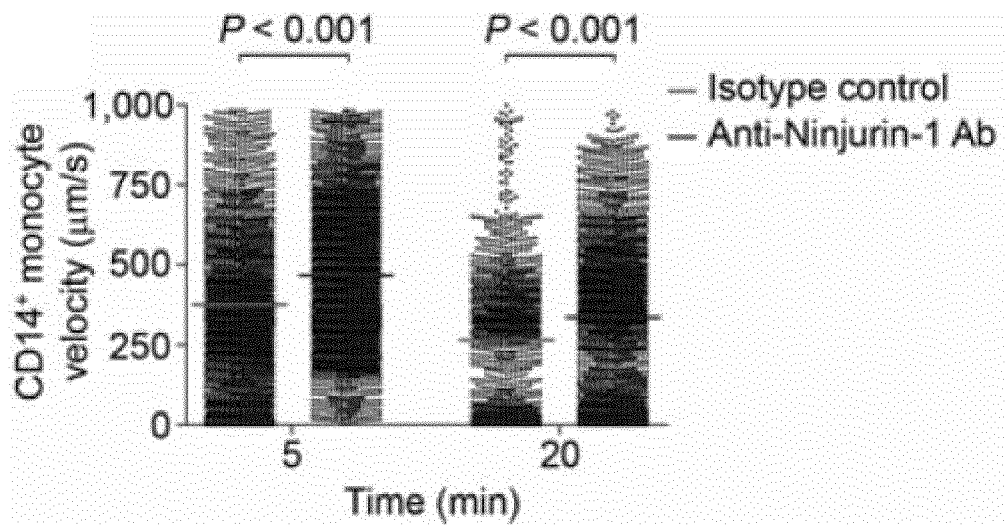
FIGS. 10A and 10B show the effect of Ninjurin-1 blockade on monocyte adhesion to a BBB-ECs monolayer in an in vitro flow system. Monocyte-BBB-EC interactions were analyzed under physiologic shear stress conditions. BBB-ECs were grown to confluence on flow capillary slides (Ibidi microslide I Luer 0.6 mm). Primary cultures of human BBB-ECs were then submitted to flow conditions (0.43 ml/min, Ibidi pump system) and CFSE-labelled ex vivo isolated monocytes were added in the presence of the sheep anti-human Ninjurin-1 blocking antibody (Ab) or the isotype control, a sheep IgG (10 µg/ml, FIG. 10A) or Ninjurin blocking peptide ($Ninj_{26-37}$) or the scramble peptide (0.4 mM, FIG. 10B). 30 sec videos were acquired 5 min and 20 min after addition of monocytes to the flow system. The velocity was determined with an algorithm using the Volocity™ software. Each dot represents the mean velocity of a single cell throughout the field of view. The bars are representative of the mean for a data set. Ninjurin-1 blockade with either the antibody or the peptide significantly restricts the adhesion of $CD14^+$ monocytes on BBB-ECs. For each experiment, 3 videos per time-point were analyzed. Data shown are representative of four independent experiments (n=4 blood donors each). Left bars=control (isotype control or scramble peptide), right bars=anti-Ninjurin-1 blocking antibody or Ninjurin blocking peptide.
Figure 10B:
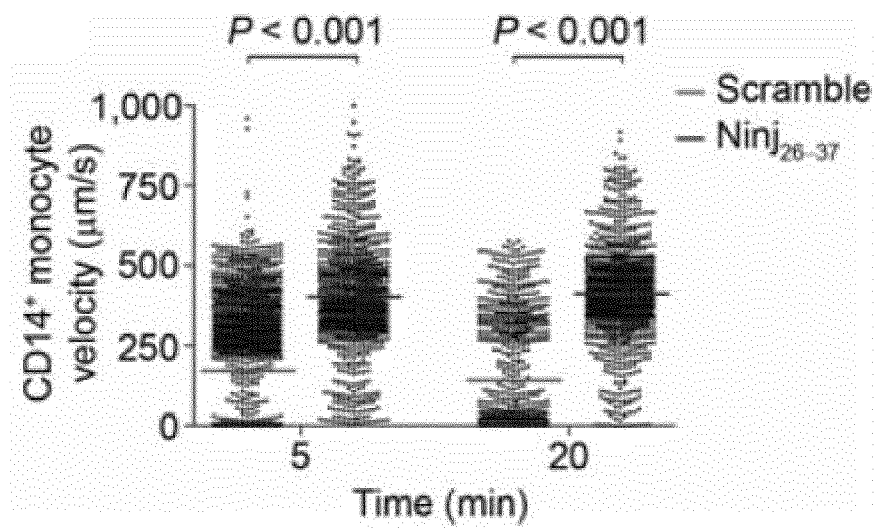

Effect of Ninjurin-1 Blockade on Monocyte Adhesion to a BBB-ECs Monolayer in an In Vitro Flow System The effect of Ninjurin-1 blockade on monocyte adhesion to a BBB-ECs monolayer was tested in an in vitro flow system. The results presented in FIGS. 9A and 9B shows that the Ninjurin-1 blocking peptide (FIG. 9A) and the anti-Ninjurin blocking antibody (FIG. 9B) significantly reduce the number of adherent monocytes to BBB-ECs under flow conditions. Furthermore, Ninjurin-1 blockade by the peptide (FIG. 10A) or the antibody (FIG. 10B) significantly increases the monocyte mean velocity of the monocytes, demonstrating a reduced adhesion/interaction of the monocytes to the BBB-ECs monolayer.

EXAMPLE 7

Effect of Ninjurin-1 Blockade on T Cell Proliferation

Figure 13A:
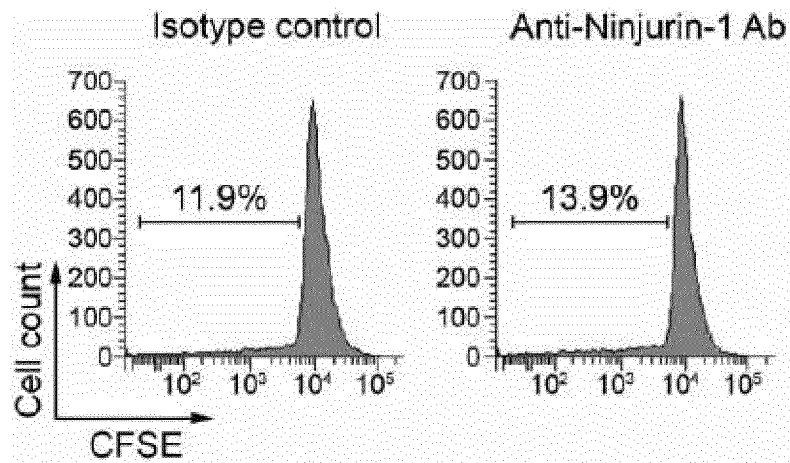
FIGS. 13A-C show the effect of Ninjurin-1 neutralization on T cell proliferation.
Figure 13B:
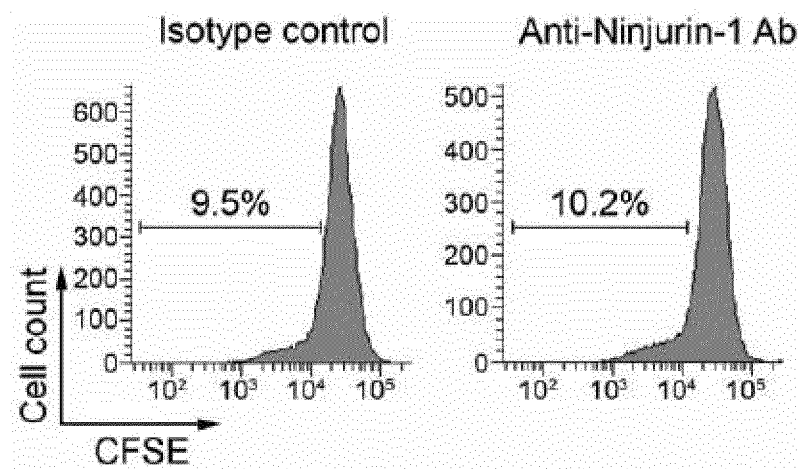
Figure 13C:
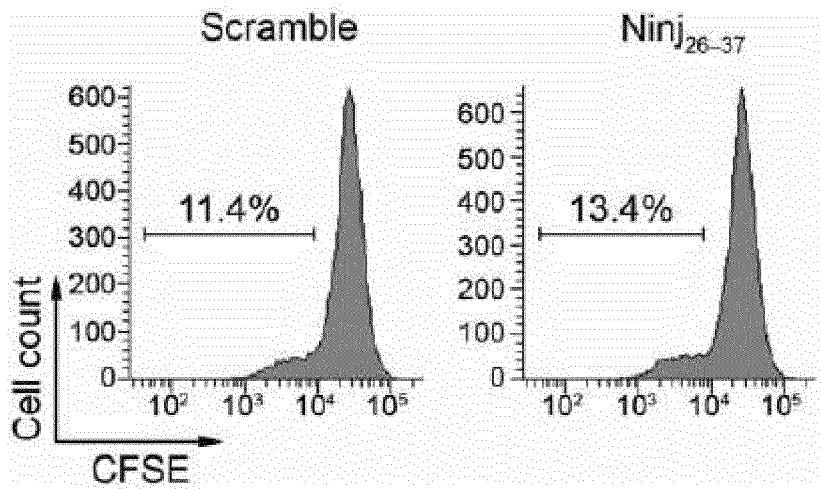

The effect of Ninjurin-1 neutralization on T cell proliferation was assessed. FIG. 13A show that the anti-Ninjurin-1 blocking antibody does not significantly affect the proliferation of memory CD4+ CD45RO+ T lymphocytes cultured with CD14+ monocytes loaded with the hemagglutinin (HA)$_{306-318}$ peptide. Similarly, Ninjurin-1 blockade with an antibody did not significantly affect the proliferation of spleen and lymph node cells collected from EAE mice and stimulated with MOG$_{35-55}$ (FIGS. 13B and 13C).

The studies presented herein highlight the role of Ninjurin-1 in the recruitment of myeloid cells within the CNS, and in the pathophysiology of neuroinflammatory diseases/conditions. The selective blockade of Ninjurin-1-mediated recruitment of myeloid cells to the CNS reduces tissue destruction observed in inflammatory cerebral lesions, including the lesions induced by traumatic stress (e.g., SCI) as well as those associated with autoimmune inflammatory processes, as observed in MS, and is associated with a reduction in clinical symptoms associated with these conditions.

Although the present invention has been described hereinabove by way of specific embodiments thereof, it can be modified, without departing from the spirit and nature of the subject invention as defined in the appended claims.

---

The invention claimed is:

1. A method of reducing neural tissue damage and/or promoting neural tissue repair in a human subject suffering from multiple sclerosis or spinal cord injury, said method comprising administering to said subject an effective amount of an inhibitor of a human nerve injury-induced protein-1 (Ninjurin-1) polypeptide comprising the amino acid sequence of SEQ ID NO:2, wherein said inhibitor blocks Ninjurin-1/Ninjurin-1 homotypic interaction and is
   (a) a peptide consisting of formula II (SEQ ID NO: 14):

$$Xaa^1\text{-}Xaa^2\text{-}Arg\text{-}Trp\text{-}Xaa^3\text{-}Trp\text{-}Arg\text{-}Xaa^4\text{-}Xaa^5\text{-}Xaa^6\text{-}Xaa^7\text{-}Xaa^8 \quad (II),$$

wherein
   $Xaa^1$, $Xaa^2$, $Xaa^4$ and $Xaa^5$, $Xaa^6$, $Xaa^7$ and $Xaa^8$ is each independently any amino acid or is absent;
   $Xaa^3$ is any amino acid.

2. The method of claim 1, wherein said inhibitor of human Ninjurin-1 polypeptide binds to an extracellular domain of said human Ninjurin-1 polypeptide.

3. The method of claim 2, wherein said inhibitor of human Ninjurin-1 polypeptide binds to a domain comprising a motif corresponding to residues 28 to 35 of said human Ninjurin-1 polypeptide.

4. The method of claim 1, wherein
   (i) $Xaa^1$ is Pro;
   (ii) $Xaa^2$ is Ala;
   (iii) $Xaa^3$ is Gly;
   (iv) $Xaa^4$ is His;
   (v) $Xaa^5$ is Gly;
   (vi) $Xaa^6$ is Pro;
   (vii) $Xaa^7$ is Ile;
   (viii) $Xaa^8$ is Asn; or
   (ix) any combination of (i) to (viii).

5. The method of claim 1, wherein said peptide is Arg-Trp-Gly-Trp-Arg (SEQ ID NO: 15).

6. The method of claim 1, wherein said peptide is Arg-Trp-Gly-Trp-Arg-His-Gly-Pro (SEQ ID NO: 16).

7. The method of claim 1, wherein said peptide is Pro-Ala-Arg-Trp-Gly-Trp-Arg-His-Gly-Pro-Ile-Asn (SEQ ID NO: 5).

8. The method of claim 1, wherein said subject suffers from spinal cord injury (SCI).

9. The method of claim 1, wherein said subject suffers from multiple sclerosis (MS).

10. The method of claim 7, wherein said subject suffers from spinal cord injury (SCI).

11. The method of claim 7, wherein said subject suffers from multiple sclerosis (MS).

* * * * *